US008012995B1

(12) United States Patent
Arkinstall et al.

(10) Patent No.: US 8,012,995 B1
(45) Date of Patent: *Sep. 6, 2011

(54) PHARMACEUTICALLY ACTIVE SULFONAMIDE DERIVATIVES

(75) Inventors: Stephen Arkinstall, Belmont, MA (US);
Serge Halazy, Vetraz-Monthoux (FR);
Dennis Church, Commungny (FR);
Montserrat Camps, Versoix (FR);
Thomas Rueckle, Plan-les-Ouates (CH);
Jean Pierre Gotteland, Beaumont (FR);
Marco Biamonte, San Diego, CA (US)

(73) Assignee: Merck Serono SA, Coinsins, Vaud (CH)

( * ) Notice: Subject to any disclaimer, the term of this patent is extended or adjusted under 35 U.S.C. 154(b) by 818 days.

This patent is subject to a terminal disclaimer.

(21) Appl. No.: 10/070,954

(22) PCT Filed: Sep. 28, 2000

(86) PCT No.: PCT/IB00/01380

§ 371 (c)(1),
(2), (4) Date: Jul. 22, 2002

(87) PCT Pub. No.: WO01/23378

PCT Pub. Date: Apr. 5, 2001

(30) Foreign Application Priority Data

Sep. 28, 1999 (EP) .................................... 99810869

(51) Int. Cl.
| | | |
|---|---|---|
| *A61P 25/00* | (2006.01) | |
| *A61P 9/00* | (2006.01) | |
| *A61K 31/4436* | (2006.01) | |
| *A61K 31/4439* | (2006.01) | |
| *A61K 31/44* | (2006.01) | |
| *C07D 417/14* | (2006.01) | |
| *C07D 417/12* | (2006.01) | |
| *C07D 409/14* | (2006.01) | |
| *C07D 409/12* | (2006.01) | |
| *C07D 213/74* | (2006.01) | |

(52) U.S. Cl. ........ 514/322; 514/323; 514/326; 546/199; 546/201; 546/212

(58) Field of Classification Search .................. 514/326, 514/322, 323; 546/199, 201, 212
See application file for complete search history.

(56) References Cited

U.S. PATENT DOCUMENTS

| | | | | |
|---|---|---|---|---|
| 5,106,983 | A | 4/1992 | Reiff et al. ..................... | 546/224 |
| 5,843,906 | A * | 12/1998 | Chandrakumar et al. ...... | 514/19 |
| 6,020,357 | A * | 2/2000 | Pinto et al. ..................... | 514/406 |
| 6,399,603 | B1 * | 6/2002 | Jacobs et al. ................ | 514/234.5 |
| 6,506,901 | B2 * | 1/2003 | Steffan et al. .................. | 546/192 |

FOREIGN PATENT DOCUMENTS

| | | | |
|---|---|---|---|
| SU | 1 706 174 | * | 10/1995 |
| WO | WO 91/13872 A1 | | 9/1991 |
| WO | WO 96/06609 A1 | | 3/1996 |
| WO | WO 96/30017 A1 | | 10/1996 |
| WO | WO 97/30992 A1 | | 8/1997 |
| WO | WO 97/45403 A1 | | 12/1997 |
| WO | WO 98/49188 A1 | | 11/1998 |
| WO | WO 98/53814 A1 | | 12/1998 |
| WO | WO 99/16751 A1 | | 4/1999 |
| WO | WO 99/21859 A1 | | 5/1999 |
| WO | WO 00/32577 | * | 6/2000 |
| WO | WO 01/23379 | | 4/2001 |
| WO | WO 01/23382 | | 4/2001 |

OTHER PUBLICATIONS

Weston et al., The JNK Signal Transduction Pathway, Current Opinion in Genetics and Development, vol. 12, No. 1, pp. 14-21, Feb. 2002.*
Caplus printout of Grigoryan et al., Armyanskii Khimicheskii Zhurnal, vol. 42, No. 4, pp. 236-240, 1989.*
Caplus printout of Kaldrikyan et al., Khimiko-Farmatsevticheskii Zhurnal, vol. 18, No. 1, pp. 58-61, 1984.*
Caplus Printout of Palaima et al., Synthesis of Substituted 6-aminonaphthalene-1-sulfamides, Chemija, 1991, vol. 3, pp. 144-153.*
Kelly J. et al.: "Synthesis of isomeric 3-piperidinyl and 3-pyrrolidinyl benzo '5,6! Cyclohepta '1,2-b!pyridines: sulfonamido derivatives as inhibitors of Ras prenylation", Bioorg. Med. Chem., 1998, vol. 6, pp. 673-686.
Xie et al.: "Cyrstal structure of JNK3: a kinase implicated in neuronal apoptosis", Structure Aug. 15, 1998, pp. 983-991.
Yang et al.: "Absence of excitotoxicity-induced apoptosls in the hippocampus of mice lacking the Jnk3 gene", Nature, vol. 389, Oct. 23, 1997. pp. 865-870.
Yang et al.: "Differentiation of CD4+ T Cells to Th1 Cells Requires MAP Kinase JNK2", Immunity, vol. 9, 575-585, Oct. 1998.
Sabapathy et al.: "JNK2 is required for efficient T-cell activation and apoptotis bdt not for normal lymphocyte development", Current Biology 1999, vol. 9, pp. 116-125.
Kumagae et al.: "Human c-Jun N-terminal kinase expression and activation in the nervous system", Molecular Brain Research 1999, vol. 67, pp. 10-17.

* cited by examiner

*Primary Examiner* — Brenda Coleman
(74) *Attorney, Agent, or Firm* — Browdy and Neimark, PLLC

(57) ABSTRACT

The present invention is related to sulfonamide derivatives of formula (I0 notably for use as pharmaceutically active compounds, as well as to pharmaceutical formulations containing such sulfonamide derivatives. Said sulfonamide derivatives are efficient modulators of the JNK pathway, they are in particular efficient and selective inhibitors of JNK 2 and 3. The present invention is furthermore related to novel sulfonamide derivatives as well as to methods of their preparation. The compounds of formula (I) according to the present invention being suitable pharmaceutical agents are those wherein $Ar^1$ and $Ar^2$ are independently from each other substituted or unsubstituted aryl or heteroaryl groups, X is O or S, preferably O; $R^1$ is hydrogen or a $C_1$-$C_6$-alkyl group, or $R^1$ forms a substituted or unsubstituted 5-6 membered saturated or unsaturated ring with $Ar^1$; n is an integer from 0 to 5, preferably between 1-3 and most preferred 1; Y within formula (I) is an unsubstituted or a substituted 4-12-membered saturated cyclic or bicyclic alkyl containing at least one nitrogen atom, whereby one nitrogen atom, whereby one nitrogen atom within said ring is forming a bond with the sulfonyl group of formula (I) thus providing a sulfonamide.

19 Claims, No Drawings

PHARMACEUTICALLY ACTIVE SULFONAMIDE DERIVATIVES

FIELD OF THE INVENTION

The present invention is related to sulfonamide derivatives for use as pharmaceutically active compounds, as well as pharmaceutical formulations containing such sulfonamide derivatives. In particular, the present invention is related to sulfonamide derivatives displaying a substantial modulatory, notably an inhibitory activity of the JNK (Jun-Kinase) function or pathways respectively, and which are therefore particularly useful in the treatment and/or prevention of disorders of the autoimmune and the neuronal system. The present invention is furthermore related to novel sulfonamide derivatives as well as to methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide, the chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those that have formed multiple synapses. This may reflect a process, which balances the relative number of pre- to postsynaptic neurons in the developing nervous system. Although neuronal cell death was assumed to be apoptotic, it was only recently that neurons in developing rodent brain were conclusively shown to undergo apoptosis as classified by morphology and DNA fragmentation. As cell death during development is clearly not a pathological process, it makes sense that cells actually cease to exist. Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are members of the SAPK/JNK being a sub-family of MAP Kinases (MAPKs).

MAPKs (mitogen-activated protein kinases) are serine/threonine kinases that are activated by dual phosphorylation on threonine and tyrosine residues. In mammalian cells, there are at least three separate but parallel pathways that convey information generated by extra-cellular stimuli to the MAPKs. Said pathways consist of kinase cascades leading to activation of the ERKs (extracellular regulated kinases), the JNKs (c-Jun N-terminal kinases), and the p38/CSBP kinases. While both the JNK and p38 pathways are involved in relaying stress-type extramolecular signals, the ERK pathway is primarily responsible for transducing mitogenic/differentiation signals to the cell nucleus. SAPK cascades represent a sub-family of the mitogen-activating protein kinase family, that are activated by different external stimuli including DNA damage following UV irradiation, TNF-$\alpha$, IL-$\beta$, ceramide, cellular stress, and reactive oxygen species and have distinct substrate specificities. Signal transduction via MKK4/JNK of MKK3/p38 results in the phosphorylation of inducible transcription factors, c-Jun and ATF2, which then act as either homodimers or heterodimers to initiate transcription of down-stream effectors.

c-Jun is a protein that is forming homodimers and heterodimers (with e.g. c-Fos) to produce the transactivating complex AP—which is required for the activation of many genes (e.g. matrix metalloproteinases) involved in the inflammatory response. The JNKs were discovered when it was found that several different stimuli such as UV light and TNF-$\alpha$ stimulated phosphorylation of c-Jun on specific serine residues in the N-terminus of the protein.

In a recent publication of Xie X et al, (*Structure* 1998, 6 (8); 983-991) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK3) and MAP kinase kinase 4 (MKK4), or c-Jun (part of the MKK-4 cascade) may be sufficient to block apoptosis (see also Kumagae Y et al, in *Brain Res Mol Brain Res*, 1999, 67(1), 10-17 and Yang D D et al in *Nature*, 1997, 389 (6653); 865-870). Within a few hours of NGF deprivation in SCG neurones, c-Jun becomes highly phosphorylated and protein levels increase. Similarly in rat PC-12 cells deprived of NGF, JNK and p38 undergo sustained activation while ERKs are inhibited. Consistent with this JNK3 KO mice are resistant to excitotoxicity induced apoptosis in the hippocampus and more importantly they display greatly reduced epileptic like seizures in response to excitotoxicity as compared to normal animals (*Nature* 1997, 389, 865-870). More recently, it has been reported that the JNK signalling pathway is implicated in cell proliferation and could play an important role in autoimmune diseases (*Immunity*, 1998, 9, 575-585; *Current Biology*, 1999, 3, 116-125) which are mediated by T-cell activation and proliferation.

Naive (precursor) $CD4^+$ helper T (Th) cells recognise specific MHC-peptide complexes on antigen-presenting cells (APC) via the T-cell receptor (TCR) complex. In addition to the TCT-mediated signal, a co-stimulatory signal is provided at least partially by the ligation of CD28 expressed on T-cells with B7 proteins on APC. The combination of these two signals induces T-cell clonal expression.

After 4-5 days of proliferation, precursor of $CD4^+$ T cells differentiate into armed effector Th cells that mediate the functions of the immune system. During the differentiation process, substantial reprogramming of gene expression occurs.

Two subsets of effector Th cells have been defined on the basis of their distinct cytokine secretion pattern and their immuno-modulatory effects: Th1 cells produce IFN$\gamma$ and LT (TNF-$\beta$), which are required for cell-mediated inflammatory reactions; Th2 cells secrete IL-4, IL-5, IL-6, IL-10 and IL-13, which mediate B cell activation and differentiation. These cells play a central role in the immune response. The JNK MAP Kinase pathway is induced in Th1 but not in Th2 effector cells upon antigen stimulation. Furthermore, the differentiation of precursor $CD4^+$ T cells into effector Th1 but not Th2 cells is impaired in JNK1 and JNK2-deficient mice. Therefore, in recent years it has been realised that the JNK kinase pathway plays an important role in the balance of Th1 and Th2 immune response through JNK1 and JNK2.

With the objective of inhibiting the JNK kinase pathway, WO/9849188 teaches the use of a human polypeptide, i.e. JNK-interacting protein I (JIP-1), which is a biological product and which has also been assayed for overcoming apoptosis related disorders. Although such human polypeptides have been confirmed to have an inhibitory effect onto the JNK kinase pathway, a whole variety of drawbacks are associated with their use:

Active bio peptides or bio-proteins are only obtained by means of rather comprehensive and expensive biosynthesis which consequently frequently renders the resulting products fairly cost-intensive.

The peptides are known to display poor membrane penetration and may not cross the blood brain membrane, The principal drawback to the use of peptide inhibitors or antagonists is the problem of low oral bioavailability resulting from intestinal degradation. Hence, they must be administered parenterally and finally, peptide inhibitors or antagonists are frequently viewed by the host body as intruding material to be eliminated, thus setting off an auto-immune response.

Hence, it is an objective of the present invention to provide relatively small molecules that avoid essentially all of the above-mentioned drawbacks arising from the use of peptides or proteins, however, which are suitable for the treatment of a variety of diseases, in particular of neuronal or the autoimmune system related disorders. It is notably an objective of the present invention to provide relatively small molecule chemical compounds which are able to modulate, preferably to down-regulate or to inhibit the JNK (Jun kinase) pathway so to be available as a convenient method of treating diseases which are preferably mediated by the JNK function. Moreover, it is an objective of the present invention to provide methods for preparing said small molecule chemical compounds. It is furthermore an objective of the present invention to provide a new category of pharmaceutical formulations for the treatment of diseases, preferably mediated by the INK function. It is finally an objective of the present invention to provide a method for the treatment and/or prevention of diseases that are caused by disorders of the autoimmune and/or the neuronal system.

DESCRIPTION OF THE INVENTION

The aforementioned objectives have been met according to the independent claims. Preferred embodiments are set out within the dependent claims which are incorporated herewith.

The following paragraphs provide definitions of the various chemical moieties and terms that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl; pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CHH$_2$), n-2-propenyl (allyl, —CH$_2$CH=CH$_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"Acyl" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbomyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens e.g. an —SO$_2$—CF$_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—CF$_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to S substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or "complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, nalic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quaternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as JunK2 and/or 3 inhibitors.

Quite surprisingly, it was now found that sulfonamide derivatives according to formula I are suitable pharmaceutically active agents, by effectively modulating, in particular by down-regulating inhibiting the action of JNK's, notably of JNK 2 and/or 3.

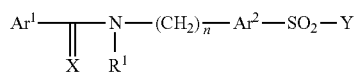

The compounds of formula I according to the present invention being suitable pharmaceutical agents are those wherein
$Ar^1$ and $Ar^2$ are independently from each other substituted or unsubstituted aryl or heteroaryl groups,
X is O or S, preferably O;
$R^1$ is hydrogen or a $C_1$-$C_6$-alkyl group, preferably H, or $R^1$ forms a substituted or unsubstituted 5-6-membered saturated or non-saturated ring with $Ar^1$;
n is an integer from 0 to 5, preferably between 1-3 and most preferred 1.
Y within formula I is an unsubstituted or a substituted 4-12-membered saturated cyclic or bicyclic alkyl containing at least one nitrogen atom, whereby one nitrogen atom within said ring is forming a bond with the sulfonyl group of formula I thus providing the sulfonamide.

In a preferred embodiment of the present invention, Y is a piperidine or piperazine moiety according to the below formula

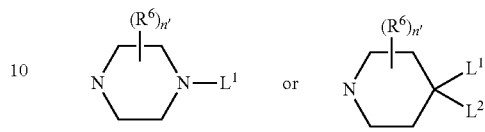

In said piperidine or piperazine groups, $L^1$ and $L^2$ are independently selected from each other from the group comprising or consisting of H, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted cyclic $C_4$-$C_8$-alkyl optionally containing 1-3 heteroatoms and optionally fused with aryl or heteroaryl; or $L^1$ and $L^2$ are independently selected from the group comprising or consisting of substituted or unsubstituted aryl, substituted or unsubstituted heteroaryl, aryl-$C_1$-$C_6$-alkyl, heteroaryl-$C_1$-$C_6$-alkyl, —C(O)—OR$^3$, —C(O)—R$^3$, —C(O)—NR$^{3'}$R$^3$, —NR$^{3'}$R$^3$, —NR$^{3'}$C(O)R$^3$, —NR$^{3'}$C(O)NR$^{3'}$R$^3$, —(SO)R$^3$, —(SO$_2$)R$^3$, —NSO$_2$R$^3$, —SO$_2$NR$^{3'}$R$^3$.

Thereby, $R^3$ and $R^{3'}$ are substituents independently selected from the group comprising or consisting of H, substituted or unsubstituted $C_1$-$C_6$-alkyl, substituted or unsubstituted $C_2$-$C_6$-alkenyl, substituted or unsubstituted aryl, substituted or unsubstituted heteroaryl, substituted or unsubstituted aryl-$C_1$-$C_6$-alkyl, substituted or unsubstituted heteroaryl-$C_1$-$C_6$-alkyl.

$R^6$ is selected from the group comprising or consisting of hydrogen, substituted or unsubstituted $C_1$-$C_6$-alkyl, substituted or unsubstituted $C_1$-$C_6$-alkoxy, OH, halogen, nitro, cyano, sulfonyl, oxo (=O), sulfoxy, acyloxy, thioalkoxy and n' is an integer from 0 to 4, preferably 1 or 2.

According to a further preferred embodiment of the present invention, Y is a pyrrolidine, an azepan or a 1,4-diazepan moiety of the below formulas

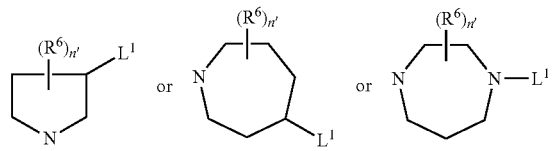

In said moieties, $L^1$ is selected from the group comprising or consisting of H, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted cyclic $C_4$-$C_8$-alkyl optionally containing 1-3 heteroatoms and optionally fused with aryl or heteroaryl; or $L^1$ and $L^2$ are independently selected from the group comprising or consisting of substituted or unsubstituted aryl, substituted or unsubstituted heteroaryl, aryl-$C_1$-$C_6$-alkyl, heteroaryl-$C_1$-$C_6$-alkyl, —C(O)—OR$^3$, —C(O)—R$^3$, —C(O)—NR$^{3'}$R$^3$, —NR$^{3'}$R$^3$, —NR$^{3'}$C(O)R$^3$, —NR$^{3'}$C(O)NR$^{3'}$R$^3$, —(SO)R$^3$, —(SO$_2$)R$^3$, —NSO$_2$R$^3$, —SO$_2$NR$^{3'}$R$^3$.

Thereby, $R^3$ and $R^{3'}$ are substituents independently selected from the group comprising or consisting of H, substituted or unsubstituted $C_1$-$C_6$-alkyl, substituted or unsubstituted $C_2$-$C_6$-alkenyl, substituted or unsubstituted aryl, substituted or unsubstituted heteroaryl, substituted or unsubstituted aryl-$C_1$-$C_6$-alkyl, substituted or unsubstituted heteroaryl-$C_1$-$C_6$-alkyl.

$R^6$ is selected from the group comprising or consisting of hydrogen, substituted or unsubstituted $C_1$-$C_6$-alkyl, substituted or unsubstituted $C_1$-$C_6$-alkoxy, OH, halogen, nitro, cyano, sulfonyl, oxo (=O), sulfoxy, acyloxy, thioalkoxy and n' is an integer from 0 to 4, preferably 0.

Most preferred azepan or a 1,4-diazepan moieties are those wherein, $L^1$ is —$NR^{3'}R^3$, with $R^3$ being hydrogen and $R^{3'}$ being a $C_1$-$C_{12}$, preferably $C_4$-$C_6$-alkyl which is optionally substituted with cycloalkyl, aryl or heteroaryl group.

All of the above mentioned aryl or heteroaryl groups could optionally be substituted by at least one of the groups selected from substituted or unsubstituted $C_1$-$C_6$-alkyl, like trihalomethyl, substituted or unsubstituted $C_1$-$C_6$-alkoxy, acyloxy, substituted or unsubstituted $C_2$-$C_6$-alkenyl, substituted or unsubstituted $C_2$-$C_6$-alkynyl, amino, acylamino, aminocarbonyl, $C_1$-$C_6$-alkoxycarbonyl, aryl, carboxyl, cyano, halogen, hydroxy, nitro, sulfonyl, sulfoxy, $C_1$-$C_6$-thioalkoxy.

Also $L^1$ and $L^2$ taken together could form a 4-8-membered saturated cyclic alkyl or heteroalkyl group, like triazolines, tetrazolines, oxazolines, isoxazolines, oxazoles or isoxazoles. In a preferred embodiment $L^1$ and $L^2$ form together 5-6-membered saturated cyclic alkyl ring containing 2-3 nitrogen atoms.

The present invention also includes the geometrical isomers, the optical active forms, enantiomers, diastereomers of compounds according to formula I, as well as their racemates and also pharmaceutically acceptable salts as well as the pharmaceutically active derivatives of the sulfonamide derivatives of formula I.

Preferred $Ar^1$ and $Ar^2$ in formula I are those that are independently selected from the group comprising or consisting of phenyl, thienyl, furanyl, pyridyl, optionally substituted by substituted or unsubstituted $C_1$-$C_6$-alkyl, like trihalomethyl, substituted or unsubstituted $C_1$-$C_6$-alkoxy, substituted or unsubstituted $C_2$-$C_6$-alkenyl, substituted or unsubstituted $C_2$-$C_6$-alkynyl, amino, acylamino, aminocarbonyl, $C_1$-$C_6$-alkoxycarbonyl, aryl, carboxyl, cyano, halo, hydroxy, nitro, sulfonyl, sulfoxy, acyloxy, $C_1$-$C_6$-thioalkoxy. The most preferred $Ar^1$ is a substituted phenyl, e.g. a 4-chlorophenyl, nitrophenyl, hydroxyphenyl, alkoxy phenyl, pyridyl, 3,4-dihydroxyphenyl, thioxo-dihydropyridine or its tautomer, pyrazole while the most preferred $Ar^2$ is an unsubstituted or substituted thienyl or furanyl group.

Where $Ar^1$ is a 4-chlorophenyl, nitrophenyl, hydroxyphenyl, alkoxy phenyl, pyridyl, 3,4-dihydroxyphenyl, thioxo-dihydropyridine or its tautomer, pyrazole group, X is preferably O, $R^1$ is hydrogen, n is 1 and $Ar^2$ is thienyl or furanyl.

A particularly preferred embodiment of the present invention is related to the sulfonamide derivatives, wherein Y is a substituted or unsubstituted piperidine residue,

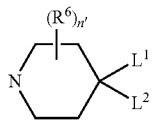

whereby $R^6$, n', $L^1$ and $L^2$ are as above defined.

In a more preferred embodiment of the sulfonamide derivatives according to formula I, $Ar^1$ is 4-chlorophenyl, X is O, $R^1$ is hydrogen, n is 1, $Ar^2$ is thienyl, Y is

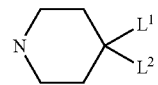

whereby $L^2$ is H and $L^1$ is a 5-membered cyclic group containing 3 heteroatoms, preferably a triazole ring, being preferably fused with a substituted or unsubstituted aryl group, e.g. a benzotriazole; or $L^2$ is —C(O)—$R^3$, or —$NHR^3$.

Thereby, $R^3$ is a substituent selected from the group comprising or consisting of substituted or unsubstituted aryl, substituted or unsubstituted heteroaryl, substituted or unsubstituted aryl-$C_1$-$C_6$-alkyl, substituted or unsubstituted heteroaryl-$C_1$-$C_6$-allyl.

Said aryl or heteroaryl groups may optionally be substituted by halogen, hydroxy, nitro, sulfonyl, e.g. a trifluoromethylsulfonyl group.

Specific examples of compounds of formula I include the following:

4-chloro-N-[5-(piperazine-1-sulfonyl)-thiophen-2-yl-methyl]-benzamide

4-Chloro-N-{5-[4-(3-Trifluoromethanesulfonyl-phenylamino)-piperidine-1-sulfonyl]-thiophen-2-ylmethyl}-benzamide 4-chloro-N-({5-[(4-pyridin-2-ylpiperazin-1-yl)sulfonyl]thien-2-yl}methyl)benzamide 4-chloro-N-[(5-{[4-(4-fluorobenzoyl)piperidin-1-yl]sulfonyl}thien-2-yl)methyl]-benzamide 4-chloro-N-{5-({4-[4-(trifluoromethyl)phenyl]piperazin-1-yl}sulfonyl)thien-2-yl]methyl}benzamide 4-chloro-N-({5-[(4-{2-nitrophenyl}piperazin-1-yl)sulfonyl]thien-2-yl}methyl)-benzamide 4-chloro-N-({5-[(4-{4-nitrophenyl}piperazin-1-yl)sulfonyl]thien-2-yl}methyl)-benzamide 4-chloro-N-[(5-{[4-(2-furoyl)piperazin-1-yl]sulfonyl}thien-2-yl)methyl]-benzamide 4-chloro-N-[(5-{[4-(4-hydroxyphenyl)piperazin-1-yl]sulfonyl}thien-2-yl)methyl]-benzamide 4-chloro-N-[(5-{[4-(2-oxo-2-pyrrolidin-1-ylethyl)piperazin-1-yl]sulfonyl}thien-2-yl)methyl]-benzamide 4-chloro-N-[(5-{[4-(2-morpholin-4-yl-2-oxoethyl)piperazin-1-yl]sulfonyl}thien-2-yl)methyl]benzamide 4-chloro-N-[(5-{[4-(pyridin-4-ylmethyl)piperazin-1-yl]sulfonyl}thien-2-yl)methyl]-benzamide 4-chloro-N-[(5-{[4-(2-thien-2-ylethyl)piperazin-1-yl]sulfonyl}thien-2-yl)methyl]-benzamide 4-chloro-N-[(5-{[4-(3,5-dimethoxyphenyl)piperazin-1-yl]sulfonyl}thien-2-yl)methyl]-benzamide 4-chloro-N-[(5-{[4-(cyclohexylmethyl)piperazin-1-yl]sulfonyl}thien-2-yl)methyl]-benzamide 4-chloro-N-[(5-{[4-(2-methoxyphenyl)piperazin-1-yl]sulfonyl}thien-2-yl)methyl]-benzamide N-({5-[(4-benzylpiperazin-1-yl)sulfonyl]thien-2-yl}methyl)-4-chlorobenzamide 4-chloro-N-[(5-{[4-(2-phenylethyl)piperazin-1-yl]sulfonyl}thien-2-yl)methyl]-benzamide 4-chloro-N-[(5-{[4-(4-fluorobenzyl)piperazin-1-yl]sulfonyl}thien-2-yl)methyl]-benzamide 4-chloro-N-[(5-{[4-(4-(2-cyanophenyl)piperazin-1-yl]sulfonyl}thien-2-yl)methyl]-benzamide 4-chloro-N-{[5-({4-[4-chloro-3-(trifluoromethyl)phenyl]piperazin-1-yl}sulfonyl)thien-2-yl]methyl}benzamide 4-chloro-N-[(5-{[4-(3-piperidin-1-ylpropyl)piperazin-1-yl]sulfonyl}thien-2-yl)methyl]-benzamide 4-chloro-N-({5-[(4-{4-chloro-2-nitrophenyl}piperazin-1-yl)sulfonyl]thien-2-yl}methyl)benzamide 4-chloro-N-[(5-{[4-(6-methylpyridin-2-yl)piperazin-1-yl]sulfonyl}thien-2-yl)methyl]-benzamide
4-chloro-N-({5-[(4-hydroxy-4-phenylpiperidin-1-yl)sulfonyl]thien-2-yl}methyl)-benzamide
N-({5-[(4-benzoylpiperidin-1-yl)sulfonyl]thien-2-yl}methyl)-4-chlorobenzamide
4-chloro-N-[(5-{[4-(2-oxo-2,3-dihydro-1H-benzimidazol-1-yl)piperidin-1-yl]sulfonyl}-thien-2-yl)methyl]benzamide
N-({5-[(4-benzylpiperidin-1-yl)sulfonyl]thien-2-yl}methyl)-4-chlorobenzamide
4-chloro-N-({5-[(4-oxo-1-phenyl-1,3,8-triazaspiro[4.5]dec-8-yl)sulfonyl]thien-2-yl}methyl)benzamide
4-chloro-N-{[5-({4-[2-(methylanilino)-2-oxoethyl]piperazin-1-yl}sulfonyl)thien-2-yl]methyl}benzamide
4-chloro-N-{[5-({4-[hydroxy(diphenyl)methyl]piperidin-1-yl}sulfonyl)thien-2-yl]methyl}benzamide
4-chloro-N-[(5-{[4-(3-cyanopyrazin-2-yl)piperazin-1-yl]sulfonyl}thien-2-yl)methyl]-benzamide
4-chloro-N-({5-[(4-{5-nitropyridin-2-yl}piperazin-1-yl)sulfonyl]thien-2-yl}methyl)-benzamide
4-chloro-N-{[5-({4-[3-chloro-5-(trifluoromethyl)pyridin-2-yl]piperazin-1-yl}sulfonyl)-thien-2-yl]methyl}benzamide
4-chloro-N-{[5-({4-[5-(trifluoromethyl)pyridin-2-yl]piperazin-1-yl}sulfonyl)thien-2-yl]methyl}benzamide
4-chloro-N-{[5-({4-[3-(trifluoromethyl)pyridin-2-yl]piperazin-1-yl}sulfonyl)thien-2-yl]methyl}benzamide
4-chloro-N-[(5-{[4-(2,4-difluorobenzoyl)piperidin-1-yl]sulfonyl}thien-2-yl)methyl]-benzamide
methyl 5-{4-[(5-{[(4-chlorobenzoyl)amino]methyl}thien-2-yl)sulfonyl]piperazin-1-yl}-7-(trifluoromethyl)thieno[3,2-b]pyridine-3-carboxylate
ethyl 2-{4-[(5-{[(4-chlorobenzoyl)amino]methyl}thien-2-yl)sulfonyl]piperazin-1-yl}-5-cyano-6-methylnicotinate
4-chloro-N-{[5-({4-[5-cyano-4,6-bis(dimethylamino)pyridin-2-yl]piperazin-1-yl}-sulfonyl)thien-2-yl]methyl}benzamide
4-chloro-N-{[5-({4-([6-methyl-2-(trifluoromethyl)quinolin-4-yl]piperazin-1-yl}sulfonyl)thien-2-yl]methyl}benzamide
tert-butyl 4-[(5-{[(4-chlorobenzoyl)amino]methyl}thien-2-yl)sulfonyl]piperazine-1-carboxylate
2-{4-[(5-{[(4-chlorobenzoyl)amino]methyl}thien-2-yl)sulfonyl]piperazin-1-yl}-8-ethyl-5-oxo-5,8-dihydropyrido[2,3-d]pyrimidine-6-carboxylic acid
7-{4-[(5-{[(4-chlorobenzoyl)amino]methyl}thien-2-yl)sulfonyl]piperazin-1-yl}-1-ethyl-6-fluoro-4-oxo-1,4-dihydro[1,8]naphthyridine-3-carboxylic acid
7-{4-[(5-{[(4-chlorobenzoyl)amino]methyl}thien-2-yl)sulfonyl]piperazin-1-yl}-1-ethyl-6-fluoro-4-oxo-1,4-dihydroquinoline-3-carboxylic acid
4-chloro-N-[(5-{[4-(2,3-dihydro-1,4-benzodioxin-2-ylcarbonyl)piperazin-1-yl]sulfonyl}thien-2-yl)methyl]benzamide
4-chloro-N-{[5-({4-[(2E)-3-phenylprop-2-enyl]piperazin-1-yl}sulfonyl)thien-2-yl]-methyl}benzamide
4-chloro-N-[(5-{[4-(3-phenylpropyl)piperazin-1-yl]sulfonyl}thien-2-yl)methyl]-benzamide
4-chloro-N-[(5-{[4-(3,4,5-trimethoxyphenyl)piperazin-1-yl]sulfonyl}thien-2-yl)-methyl]-benzamide
N-[(5-{[4-(4-tert-butylbenzyl)piperazin-1-yl]sulfonyl}thien-2-yl)methyl]-4-chloro-benzamide
4-chloro-N-[(5-{[4-(4-fluorophenyl)piperazin-1-yl]sulfonyl}thien-2-yl)methyl]-benzamide
4-chloro-N-{[5-{[4-(2-hydroxyphenyl)piperazin-1-yl]sulfonyl}thien-2-yl)methyl]-benzamide
4-chloro-N-{[5-({4-[4-(trifluoromethyl)pyridin-2-yl]piperazin-1-yl}sulfonyl)thien-2-yl]methyl}benzamide
4-chloro-N-[(5-{[4-(5-cyanopyridin-2-yl)piperazin-1-yl]sulfonyl}thien-2-yl)methyl]-benzamide
tert-butyl 1-[(5-{[(4-chlorobenzoyl)amino]methyl}thien-2-yl)sulfonyl]piperidin-4-ylcarbamate
4-chloro-N-({5-[(4-phenylpiperazin-1-yl)sulfonyl]thien-2-yl}methyl)benzamide
4-chloro-N-{[5-(piperidin-1-ylsulfonyl)thien-2-yl]methyl}benzamide
4-chloro-N-[(5-{[4-(1-naphthyl)piperazin-1-yl]sulfonyl}thien-2-yl)methyl]benzamide
4-chloro-N-[(5-{[4-(3,4-dichlorophenyl)piperazin-1-yl]sulfonyl}thien-2-yl)methyl]-benzamide
4-chloro-N-{[5-({4-[3-(trifluoromethyl)phenyl]piperazin-1-yl}sulfonyl)thien-2-yl]methyl}benzamide
4-chloro-N-{[5-({3-hydroxy-4-[3-(trifluoromethyl)phenyl]piperidin-1-yl}sulfonyl)-thien-2-yl]methyl}benzamide
4-chloro-N-[(5-{[4-(2-methylphenyl)piperazin-1-yl]sulfonyl}thien-2-yl)methyl]-benzamide
N-[(5-{[(1R,4R)-5-benzyl-2,5-diazabicyclo[2.2.1]hept-2-yl]sulfonyl}thien-2-yl)methyl]-4-chlorobenzamide
N-[(5-{[4-(benzyloxy)piperidin-1-yl]sulfonyl}thien-2-yl)methyl]-4-chlorobenzamide
4-chloro-N-[(5-{[4-(2-chlorodibenzo[b,f][1,4]oxazepin-11-yl)piperazin-1-yl]sulfonyl}-thien-2-yl)methyl]benzamide
N-(4-chlorophenyl)-2-(5-{[4-(2-oxo-2,3-dihydro-1H-benzimidazol-1-yl)piperidin-1-yl]sulfonyl}thien-2-yl)acetamide
4-chloro-N-({5-[(4-hydroxypiperidin-1-yl)sulfonyl]thien-2-yl}methyl)benzamide
N-[(5-{[4-(4-acetylphenyl)piperazin-1-yl]sulfonyl}thien-2-yl)methyl]-4-chloro-benzamide
4-chloro-N-[(5-{[4-(3,5-dichloropyridin-4-yl)piperazin-1-yl]sulfonyl}thien-2-yl)methyl]benzamide
4-chloro-N-[(5-{[4-(3-methoxyphenyl)piperazin-1-yl]sulfonyl}thien-2-yl)methyl]-benzamide
N-({5-[(4-benzyl-4-hydroxypiperidin-1-yl)sulfonyl]thien-2-yl}methyl)-4-chloro-benzamide
N-{[5-({4-[(2-tert-butyl-1H-indol-5-yl)amino]piperidin-1-yl}sulfonyl)thien-2-yl]methyl}-4-chlorobenzamide
4-chloro-N-{[5-({4-[(phenylacetyl)amino]piperidin-1-yl}sulfonyl)thien-2-yl]-methyl}benzamide
4-chloro-N-[(5-{[4-(tetrahydrofuran-2-ylcarbonyl)piperazin-1-yl]sulfonyl}thien-2-yl)methyl]benzamide
4-chloro-N-[(5-{[4-(6-chloropyridin-2-yl)piperazin-1-yl]sulfonyl}thien-2-yl)methyl]-benzamide
4-chloro-N-[(5-{[4-(4-chlorophenyl)piperazin-1-yl]sulfonyl}thien-2-yl)methyl]-benzamide
N-[(5-{[4-(2H-1,2,3-benzotriazol-2-yl)piperidin-1-yl]sulfonyl}thien-2-yl)methyl]-4-chlorobenzamide
4-chloro-N-[(5-{[4-(4-chlorobenzoyl)piperidin-1-yl]sulfonyl}thien-2-yl)methyl]-benzamide
4-chloro-N-({5-[(4-phenoxypiperidin-1-yl)sulfonyl]thien-2-yl}methyl)benzamide
N-{[5-({4-[benzyl(methyl)amino]piperidin-1-yl}sulfonyl)thien-2-yl]methyl}-4-chlorobenzamide
4-chloro-N-{[5-({4-[3-(2,4-dichlorophenyl)-1H-pyrazol-5-yl]piperidin-1-yl}sulfonyl)-thien-2-yl]methyl}benzamide
4-chloro-N-[(5-{[4-(5-thien-2-yl-1H-pyrazol-3-yl)piperidin-1-yl]sulfonyl}thien-2-yl)methyl]benzamide
4-chloro-N-[(5-{[4-(2,3,4,5,6-pentamethylbenzoyl)piperidin-1-yl]sulfonyl}thien-2-yl)methyl]benzamide
4-chloro-N-[(5-{[4-(phenylacetyl)-1,4-diazepan-1-yl]sulfonyl}thien-2-yl)methyl]benzamide
4-chloro-N-{[5-({4-[5-(4-methoxyphenyl)-1H-pyrazol-3-yl]piperidin-1-yl}sulfonyl)-thien-2-yl]methyl}benzamide N-({5-[(4-anilinopiperidin-1-yl)sulfonyl]thien-2-yl}methyl)-4-chlorobenzamide
4-chloro-N-[(5-{[4-(3-phenyl-1,2,4-thiadiazol-5-yl)piperazin-1-yl]sulfonyl}thien-2-yl)methyl]benzamide
4-chloro-N-[(5-{[4-(2-phenylethyl)piperidin-1-yl]sulfonyl}thien-2-yl)methyl]-benzamide
4-chloro-N-({5-[(4-heptylpiperazin-1-yl)sulfonyl]thien-2-yl}methyl)benzamide
4-chloro-N-({5-[(4-octylpiperazin-1-yl)sulfonyl]thien-2-yl}methyl)benzamide
N-[(5-{[4-(1H-1,2,3-benzotriazol-1-yl)piperidin-1-yl]sulfonyl}thien-2-yl)methyl]-4-chlorobenzamide
2-(5-{[4-(1H-1,2,3-benzotriazol-1-yl)piperidin-1-yl]sulfonyl}thien-2-yl)-N-(4-chloro-phenyl)acetamide
2-{1-[(5-{[(4-chlorobenzoyl)amino]methyl}thien-2-yl)sulfonyl]piperidin-4-yl}-2H-1,2,3-benzotriazole-5-carboxylic
4-chloro-N-[(5-{[4-(5-chloro-1H-1,2,3-benzotriazol-1-yl)piperidin-1-yl]sulfonyl}thien-2-yl)methyl]benzamide
methyl 1-{1-[(5-{[(4-chlorobenzoyl)amino]methyl}thien-2-yl)sulfonyl]piperidin-4-yl}-1H-1,2,3-benzotriazole-5-carboxylate
methyl 1-{1-[(5-{[(4-chlorobenzoyl)amino]methyl}thien-2-yl)sulfonyl]piperidin-4-yl}-1H-1,2,3-benzotriazole-6-carboxylate
methyl 2-{1-[(5-{[(4-chlorobenzoyl)amino]methyl}thien-2-yl)sulfonyl]piperidin-4-yl}-2H-1,2,3-benzotriazole-5-carboxylate
4-chloro-N-[(5-{[4-(6-chloro-1H-1,2,3-benzotriazol-1-yl)piperidin-1-yl]sulfonyl}thien-2-yl)methyl]benzamide
4-chloro-N-{[5-({4-[5-(trifluoromethyl)-1H-1,2,3-benzotriazol-1-yl]piperidin-1-yl}-sulfonyl)thien-2-yl]methyl}benzamide
N-[(5-{[4-(7-aza-1H-benzimidazol-1-yl)piperidin-1-yl]sulfonyl}thien-2-yl)methyl]-4-chlorobenzamide
1-{1-[(5-{[(4-chlorobenzoyl)amino]methyl}thien-2-yl)sulfonyl]piperidin-4-yl}-1H-1,2,3-benzotriazole-5-carboxylic
1-{1-[(5-{[(4-chlorobenzoyl)amino]methyl}thien-2-yl)sulfonyl]piperidin-4-yl}-1H-1,2,3-benzotriazole-6-carboxylic
N-(5-{[4-(2-amino-9H-purin-9-yl)piperidin-1-yl]sulfonyl}thien-2-yl)methyl]-4-chlorobenzamide
4-chloro-N-[(5-{[4-(9H-purin-9-yl)piperidin-1-yl]sulfonyl}thien-2-yl)methyl]-benzamide
N-[(5-{[4-(6-amino-9H-purin-9-yl)piperidin-1-yl]sulfonyl}thien-2-yl)methyl]-4-chlorobenzamide
4-chloro-N-({5-[(4-{6-nitro-1H-benzimidazol-1-yl}piperidin-1-yl)sulfonyl]thien-2-yl}methyl)benzamide
4-chloro-N-({5-[(4-{5-nitro-1H-benzimidazol-1-yl}piperidin-1-yl)sulfonyl]thien-2-yl}methyl)benzamide
4-chloro-N-[(5-{[4-(2H-1,2,3-triazol-2-yl)piperidin-1-yl]sulfonyl}thien-2-yl)methyl]-benzamide
N-[(5-{[4-(1H-benzimidazol-1-yl)piperidin-1-yl]sulfonyl}thien-2-yl)methyl]-4-chlorobenzamide
4-chloro-N-{[5-({4-[3-propylanilino]piperidin-1-yl}sulfonyl)thien-2-yl]methyl}-benzamide
4-chloro-N-{[5-({4-[3-(trifluoromethyl)anilino]piperidin-1-yl}sulfonyl)thien-2-yl]methyl}benzamide
4-chloro-N-{[5-({4-[3-(dimethylamino)anilino]piperidin-1-yl}sulfonyl)thien-2-yl]methyl}benzamide
methyl
4-chloro-N-{[5-({4-[3-(methylsulfanyl)anilino]piperidin-1-yl}sulfonyl)thien-2-yl]methyl}benzamide
4-chloro-N-({5-[(4-{3-nitroanilino}piperidin-1-yl)sulfonyl]thien-2-yl}methyl)-benzamide
4-chloro-N-[(5-{[4-(2-methoxyanilino)piperidin-1-yl]sulfonyl}thien-2-yl)methyl]-benzamide
3-({1-[(5-{[(4-chlorobenzoyl)amino]methyl}thien-2-yl)sulfonyl]piperidin-4-yl}amino)benzamide
4-chloro-N-{[5-({4-[2-(trifluoromethyl)anilino]piperidin-1-yl}sulfonyl)thien-2-yl]methyl}benzamide
4-chloro-N-({5-[(4-{2-nitro-4-[(trifluoromethyl)sulfonyl]anilino}piperidin-1-yl)sulfonyl]thien-2-yl}methyl)benzamide
4-chloro-N-[(5-{[4-(4-chloroanilino)piperidin-1-yl]sulfonyl}thien-2-yl)methyl]-benzamide
4-chloro-N-{[5-({4-[4-(trifluoromethyl)anilino]piperidin-1-yl}sulfonyl)thien-2-yl]-methyl}benzamide
4-chloro-N-({5-[(4-{4-[(trifluoromethyl)sulfonyl]anilino}piperidin-1-yl)sulfonyl]thien-2-yl}methyl)benzamide
4-chloro-N-({5-[(4-{2-nitroanilino}piperidin-1-yl)sulfonyl]thien-2-yl}methyl)-benzamide
N-{[5-({4-[4-(aminocarbonyl)anilino]piperidin-1-yl}sulfonyl)thien-2-yl]methyl}-4-chlorobenzamide
4-chloro-N-{[5-({4-[4-(1,3-dithiolan-2-yl)anilino]piperidin-1-yl}sulfonyl)thien-2-yl]methyl}benzamide
N-[(5-{[4-(3-chloroanilino)piperidin-1-yl]sulfonyl}thien-2-yl)methyl]-3-nitrobenzamide
4-chloro-N-[(5-{[4-(3-chloroanilino)piperidin-1-yl]sulfonyl}thien-2-yl)methyl]-benzamide
4-chloro-N-[(5-{[4-(3-methoxyanilino)piperidin-1-yl]sulfonyl}thien-2-yl)methyl]-benzamide
4-chloro-N-{[5-({4-[3-(methylsulfonyl)anilino]piperidin-1-yl}sulfonyl)thien-2-yl]methyl}benzamide
N-({5-[(4-{3-[amino(imino)methyl]anilino}piperidin-1-yl)sulfonyl]thien-2-yl}methyl)-4-chlorobenzamide
4-chloro-N-({5-[(4-{3-[(2-hydroxyethyl)sulfonyl]anilino}piperidin-1-yl)sulfonyl]thien-2-yl}methyl)benzamide
N-[(5-{[4-(2-aminoanilino)piperidin-1-yl]sulfonyl}thien-2-yl)methyl]-4-chlorobenzamide
4-chloro-N-[(5-{[4-(2-hydroxyanilino)piperidin-1-yl]sulfonyl}thien-2-yl)methyl]-benzamide
4-chloro-N-[(5-{[4-(4-hydroxyanilino)piperidin-1-yl]sulfonyl}thien-2-yl)methyl]-benzamide
4-chloro-N-({5-[(4-{3-[(trifluoromethyl)sulfanyl]anilino}piperidin-1-yl)sulfonyl]thien-2-yl}methyl)benzamide
4-chloro-N-[(5-{[4-(3-toluidino)piperidin-1-yl]sulfonyl}thien-2-yl)methyl]benzamide
4-chloro-N-({5-[(4-{[3-chloro-5-(trifluoromethyl)pyridin-2-yl]amino}piperidin-1-yl)sulfonyl]thien-2-yl}methyl)benzamide
4-chloro-N-{[5-({4-[3-(1,3-oxazol-5-yl)anilino]piperidin-1-yl}sulfonyl)thien-2-yl]methyl}benzamide
N-[(5-{[4-(3-tert-butylanilino)piperidin-1-yl]sulfonyl}thien-2-yl)methyl]-4-chlorobenzamide
4-chloro-N-[(5-{[4-(2-propylanilino)piperidin-1-yl]sulfonyl}thien-2-yl)methyl]-benzamide
4-chloro-N-{[5-({4-[(2,2-dioxido-1,3-dihydro-2-benzothien-5-yl)amino]piperidin-1-yl}sulfonyl)thien-2-yl]methyl}benzamide
4-chloro-N-[(5-{[4-(2,3-dihydro-1H-inden-5-ylamino)piperidin-1-yl]sulfonyl}thien-2-yl)methyl]benzamide
4-chloro-N-[(5-{[4-(4-propylanilino)piperidin-1-yl]sulfonyl}thien-2-yl)methyl]-benzamide
4-chloro-N-[(5-{[4-({3-nitropyridin-2-yl}amino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-4-chlorobenzamide N-[(5-{[4-([1,1'-biphenyl]-3-ylamino)piperidin-1-yl]
  sulfonyl}thien-2-yl)methyl]-4-chlorobenzamide
N-[(5-{[4-(3-benzylanilino)piperidin-1-yl]sulfonyl}thien-2-
  yl)methyl]-4-chlorobenzamide
4-chloro-N-[(5-{[4-(pyrimidin-2-ylamino)piperidin-1-yl]
  sulfonyl}thien-2-yl)methyl]-benzamide
4-chloro-N-{[5-({4-[4-(morpholin-4-ylsulfonyl)anilino]pip-
  eridin-1-yl}sulfonyl)thien-2-yl]methyl}benzamide
4-chloro-N-({5-[(4-{[4-(trifluoromethyl)pyrimidin-2-yl]
  amino}piperidin-1-yl)sulfonyl]-thien-2-yl}methyl)benza-
  mide
4-chloro-N-[(5-{[4-(3-cyclohexyl-4-hydroxyanilino)piperi-
  din-1-yl]sulfonyl}thien-2-yl)methyl]benzamide
N-({5-[(4-{3-[(butylamino)sulfonyl]anilino}piperidin-1-yl)
  sulfonyl]thien-2-yl}methyl)-4-chlorobenzamide
4-chloro-N-[(5-{[4-(3-ethylanilino)piperidin-1-yl]
  sulfonyl}thien-2-yl)methyl]-benzamide
4-chloro-N-[(5-{[4-(5,6,7,8-tetrahydronaphthalen-1-
  ylamino)piperidin-1-yl]sulfonyl}-thien-2-yl)methyl]ben-
  zamide
N-{[5-({4-[3-(aminosulfonyl)anilino]piperidin-1-
  yl}sulfonyl)thien-2-yl]methyl}-4-chlorobenzamide
4-chloro-N-[(5-{[4-(quinolin-5-ylamino)piperidin-1-yl]
  sulfonyl}thien-2-yl)methyl]-benzamide
4-chloro-N-[(5-{[4-(quinolin-8-ylamino)piperidin-1-yl]
  sulfonyl}thien-2-yl)methyl]-benzamide
4-Chloro-N-[(5-{[4-(3-propylphenoxy)piperidin-1-yl]
  sulfonyl}thien-2-yl)methyl]-benzamide
4-chloro-N-{[5-({4-[(2E)-3-phenylprop-2-enoyl]piperazin-
  1-yl}sulfonyl)thien-2-yl]methyl}benzamide
4-chloro-N-({5-[(4-{4-nitrobenzoyl}piperazin-1-yl)sulfo-
  nyl]thien-2-yl}methyl)-benzamide
N-({5-[(4-benzoylpiperazin-1-yl)sulfonyl]thien-2-
  yl}methyl)-4-chlorobenzamide
4-chloro-N-{[5-({4-[4-(trifluoromethyl)benzoyl]piperazin-
  1-yl}sulfonyl)thien-2-yl]methyl}benzamide
4-chloro-N-{[5-({4-[4-(dimethylamino)benzoyl]piperazin-
  1-yl}sulfonyl)thien-2-yl]methyl}benzamide
4-chloro-N-[(5-{[4-(2-fluorobenzoyl)piperazin-1-yl]
  sulfonyl}thien-2-yl)methyl]-benzamide
4-chloro-N-[(5-{[4-(2,6-difluorobenzoyl)piperazin-1-yl]
  sulfonyl}thien-2-yl)methyl]-benzamide
4-chloro-N-[(5-{[4-(3-fluorobenzoyl)piperazin-1-yl]
  sulfonyl}thien-2-yl)methyl]-benzamide
4-chloro-N-[(5-{[4-(2-naphthoyl)piperazin-1-yl]
  sulfonyl}thien-2-yl)methyl]benzamide
4-chloro-N-[(5-{[4]-(1-naphthoyl)piperazin-1-yl]
  sulfonyl}thien-2-yl)methyl]benzamide
4-chloro-N-({5-[(4-{2-nitrobenzoyl}piperazin-1-yl)sulfo-
  nyl]thien-2-yl}methyl)-benzamide
4-chloro-N-[(5-{[4-(pyridin-3-ylcarbonyl)piperazin-1-yl]
  sulfonyl}thien-2-yl)methyl]-benzamide
N-[(5-{[4-(2,1,3-benzoxadiazol-5-ylcarbonyl)piperazin-1-
  yl]sulfonyl}thien-2-yl)methyl]-4-chlorobenzamide
4-chloro-N-[(5-{[4-(2,4-difluorobenzoyl)piperazin-1-yl]
  sulfonyl}thien-2-yl)methyl]-benzamide
4-chloro-N-[(5-{[4(2,4,6-trifluorobenzoyl)piperazin-1-yl]
  sulfonyl}thien-2-yl)methyl]-benzamide
4-chloro-N-[(5-{[4-(2,6-dichlorobenzoyl)piperazin-1-yl]
  sulfonyl}thien-2-yl)methyl]-benzamide
4-chloro-N-({5-[(4-heptanoylpiperazin-1-yl)sulfonyl]thien-
  2-yl}methyl)benzamide
4-chloro-N-[(5-{[4-(quinolin-8-ylsulfonyl)piperazin-1-yl]
  sulfonyl}thien-2-yl)methyl]-benzamide
4-nitro-N-({5-[(4-{3-[(trifluoromethyl)sulfonyl]
  anilino}piperidin-1-yl)sulfonyl]thien-2-yl}methyl)benza-
  mide
N-[(5-{[4-(1H-1,2,3-benzotriazol-1-yl)piperidin-1-yl]
  sulfonyl}thien-2-yl)methyl]-3-nitrobenzamide
4-nitro-N-({5-[(4-{3-[(trifluoromethyl)sulfonyl]
  anilino}piperidin-1-yl)sulfonyl]thien-2-yl}methyl)benza-
  mide
N-[(5-{[4-(2,4-difluorobenzoyl)piperidin-1-yl]
  sulfonyl}thien-2-yl)methyl]-4-nitrobenzamide
N-[(5-{[4-(1H-1,2,3-benzotriazol-1-yl)piperidin-1-yl]
  sulfonyl}thien-2-yl)methyl]-4-nitrobenzamide
N-[(5-{[4-(1H-1,2,3-benzotriazol-1-yl)piperidin-1-yl]
  sulfonyl}thien-2-yl)methyl]-3-nitrobenzamide
4-nitro-N-({5-[(4-{3-[(trifluoromethyl)sulfonyl]
  anilino}piperidin-1-yl)sulfonyl]thien-2-yl}methyl)benza-
  mide
N-[(5-{[4-(2,4-difluorobenzoyl)piperidin-1-yl]
  sulfonyl}thien-2-yl)methyl]-4-nitrobenzamide
N-[(5-{[4-(1H-1,2,3-benzotriazol-1-yl)piperidin-1-yl]
  sulfonyl}thien-2-yl)methyl]-4-nitrobenzamide
3-nitro-N-[(5-{[4-(3-methoxyanilino)piperidin-1-yl]
  sulfonyl}thien-2-yl)methyl]-benzamide
3-nitro-N-{[5-({4-[3-(trifluoromethyl)anilino]piperidin-1-
  yl}sulfonyl)thien-2-yl]-methyl}benzamide
N-{[5-({4-[3-(dimethylamino)anilino]piperidin-1-
  yl}sulfonyl)thien-2-yl]methyl}-3-nitrobenzamide
3-nitro-N-{[5-({4-[3-(methylsulfonyl)anilino]piperidin-1-
  yl}sulfonyl)thien-2-yl]-methyl}benzamide
3-nitro-N-{[5-({4-[3-(methylsulfanyl)anilino]piperidin-1-
  yl}sulfonyl)thien-2-yl]-methyl}benzamide
N-{[5-({4-[3-(aminosulfonyl)anilino]piperidin-1-
  yl}sulfonyl)thien-2-yl]methyl}-3-nitrobenzamide
methyl
N-{[5-({4-[3-(aminocarbonyl)anilino]piperidin-1-
  yl}sulfonyl)thien-2-yl]methyl}-3-nitrobenzamide
3-nitro-N-({5-[(4-{3-nitroanilino}piperidin-1-yl)sulfonyl]
  thien-2-yl}methyl)benzamide
3-nitro-N-[(5-{[4-(2-methoxyanilino)piperidin-1-yl]
  sulfonyl}thien-2-yl)methyl]-benzamide
3-nitro-N-{[5-({4-[2-(trifluoromethyl)anilino]piperidin-1-
  yl}sulfonyl)thien-2-yl]-methyl}benzamide
3-nitro-N-({5-[(4-{2-nitroanilino}piperidin-1-yl)sulfonyl]
  thien-2-yl}methylbenzamide
N-[(5-{[4-(4-chloroanilino)piperidin-1-yl]sulfonyl}thien-2-
  yl)methyl]-3-nitrobenzamide
3-nitro-N-{[5-({4-[4-(trifluoromethyl)anilino]piperidin-1-
  yl}sulfonyl)thien-2-yl]-methyl}benzamide
3-nitro-N-({5-[(4-{4-[(trifluoromethyl)sulfonyl]
  anilino}piperidin-1-yl)sulfonyl]thien-2-yl}methyl)benza-
  mide
N-{[5-({4-[4-(aminocarbonyl)anilino]piperidin-1-
  yl}sulfonyl)thien-2-yl]methyl}-3-nitrobenzamide
N-[(5-{[4-(3-propylanilino)piperidin-1-yl]sulfonyl}thien-2-
  yl)methyl]-3-nitrobenzamide
N-[(5-{[4-(3-chloroanilino)piperidin-1-yl]sulfonyl}thien-2-
  yl)methyl]-4-nitrobenzamide
4-nitro-N-[(5-{[4-(3-methoxyanilino)piperidin-1-yl]
  sulfonyl}thien-2-yl)methyl]-benzamide
4-nitro-N-{([5-({4-[3-(trifluoromethyl)anilino)piperidin-]-
  yl}sulfonyl)thien-2-yl]-methyl}benzamide
N-{[5-({4-[3-(dimethylamino)anilino]piperidin-1-
  yl}sulfonyl)thien-2-yl]methyl}-4-nitrobenzamide
4-nitro-N-[(5-{[4-(3-propylanilino)piperidin-1-yl]
  sulfonyl}thien-2-yl)methyl]-benzamide
4-nitro-N-{[5-({4-[3-(methylsulfonyl)anilino]piperidin-1-
  yl}sulfonyl)thien-2-yl]methyl}benzamide
4-nitro-N-{[5-({4-[3-(methylsulfanyl)anilino]piperidin-1-
  yl}sulfonyl)thien-2-yl]methyl}benzamide N-{[5-({4-[3-(aminosulfonyl)anilino]piperidin-1-yl}sulfonyl)thien-2-yl]methyl}-4-nitrobenzamide
methyl 3-{[1-({5-[({4-nitrobenzoyl}amino)methyl]thien-2-yl}sulfonyl)piperidin-4-yl]amino}-benzamide
4-nitro-N-({5-[(4-{3-nitroanilino}piperidin-1-yl)sulfonyl]thien-2-yl}methyl)benzamide
4-nitro-N-[(5-{[4-(2-methoxyanilino)piperidin-1-yl]sulfonyl}thien-2-yl)methyl]-benzamide
4-nitro-N-{[5-({4-[2-(trifluoromethyl)anilino]piperidin-1-yl}sulfonyl)thien-2-yl]-methyl}benzamide
4-nitro-N-({5-[(4-{2-nitroanilino}piperidin-1-yl)sulfonyl]thien-2-yl}methyl)benzamide
N-[(5-{[4-(4-chloroanilino)piperidin-1-yl]sulfonyl}thien-2-yl)methyl]-4-nitrobenzamide
4-nitro-N-{[5-({4-[4-(trifluoromethyl)anilino]piperidin-1-yl}sulfonyl)thien-2-yl]-methyl}benzamide
4-nitro-N-({5-[(4-{4-[(trifluoromethyl)sulfonyl]anilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-4-nitrobenzamide
N-{[5-({4-[4-(1,3-dithiolan-2-yl)anilino]piperidin-1-yl}sulfonyl)thien-2-yl]methyl}-4-nitrobenzamide
N-({5-[(4-{3-[amino(imino)methyl]anilino}piperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}-methyl)-3-nitrobenzamide
N-({5-[(4-anilinopiperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}methyl)-4-nitrobenzamide
N-({5-[(4-anilinopiperidin-1-yl)sulfonyl]thien-2-yl}methyl)-4-nitrobenzamide
N-({5-[(4-{3-[amino(imino)methyl]anilino}piperidin-1-yl)sulfonyl]thien-2-yl}methyl)-4-nitrobenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
3-nitro-N-[(5-{[4-({3-nitropyridin-2-yl}amino)piperidin-1-yl]sulfonyl}thien-2-yl)-methyl]benzamide
N-{[5-({4-[(2,2-dioxido-1,3-dihydro-2-benzothien-5-yl)amino]piperidin-1-yl}-sulfonyl)thien-2-yl]methyl}-3-nitrobenzamide
N-[(5-{[4-(2,3-dihydro-1H-inden-5-ylamino)piperidin-1-yl]sulfonyl}thien-2-yl)-methyl]-3-nitrobenzamide
3-nitro-N-[(5-{[4-(2-propylanilino)piperidin-1-yl]sulfonyl}thien-2-yl)methyl]-benzamide
3-nitro-N-[(5-{[4-(4-propylanilino)piperidin-1-yl]sulfonyl}thien-2-yl)methyl]-benzamide
N-[(5-{[4-(3-tert-butylanilino)piperidin-1-yl]sulfonyl}thien-2-yl)methyl]-3-nitrobenzamide
3-nitro-N-{[5-({4-[3-(1,3-oxazol-5-yl)anilino]piperidin-1-yl}sulfonyl)thien-2-yl]methyl}benzamide
3-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]-thien-2-yl}methyl)-3-nitrobenzamide
N-[(5-{[4-([1,1'-biphenyl]-3-ylamino)piperidin-1-yl]sulfonyl}thien-2-yl)methyl]-3-nitrobenzamide
N-[(5-{[4-(3-benzylanilino)piperidin-1-yl]sulfonyl}thien-2-yl)methyl]-3-nitrobenzamide
3-nitro-N-{[5-({4-[3-(morpholin-4-ylsulfonyl)anilino]piperidin-1-yl}sulfonyl)thien-2-yl]methyl}benzamide
3-nitro-N-[(5-{[4-(3-propylphenoxy)piperidin-1-yl]sulfonyl}thien-2-yl)methyl]benzamide
4-nitro-N-[(5-{[4-(pyrimidin-2-ylamino)piperidin-1-yl]sulfonyl}thien-2-yl)methyl]-benzamide
N-{[5-({4-[(3-aminopyridin-2-yl)amino]piperidin-1-yl}sulfonyl)thien-2-yl]methyl}-4-nitrobenzamide
4-nitro-N-[(5-{[4-({3-nitropyridin-2-yl}amino)piperidin-1-yl]sulfonyl}thien-2-yl)-methyl]benzamide
N-[(5-{[4-(2,3-dihydro-1H-inden-5-ylamino)piperidin-1-yl]sulfonyl}thien-2-yl)-methyl]-4-nitrobenzamide
4-nitro-N-[(5-{[4-(2-propylanilino)piperidin-1-yl]sulfonyl}thien-2-yl)methyl]-benzamide
4-nitro-N-[(5-{[4-(4-propylanilino)piperidin-1-yl]sulfonyl}thien-2-yl)methyl]-benzamide
N-[(5-{[4-(3-tert-butylanilino)piperidin-1-yl]sulfonyl}thien-2-yl)methyl]-4-nitrobenzamide
4-nitro-N-{[5-({4-[3-(1,3-oxazol-5-yl)anilino]piperidin-1-yl}sulfonyl)thien-2-yl]-methyl}benzamide
4-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]-thien-2-yl}methyl)-4-nitrobenzamide
N-[(5-{[4-([1,1'-biphenyl]-3-ylamino)piperidin-1-yl]sulfonyl}thien-2-yl)methyl]-4-nitrobenzamide
N-[(5-{([4-(3-benzylanilino)piperidin-1-yl]sulfonyl}thien-2-yl)methyl]-4-nitrobenzamide
4-nitro-N-{[5-({4-[3-(morpholin-4-ylsulfonyl)anilino]piperidin-1-yl}sulfonyl)thien-2-yl]methyl}benzamide
N-[(5-{[4-(2-aminoanilino)piperidin-1-yl]sulfonyl}thien-2-yl)methyl]-3-nitrobenzamide
3-nitro-N-[(5-{[4-(pyrimidin-2-ylamino)piperidin-1-yl]sulfonyl}thien-2-yl)methyl]-benzamide
N-{[5-({4-[(3-aminopyridin-2-yl)amino]piperidin-1-yl}sulfonyl)thien-2-yl]methyl}-3-nitrobenzamide
N-({5-[(4-{2-nitro-4-[(trifluoromethyl)sulfonyl]anilino}piperidin-1-yl)sulfonyl]thien-2-yl}methyl)-3-methoxybenzamide
3-nitro-N-[(5-{[4-(3-phenylpropyl)piperazin-1-yl]sulfonyl}thien-2-yl)methyl]-benzamide
3-nitro-N-({5-[(4-{[4-(trifluoromethyl)pyrimidin-2-yl]amino}piperidin-1-yl)sulfonyl]-thien-2-yl}methyl)benzamide
N-[(5-{[4-(3-cyclohexyl-4-hydroxyanilino)piperidin-1-yl]sulfonyl}thien-2-yl)methyl]-3-nitrobenzamide
N-({5-[(4-{3-[(butylamino)sulfonyl]anilino}piperidin-1-yl)sulfonyl]thien-2-yl}methyl)-3-nitrobenzamide
N-[(5-{[4-(3-ethylanilino)piperidin-1-yl]sulfonyl}thien-2-yl)methyl]-3-nitrobenzamide
3-nitro-N-[(5-{[4-(5,6,7,8-tetrahydronaphthalen-1-ylamino)piperidin-1-yl]sulfonyl}-thien-2-yl)methyl]benzamide
4-nitro-N-[(5-{[4-(3-propylphenoxy)piperidin-1-yl]sulfonyl}thien-2-yl)methyl]-benzamide
N-[(5-{[4-(2,4-difluorobenzoyl)piperidin-1-yl]sulfonyl}thien-2-yl)methyl]-3-nitrobenzamide
N-[(5-{[4-(2,4-difluorobenzoyl)piperidin-1-yl]sulfonyl}thien-2-yl)methyl]-3-methoxybenzamide
2-Hydroxy-N-({5-[(4-{3-[(trifluoromethyl)sulfonyl]anilino}piperidin-1-yl)sulfonyl]-thien-2-yl}methyl)benzamide
N-[(5-{[4-(1H-1,2,3-benzotriazol-1-yl)piperidin-1-yl]sulfonyl}thien-2-yl)methyl]-3-methoxybenzamide
N-[(5-{[4-(1H-1,2,3-benzotriazol-1-yl)piperidin-1-yl]sulfonyl}thien-2-yl)methyl]-2-hydroxybenzamide N-{[5-({4-[4-(1,3-dithiolan-2-yl)anilino]piperidin-1-yl}sulfonyl)thien-2-yl]methyl}-3-nitrobenzamide
3-methoxy-N-[(5-{[4-(3-methoxyanilino)piperidin-1-yl]sulfonyl}thien-2-yl)methyl]-benzamide
3-methoxy-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-3-methoxybenzamide
3-methoxy-N-[(5-{[4-(3-propylanilino)piperidin-1-yl]sulfonyl}thien-2-yl)methyl]-benzamide
3-methoxy-N-{[5-({4-[3-(methylsulfonyl)anilino]piperidin-1-yl}sulfonyl)thien-2-yl]methyl}benzamide
3-methoxy-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-3-methoxybenzamide methyl
N-{[5-({4-[3-(aminocarbonyl)anilino]piperidin-1-yl}sulfonyl)thien-2-yl]methyl}-3-methoxybenzamide
3-methoxy-N-[(5-{[4-(2-methoxyanilino)piperidin-1-yl]sulfonyl}thien-2-yl)methyl]-benzamide
N-({5-[(4-{3-nitroanilino}piperidin-1-yl)sulfonyl]thien-2-yl}methyl)-3-methoxybenzamide
3-methoxy-N-{[5-({4-[2-(trifluoromethyl)anilino]piperidin-1-yl}sulfonyl)thien-2-yl]methyl}benzamide
N-({5-[(4-{2-nitroanilino}piperidin-1-yl)sulfonyl]thien-2-yl}methyl)-3-methoxybenzamide
N-{[5-({4-[4-(aminocarbonyl)anilino]piperidin-1-yl}sulfonyl)thien-2-yl]methyl}-3-methoxybenzamide
N-{[5-({4-[4-(1,3-dithiolan-2-yl)anilino]piperidin-1-yl}sulfonyl)thien-2-yl]methyl}-3-methoxybenzamide
N-[(5-{[4-(3-chloroanilino)piperidin-1-yl]sulfonyl}thien-2-yl)methyl]-3-methoxybenzamide
N-[(5-{[4-(4-chloroanilino)piperidin-1-yl]sulfonyl}thien-2-yl)methyl]-3-methoxybenzamide
3-methoxy-N-({5-[(4-{4-[(trifluoromethyl)sulfonyl]anilino}piperidin-1-yl)sulfonyl]-thien-2-yl}methyl)benzamide
N-({5-[(4-{3-[amino(imino)methyl]anilino}piperidin-1-yl)sulfonyl]thien-2-yl}methyl)-3-methoxybenzamide
N-({5-[(4-{3-[(2-hydroxyethyl)sulfonyl]anilino}piperidin-1-yl)sulfonyl]thien-2-yl}-methyl)-3-methoxybenzamide
3-methoxy-N-({5-[(4-{3-[(trifluoromethyl)sulfonyl]anilino}piperidin-1-yl)sulfonyl]-thien-2-yl}methyl)benzamide
N-({5-[(4-anilinopiperidin-1-yl)sulfonyl]thien-2-yl}methyl)-3-methoxybenzamide
3-methoxy-N-({5-[(4-{3-[(trifluoromethyl)sulfanyl]anilino}piperidin-1-yl)sulfonyl]-thien-2-yl}methyl)benzamide
N-[(5-{[4-(4-hydroxyanilino)piperidin-1-yl]sulfonyl}thien-2-yl)methyl]-3-methoxybenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
N-[(5-{[4-(2-hydroxyanilino)piperidin-1-yl]sulfonyl}thien-2-yl)methyl]-3-methoxybenzamide
3-methoxy-N-[(5-{[4-(pyrimidin-2-ylamino)piperidin-1-yl]sulfonyl}thien-2-yl)methyl]-benzamide
N-{[5-({4-[(3-aminopyridin-2-yl)amino]piperidin-1-yl}sulfonyl)thien-2-yl]methyl}-3-methoxybenzamide
N-[(5-{[4-({3-nitropyridin-2-yl}amino)piperidin-1-yl]sulfonyl}thien-2-yl)methyl]-3-methoxybenzamide
N-{[5-({4-[(2,2-dioxido-1,3-dihydro-2-benzothien-5-yl)amino]piperidin-1-yl}sulfonyl)-thien-2-yl]methyl}-3-methoxybenzamide
N-[(5-{[4-(2,3-dihydro-1H-inden-5-ylamino)piperidin-1-yl]sulfonyl}thien-2-yl)-methyl]-3-methoxybenzamide
3-methoxy-N-[(5-{[4-(2-propylanilino)piperidin-1-yl]sulfonyl}thien-2-yl)methyl]-benzamide
3-methoxy-N-[(5-{[4-(4-propylanilino)piperidin-1-yl]sulfonyl}thien-2-yl)methyl]-benzamide
N-[(5-{[4-(3-tert-butylanilino)piperidin-1-yl]sulfonyl}thien-2-yl)methyl]-3-methoxybenzamide
N-({5-[(4-{[3-chloro-5-(trifluoromethyl)pyridin-2-yl]amino}piperidin-1-yl)sulfonyl]-thien-2-yl}methyl)-3-methoxybenzamide
3-methoxy-N-{[5-({4-[3-(1,3-oxazol-5-yl)anilino]piperidin-1-yl}sulfonyl)thien-2-yl]methyl}benzamide
N-[(5-{[4-([1,1'-biphenyl]-3-ylamino)piperidin-1-yl]sulfonyl}thien-2-yl)methyl]-3-methoxybenzamide
3-methoxy-N-[(5-{[4-(3-propylphenoxy)piperidin-1-yl]sulfonyl}thien-2-yl)methyl]-benzamide
3-methoxy-N-{[5-({4-[3-(morpholin-4-ylsulfonyl)anilino]piperidin-1-yl}sulfonyl)thien-2-yl]methyl}benzamide
3-methoxy-N-[(5-{[4-(2-phenylethyl)piperidin-1-yl]sulfonyl}thien-2-yl)methyl]benzamide
N-[(5-{[4-(3-benzylanilino)piperidin-1-yl]sulfonyl}thien-2-yl)methyl]-3-methoxybenzamide
3-methoxy-N-[(5-{[4-(3-phenylpropyl)piperazin-1-yl]sulfonyl}thien-2-yl)methyl]-benzamide
3-methoxy-N-({5-[(4-{[4-(trifluoromethyl)pyrimidin-2-yl]amino}piperidin-1-yl)sulfonyl]thien-2-yl}methyl)benzamide
N-[(5-{[4-(3-cyclohexyl-4-hydroxyanilino)piperidin-1-yl]sulfonyl}thien-2-yl)methyl]-3-methoxybenzamide
N-({5-[(4-{3-[(butylamino)sulfonyl]anilino}piperidin-1-yl)sulfonyl]thien-2-yl}methyl)-3-methoxybenzamide
N-[(5-{[4-(3-ethylanilino)piperidin-1-yl]sulfonyl}thien-2-yl)methyl]-3-methoxybenzamide
3-methoxy-N-[(5-{[4-(5,6,7,8-tetrahydronaphthalen-1-ylamino)piperidin-1-yl]-sulfonyl}thien-2-yl)methyl]benzamide
N-[(5-{[4-(1H-1,2,3-benzotriazol-1-yl)piperidin-1-yl]sulfonyl}thien-2-yl)methyl]-5-nitro-1H-pyrazole-3-carboxamide
N-[(5-{[4-(1H-1,2,3-benzotriazol-1-yl)piperidin-1-yl]sulfonyl}thien-2-yl)methyl]-2-oxo-1,2-dihydropyridine-3-carboxamide
N-[(5-{[4-(1H-1,2,3-benzotriazol-1-yl)piperidin-1-yl]sulfonyl}thien-2-yl)methyl]-2-thioxo-1,2-dihydropyridine-3-carboxamide
N-[(5-{[4-(1H-1,2,3-benzotriazol-1-yl)piperidin-1-yl]sulfonyl}thien-2-yl)methyl]-3,4-dihydroxybenzamide
N-[(5-{[4-(1H-1,2,3-benzotriazol-1-yl)piperidin-1-yl]sulfonyl}thien-2-yl)methyl]-pyridine-2-carboxamide
N-[(5-{[4-(hexyloxy)piperidin-1-yl]sulfonyl}thien-2-yl)methyl]-3-methoxybenzamide
N-({5-[(4-heptanoylpiperidin-1-yl)sulfonyl]thien-2-yl}methyl)-3-methoxybenzamide
4-chloro-N-[(5-{[4-(3-propylanilino)piperidin-1-yl]sulfonyl}-2-furyl)methyl]benzamide
4-chloro-N-[(5-{[4-(3-chloroanilino)piperidin-1-yl]sulfonyl}-2-furyl)methyl]benzamide
4-chloro-N-[(5-{[4-(3-methoxyanilino)piperidin-1-yl]sulfonyl}-2-furyl)methyl]benzamide
4-chloro-N-{[5-({4-[3-(trifluoromethyl)anilino]piperidin-1-yl}sulfonyl)-2-furyl]-methyl}benzamide
4-chloro-N-{[5-({4-[3-(dimethylamino)anilino]piperidin-1-yl}sulfonyl)-2-furyl]-methyl}benzamide 4-chloro-N-{[5-({4-[3-(methylsulfonyl)anilino]piperidin-1-yl}sulfonyl)-2-furyl]-methyl}benzamide 4-chloro-N-{[5-({4-[3-(methylsulfanyl)anilino]piperidin-1-yl}sulfonyl)-2-furyl]-methyl}benzamide N-{[5-({4-[3-(aminosulfonyl)anilino]piperidin-1-yl}sulfonyl)-2-furyl]methyl}-4-chlorobenzamide methyl 3-({1-[(5-{[(4-chlorobenzoyl)amino]methyl}-2-furyl)sulfonyl]piperidin-4-yl}amino)benzoate 3-({1-[(5-{[(4-chlorobenzoyl)amino]methyl}-2-furyl)sulfonyl]piperidin-4-yl}amino)-benzamide 4-chloro-N-({5-[(4-{3-nitroanilino}piperidin-1-yl)sulfonyl]-2-furyl}methyl)benzamide 4-chloro-N-[(5-{[4-(2-methoxyanilino)piperidin-1-yl]sulfonyl}-2-furyl)methyl]-benzamide 4-chloro-N-{[5-({4-[2-(trifluoromethyl)anilino]piperidin-1-yl}sulfonyl)-2-furyl]-methyl}benzamide 4-chloro-N-({5-[(4-{2-nitroanilino}piperidin-1-yl)sulfonyl]-2-furyl}methyl)benzamide 4-chloro-N-[(5-{[4-(4-chloroanilino)piperidin-1-yl]sulfonyl}-2-furyl)methyl]benzamide 4-chloro-N-{[5-({4-[4-(trifluoromethyl)anilino]piperidin-1-yl}sulfonyl)-2-furyl]-methyl}benzamide 4-chloro-N-({5-[(4-{4-[(trifluoromethyl)sulfonyl]anilino}piperidin-1-yl)sulfonyl]-2-furyl}methyl)benzamide N-{[5-({4-[4-(aminocarbonyl)anilino]piperidin-1-yl}sulfonyl)-2-furyl]methyl}-4-chlorobenzamide 4-chloro-N-{[5-({4-[4-(1,3-dithiolan-2-yl)anilino]piperidin-1-yl}sulfonyl)-2-furyl]-methyl}benzamide N-({5-[(4-{3-[amino(imino)methyl]anilino}piperidin-1-yl)sulfonyl]-2-furyl}methyl)-4-chlorobenzamide 4-chloro-N-({5-[(4-{3-[(trifluoromethyl)sulfonyl]anilino}piperidin-1-yl)sulfonyl]-2-furyl}methyl)benzamide N-({5-[(4-anilinopiperidin-1-yl)sulfonyl]-2-furyl}methyl)-4-chlorobenzamide 4-nitro-N-({5-[(4-{3-[(trifluoromethyl)sulfanyl]anilino}piperidin-1-yl)sulfonyl]2-furyl}methyl)benzamide 4-chloro-N-({5-[(3-{3-[(trifluoromethyl)sulfonyl]anilino}pyrrolidin-1-yl)sulfonyl]thien-2-yl}methyl)benzamide 4-chloro-N-({5-[(4-{3-[(trifluoromethyl)sulfonyl]anilino}azepan-1-yl)sulfonyl]thien-2-yl}methyl)benzamide Thereby, the most preferred compounds are those which are selected from the group consisting of:

4-chloro-N-[(5-{[4-(2,4-difluorobenzoyl)piperidin-1-yl]sulfonyl}thien-2-yl)methyl]-benzamide 4-chloro-N-[(5-{[4-(phenylacetyl)-1,4-diazepan-1-yl]sulfonyl}thien-2-yl)methyl]-benzamide N-({5-[(4-anilinopiperidin-1-yl)sulfonyl]thien-2-yl}methyl)-4-chlorobenzamide N-[(5-{[4-(1H-1,2,3-benzotriazol-1-yl)piperidin-1-yl]sulfonyl}thien-2-yl)methyl]-4-chlorobenzamide N-[(5-{[4-(1H-benzimidazol-1-yl)piperidin-1-yl]sulfonyl}thien-2-yl)methyl]-4-chlorobenzamide 4-chloro-N-{[5-({4-[3-propylanilino]piperidin-1-yl}sulfonyl)thien-2-yl]methyl}-benzamide 4-chloro-N-[(5-{[4-(4-chloroanilino)piperidin-1-yl]sulfonyl}thien-2-yl)methyl]-benzamide 4-chloro-N-({5-[(4-{3-[(2-hydroxyethyl)sulfonyl]anilino}piperidin-1-yl)sulfonyl]thien-2-yl}methyl)benzamide N-{[5-({4-[3-(aminosulfonyl)anilino]piperidin-1-yl}sulfonyl)thien-2-yl]methyl}-4-chlorobenzamide 4-chloro-N-[(5-{[4-(1-naphthoyl)piperazin-1-yl]sulfonyl}thien-2-yl)methyl]benzamide 4-nitro-N-[(5-{[4-(3-methoxyanilino)piperidin-1-yl]sulfonyl}thien-2-yl)methyl]-benzamide methyl 3-{[1-({5-[({4-nitrobenzoyl}amino)methyl]thien-2-yl}sulfonyl)piperidin-4-yl]amino}benzoate N-[(5-{[4-(1H-1,2,3-benzotriazol-1-yl)piperidin-1-yl]sulfonyl}thien-2-yl)methyl]-2-hydroxybenzamide N-({5-[(4-{2-nitroanilino}piperidin-1-yl)sulfonyl]thien-2-yl}methyl)-3-methoxybenzamide A further aspect of the present invention consists in the use of the sulfonamide derivatives according to formula I for the preparation of pharmaceutical compositions for the modulation—notably for the down-regulation, e.g. up to the inhibition—of the JNK function or signalling pathway associated disorders, in particular against neuronal disorders and/or against disorders of the immune system as well as said pharmaceutical compositions themselves. Preferred JNK pathways are the JNK 1 and/or 2 and/or JNK3.

As above pointed out, the compounds of formula I are suitable to be used as a medicament. Some few of the compounds falling into the above generic formula I have been disclosed prior to the filing of the present application, whereby for 9 of them no medical or biological activity whatsoever was described so far. Hence, it is herein reported that both the novel and the few known compounds falling under the above set out generic formula I are indeed suitable for use in treating disorders of the autoimmune system and neuronal system of mammals, notably of human beings. More specifically, the compounds according to formula I, alone or in the form of a pharmaceutical composition, are useful for the modulation of the JNK pathway, more specifically for treatment or prevention of disorders associated with abnormal expression or activity of JNK, notably of JNK2 and 3. Said modulation usually preferably involves the inhibition of the JNK pathways, notably of the JNK2 and/or 3. Such an abnormal expression or activity of INK could be triggered by numerous stimuli (e.g. stress, septic schock, oxidative stress, cytokines) and could lead to out-of-control apoptosis or autoimmune diseases that is frequently involved in the below enumerated'disorders and disease states. Hence, the compounds according to formula I could be used for the treatment of disorders by modulating the JNK function or signalling pathways. Said modulation of the JNK function or pathways could involve its activation, but preferably it involves the down-regulation up to inhibition of the JNK pathways, notably of the JNK 1 and/or 2 and/or JNK3. The compounds according to formula I could be employed alone or in combination with further pharmaceutical agents, e.g. with a further JNK modulator.

Specifically, the compounds pursuant to formula I are useful for the treatment or prevention of immuno- and/or neuronal-related diseases or pathological states in which inhibition of JNK2 or JNK3 plays a critical role such as epilepsy, neurodegenerative diseases including Alzheimer's disease, Huntington's disease, Parkinson's disease; retinal diseases; spinal cord injury; head trauma, autoimmune diseases including multiple sclerosis, inflammatory bowel disease (IBD), rheumatoid arthritis; asthma; septic shock; transplant rejection; cancers including breast, colorectal, pancreatic and cardiovascular diseases including stroke, cerebral ischemia, arterosclerosis, myocordial infarction, myocordial reperfusion injury.

Quite surprisingly it turned out that the inventively found compounds according to formula I do show a considerable activity as inhibitors of JNK2 and 3. According to a preferred embodiment, the compounds according to the invention are essentially inactive in view of 2 further apoptosis modulating enzymes, i.e. p38 and/or ERK2, belonging incidentally to the same family as JNK2 and 3. Hence, the compounds according to the present invention offer the possibility to selectively modulate the JNK pathway, and in particular to treat disorders related to the JNK pathways, while being essentially inefficient with regard to other targets like said p38 and ERK2, so that they could indeed be viewed as selective inhibitors. This is of considerable significance, as these related enzymes are generally involved in different disorders, so that for the treatment of a distinct disorder, it is desired to employ a correspondingly selective medicament. As a matter of fact, prior to the herein reported, surprisingly found pharmaceutically active sulfonamide derivatives according to formula I, nothing was known in respect of the use of small molecule chemical compounds as inhibitors of the JNK kinase pathway.

Still a further aspect of the present invention consists in the actually novel sulfonamide derivatives of formula I, i.e. those sulfonamide derivatives according to formula I that have not been disclosed by the prior art. Thereby, a total of 9 compounds have been disclosed by the CEREP company in as far as they are mentioned in a company catalogue, without any medical indication, though.

Generally, the compounds according to formula I of the CEREP company are only those wherein $Ar^1$ is 4-chlorophenyl and X is O and $R^1$ is H, $Ar^2$ is a thienyl group, while Y is a piperazino-, a 3-methyl piperazino-, a piperazino-3,5-dione- or a piperidino group being substituted in the following way:

where Y is a piperazino group, $L^1$ is diphenylmethyl, benzo[1,3]dioxol-5-yl-methyl, 4-methoxy phenyl, 2-hydroxyethyl, methyl group, 4-chlorophenyl methyl, where Y is a 3-methyl piperazino, $L^1$ is 4-chlorophenyl methyl, where Y is a piperazino-3,5-dione group, $L^1$ is 2-phenyl ethyl, and where Y is a piperidino group, $L^1$ is H, and $L^2$ is 2-hydroxy ethyl.

Compounds according to formula I that have been disclosed by the prior art together with a medical indication are those, wherein:

Y is a piperidino- or a pyrrolidino group being substituted at the β-position of said sulfonamide nitrogen by one $R^6$=benzo[5,6]cyclohepta[1,2b]pyridine, or a benzo[5,6]cyclohept(3,4)ene[1,2b]pyridine, whereby $Ar^1$ is phenyl, $Ar^2$ is thienyl, X is oxygen, $R^1$ is hydrogen; $L^1$ and $L^2$ are H and n is 1 for the treatment of proliferative diseases (WO 96/30017).

X is oxygen, $R^1$ is hydrogen and n is 1, while Y is a piperazino group, whereby $L^1$ is a substituent that includes a phenyl being imperatively substituted by a group —C(=NH)—NH$_2$ (benzamidine) or a protected form thereof to be used as factor XA inhibitors (WO 99/16751).

Two further compounds are rather incidentally disclosed in WO 97/45403 (i.e. 2-{[2-(benzoylaminomethyl)-thiophene]-5-sulfonyl}-1,2,3,5,6,7-hexahydro-N,N-dipropylcyanopent[f]isoindol-6-amine as selective dopamine D3 ligand) and in WO 97/30992 (i.e. N-[[5-[[7-cyano-1,2,3,5-tetrahydro-1-(1H-imidazol-4-yl-methyl)-3-(phenylmethyl)-4H-1,4-benzodiazepin-4-yl]sulfonyl]-2-thienyl]methyl]benzamide and its hydrochloride to be used for inhibiting farnesyl-protein transferase).

Finally, compounds of formula I wherein X is oxygen and Y is a 4-8 membered saturated cyclic alkyl containing one or two nitrogen atoms, said Y being imperatively substituted by an amido group (C=O)N(R,R') at the alpha position of the sulfonamide nitrogen are disclosed within WO 98/53814. Said compounds are mentioned to be useful in the inhibition of cell adhesion.

Hence, the entirely novel sulfonamide derivatives are those of the below set out general formula I whereby the above identified known compounds are excluded.

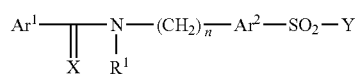

Still a further object of the present invention is a process for preparing the novel sulfamide derivatives according to formula I which have been set out above.

The sulfonamide derivatives of this invention can be prepared from readily available starting materials using the following general methods and procedures.

It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvent used, but such conditions can be determined by one skilled in the art by routine optimisation procedures.

In a preferred method of synthesis, the sulfonamide derivatives of the invention are prepared by first coupling an amine of formula II:

where $Ar^2$ and $R^1$ are as defined above, with an acyl chloride of formula III:

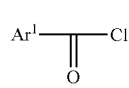

where $Ar^1$ is as defined above, to provide an amide of formula IV:

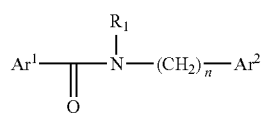

Amines of formula II are either known compounds or can be prepared from known compounds by conventional procedures. Preferred amines as starting materials include thien-2-yl-methylamine, furan-2-yl-methylamine, pyridyl-2-ylmethylamine and the like. The acyl chlorides of formula III are also commercially available or previously described compounds. Preferred acyl chlorides include 4-chlorobenzoyl chloride, 4-fluorobenzoyl chloride, 4-trifluoromethylbenzoyl chloride and the like. If not known, the acid halide can be prepared by reacting the corresponding carboxylic acid with an inorganic acid halide, such as thionyl chloride, phosphorus trichloride or oxalyl chloride under conventional conditions.

Generally, this reaction is performed upon using about 1 to 5 molar equivalents of the inorganic acid halide or oxalyl chloride, either in pure form or in an inert solvent, such as carbon tetrachloride, at temperature in the range of about 0°

C. to about 80° C. for about 1 to about 48 hours. A catalyst, as N,N-dimethylformamide, may also be used in this reaction.

When an acyl halide is employed in the coupling reaction, it is typically reacted with amine II in the presence of a suitable base to scavenge the acid generated during the reaction. Suitable bases include, by way of example, triethylamine, diisopropylethylamine, N-methylmorpholine and the like. Alternatively, an excess of amine II may be used to scavenge the acid generated during the reaction.

Alternatively, the carboxylic acid of compound III can be employed in the coupling reaction. The carboxylic acid of III are usually commercially available reagents or can be prepared by conventional procedures.

The coupling reaction of carboxylic acid of III (i.e. the acyl chloride) is conducted upon using any conventional coupling reagent including, for example, carbodiimides such as dicyclohexylcarbodiimide, N-(3-dimethylaminopropyl)-N'-ethylcarbodiimide and other promoting agents, such as N,N-carbonyl-diimidazole or PyBOP. This reaction can be conducted with or without the use of well known additives such as N-hydroxysuccinimide, 1-hydroxybenzotriazole, etc. which are known to facilitate the coupling of carboxylic acids and amines.

The coupling reaction using either acid halide III or its carboxylic acid is preferably conducted at a temperature of from about 0° C. to about 6° C. for about 1 to about 24 hours. Typically, the reaction is conducted in an inert aprotic polar solvent such as N,N-dimethylformamide, dichloromethane, chloroform, acetonitrile, tetrahydrofuran and the like using about 1 to about 5 molar equivalents of the amine based on the carboxylic acid or its acid halide. Upon completion of the reaction, the carboxamide N is recovered by conventional methods including precipitation, chromatography, filtration, distillation and the like.

The sulfonyl chlorides of formula V necessary for the preparation of the sulfonylpiperidines or piperazines of formula I are prepared using conventional sulfonating methods:

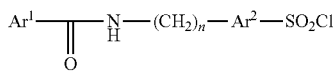

V

A preferred sulfonating reagent for use in this reaction is chlorosulfonic acid. Typically, the sulfonation reaction is performed by treating the carboxamide of formula (IV) with about 5 to about 10 molar equivalent of the sulfonating reagent in an inert solvent, such as dichloromethane, at a temperature ranging from about −70° C. to about 50° C. Preferably, the addition of chlorosulfonic acid takes place at −70° C. and leads to the formation of the intermediate sulfonic acid. Increasing the temperature to 20° C. allows the formation of the sulfonyl chloride of formula V.

According to a further preferred method of preparation notably in case that the above pointed out method leading to the preliminary synthesis of sulfonyl chloride of formula V is not applicable, the sulfonyl piperidines and piperazines of this invention are prepared by the following steps:

Protection of the amine function of compounds of formula II;
Chlorosulfonylation of the aromatic group;
Formation of the sulfonamide function;
Deprotection of the protection group;
Acylation of the above generated free amine;

Amines of formula II are protected with a suitable protecting group of an amine moiety to provide intermediate of formula VI wherein P denotes the protecting group.

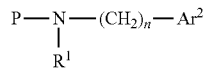

VI

Numerous protecting groups P of the amine function as well as their introduction and removal, are well described in T. W. Greene and G. M. Wuts, Protecting groups in Organic Synthesis, Third Edition, Wiley, New York, 1998, and references cited therein. Preferred are protecting groups that are acids and bases stable and can be further removed by using metal transition complexes such as palladium complexes, for example the allylcarbamate group (Alloc) or the N,N'-bisallyl group. Another preferred protecting group is the maleimide group which is stable in a all range of experimental conditions.

The introduction of said groups can be performed by reacting the corresponding bisallylcarbonate anhydride or allylbromide or maleic anhydride in the presence of a base such as triethylamine, diisopropylethylamine, N-methylmorpholine and the like in an aprotic solvent such as N,N-dimethylformamide, dichloromethane, chloroform, acetonitrile, tetrahydrofuran and the like at a temperature ranging from about 0° C. to about 80° C.

Compounds of formula VI are then sulfonated using a conventional very mild sulfonating procedure that allows the obtention of sulfonyl chloride of formula VII.

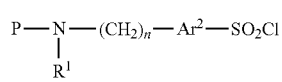

VII

Typically, protected amine VI is treated with a base such as n-butyllithium or tert-butyl-lithium under an inert atmosphere, in a polar aprotic solvent such as tetrahydrofuran, ether or dioxane at a temperature ranging from −70° C. to 0° C. during a time ranging from 15 minutes to 4 hours. The so formed anion is then treated with $SO_2Cl_2$ or most preferably $SO_2$ by bubbling the gas into the reaction mixture at a temperature ranging from −70° C. to 20° C. during a time ranging from 5 minutes to 1 hour. The sulfonate obtained is then transformed "in situ" to the sulfonyl chloride of formula VII by contacting with N-chlorosuccinimide at a temperature ranging from 0 C to 70° C.

The sulfonamide derivatives of formula I are then prepared from the corresponding above mentioned sulfonyl chloride V or VII, by reaction with a corresponding cyclic amine, e.g. either with a piperazine or piperidine derivative of the general formula VIII or IX.

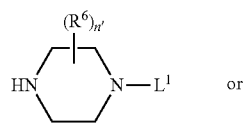

VIII or

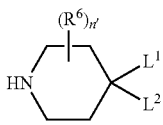

or a pyrrolidine, an azepan or a 1,4-diazepan of the below formulas

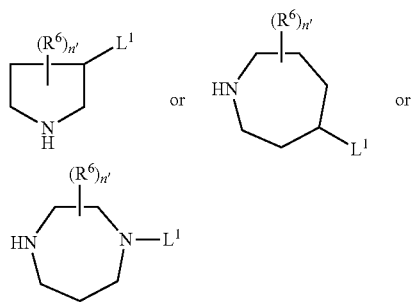

whereby $R^6$, n $L^1$ and $L^2$ are as above defined.

The above set out cyclic amines, notably those of formula VIII or IX are either commercially available compounds or compounds that can be prepared by known procedures.

Typically, piperazines of type VIII can be prepared upon using conventional methods known by a person skilled in the art.

For $L^1$ and/or $L^2$=aryl, suitable methods of preparation are described in *Tetrahedron Lett.* 1996, 37, 8487-8488 and references cited therein.

For $L^1$ and/or $L^2$=aryl $C_1$-$C_6$ alkyl, a further preferred method is the reaction of the corresponding piperazine or mono-N-protected piperazine with compounds of formula X

wherein X is Cl, Br, I, OTs, OMs

The reaction is generally conducted in the presence of a base such as triethylamine, di-isopropylethylamine, potassium carbonate and the like in solvent such as N,N-dimethylformamide, dimethylsulfoxide, N-methylpyrrolidone, ethanol, acetonitrile at a temperature from about 0° to about 100° C.

For $L^1$ and/or $L^2$=—C(S)—, a further preferred method is the conversion of compounds of type XI using the Lawesson's reagent which allows the transformation of an amide into a thioamide group as described in *Bull. Soc. Chim. Belgium,* 1978, 87, 229.

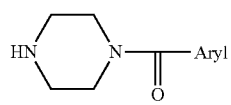

The sulfonamides of formula I are readily prepared by contacting the sulfonyl chlorides V with an amine of formula VIII in the presence of a suitable base to scavenge the acid generated during the reaction. Suitable bases include, by way of examples, triethylamine, diisopropylethylamine, N-methylmorpholine and the like. The reaction is preferably conducted in solvent such as N,N-dimethylformamide, dimethylsulfoxide, N-methyl-pyrrolidone, ethanol, acetonitrile at a temperature from about 0° to about 100° C.

Alternatively, the sulfonamide derivatives of formula I are readily prepared from the corresponding sulfonyl chloride V or VII, by reaction with a piperidine of general formula IX. Piperidines of formula IX are either commercially available compounds or compounds that can be prepared by known procedures. Typically, piperidines of type IX can be prepared using conventional methods known by one skilled in the art and described by way of examples in *J. Pharm. Sci.* 1972, 61, 1316; *J. Heterocyclic. Chem.,* 1986, 23, 73; *Tetrahedron Lett.,* 1996, 37, 1297, U.S. Pat. No. 5,106,983, WO/9113872 and WO/9606609.

Preferred methods of obtaining piperidines of formula IX are the following:

For $L^1$=H and $L^2$=(CH$_2$)n-Aryl wherein n=0,1,2; addition of an organometallic species such as $Ar^3(CH_2)_n$Li or $Ar^3(CH_2)_n$MgBr on mono-protected 4-piperidone followed by reduction of the so-formed double bound which allows the formation of compounds of type IX.

For $L^2$=—NR—(CH$_2$)n-Aryl wherein n=0,1,2, a preferred method is the reductive amination of 4-piperidone with amines of type Aryl-(CH$_2$)n-NR—H.

A further preferred method in the case where n=0 is a "Mitsunobu type" coupling between an activated aniline of type XII with mono-N-protected 4-piperidol as described in *Tetrahedron Lett.* 1995, 36, 6373-6374.

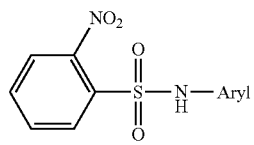

Deprotection of the sulfamino group is then carried out using thiophenol in the presence of potassium carbonate.

For $L^2$=—NR$^3$'C(O)R$^3$, —NR$^3$'C(O)NR$^3$'R$^3$, NR$^3$'SO$_2$—R$^3$, a preferred method of synthesis of compounds of formula IX is the reaction of commercially available N—BOC-4-aminopiperidine with respectively acyl chlorides, isocyanates and sulfonyl chloride under classical conditions very well known by one skilled in the art.

When $L^2$=—CO-Aryl, compounds of formula IX are readily prepared by contacting well chosen aromatic or heteroaromatic rings with intermediate of type XIII

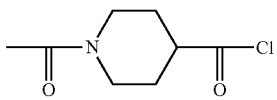

in the presence of a Lewis acid such as aluminum trichloride or titanium tetrachloride in a polar aprotic solvent such as dichloromethane. Intermediate XIII can be easily obtained by first acetylation of piperid-4-yl carboxylic acid and their formation of the acyl chloride by treatment with thionyl chloride.

The sulfonamides of formula I are readily prepared by contacting the sulfonyl chloride V with an amine of formula IX in the presence of a suitable base to scavenge the acid generated during the reaction. Suitable bases include, by way of examples, triethylamine, diisopropylethylamine, N-methylmorpholine and the like. The reaction is preferably conducted in solvent such as N,N-dimethylformamide, dimethylsulfoxide, N-methylpyrrolidone, ethanol, acetonitrile at a temperature from about 0° to about 100° C.

The sulfonamides of formula XIV are readily prepared by contacting the sulfonyl chloride VII with an amine of formula VIII or IX in the presence of a suitable base to scavenge the acid generated during the reaction. Suitable bases include, by way of examples, triethylamine, diisopropylethylamine, N-methylmorpholine and the like. The reaction is preferably conducted in solvent such as N,N-dimethylformamide, dimethylsulfoxide, N-methylpyrrolidone, ethanol, acetonitrile at a temperature from about 0° to about 100° C. The use of sulfonyl chloride of type VII leads to amines that have to be deprotected using well known methods by one skilled in the art to afford amine of general formula XIV

wherein $R^1$, $Ar^2$, Y and n are as above defined.

Derivatives of type XIV are then acylated according to described methods for the preparation of amides by condensation of amines with acid chlorides or carboxylic acids in the preferred conditions described above leading to compounds of general formula I In the particular case of compounds of general formula I where Y represents a piperazine derivative, an alternative method of preparation which has also to be considered as part of this invention, said method of preparation consisting in the condensation of a piperazine derivative of formula XV

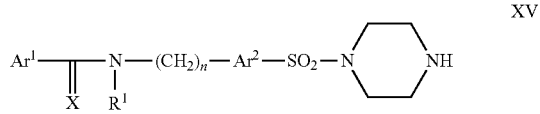

with electrophiles $L^1$ which will be chosen depending on the nature of $L^1$ (see the above definition of $L^1$, $L^2$). Procedures and methods to perform these types of condensation are well-known and have been well described on various synthesis of N-substituted piperazine derivatives.

If the above set out general synthetic methods are not applicable for obtaining compounds of formula I, suitable methods of preparation known by a person skilled in the art should be used. For example, when $Ar^1$ is phenyl, one should start from commercially available 4-cyanophenyl sulfonyl chloride and applies conventional methods known by a person skilled in the art to reach sulfonamide derivatives of formula L A final aspect of the present invention is related to the use of the compounds according to formula I for the modulation of the JNK function, or signaling pathways, the use of said compounds for the preparation of pharmaceutical compositions for the modulation of the JNK pathway as well as the formulations containing the active compounds according to formula I. Said modulation of the JNK pathway is viewed as a suitable approach of treatment for various disorders. When employed as pharmaceuticals, the sulfonamide derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as JNK inhibitor, notably JNK2 and JNK3, for the treatment of disorders of the immune as well as the neuronal system of mammals, notably of humans, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfonamides derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include preferred, pre-measured ampoules or syringes of the liquid compositions or pills, tablets, capsules or the like in the case of solid compositions. In such compositions, the sulfonamide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the sulfonamide compound of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, $17^{th}$ Edition, 1985, Marck Publishing Company, Easton, Pa., which is incorporated herein be reference. The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

EXAMPLES

Protocol #1

Example 1

Preparation of 4-chloro-N-[5-(piperazine-1-sulfonyl)-thiophen-2-yl-methyl]-benzamide 1

4-Chloro-N-thiophen-2-ylmethyl-benzamide 1a

A solution of 4-chlorobenzoyl chloride (0.114 mol) in 50 mL dry $CH_2Cl_2$ was added over 30 min to a stirred solution of 2-aminomethyl-thiophene (0.137 mol) and $^iPr_2NEt$ (0.25 mol) in $CH_2Cl_2$ (200 mL) at 0° C. A white solid was formed and the reaction was allowed to warm to room temperature over 1 h. The mixture was diluted with 200 mL of $CH_2Cl_2$, washed twice with HCl aq. (0.1N) and dried over $MgSO_4$. Evaporation of the solvents afforded 28 g (98%) of the title benzamide as a white solid: m.p. 153-54° C., $^1H$ NMR ($CDCl_3$) δ 7.9 (d, J=8.67 Hz, 2H), 7.58 (d, J=8.67 Hz, 2H), 7.44 (dd, J=3.77, 1.13 Hz, 1H), 7.22 (d, J=5.27 Hz, 1H), 7.16 (dd, J=3.39, 5.27 Hz, 1H), 6.62 (br d, 1H), 4.98 (d, J=5.65 Hz, 2H).

5-({[1-(4-Chloro-phenyl-methanoyl]-amino}-methyl)-thiophene-2-sulfonyl chloride 1b Chlorosulfonic acid (20.1 mL, 198 mmol) in $CH_2Cl_2$ (80 mL) was added dropwise to a solution of 1a (10 g, 40 mmol) in $CH_2Cl_2$ (500 mL) at −80° C. The mixture was allowed to reach room temperature in 5 h. The reaction mixture was poured on ice and quickly extracted with $CH_2Cl_2$. The organic layer was dried over $MgSO_4$ and the solvent was evaporated to dryness which afforded 8.8 g (63%) of desired sulfonyl chloride 1b; mp 133-35° C., $^1H$ NMR (DMSO-d6) δ 9.21 (t, J=6.4 Hz, 1H), 7.87 (d, J=8.67 Hz, 2H), 7.53 (d, J=8.67 Hz, 2H), 6.91 (d, J=339 Hz, 1H), 6.77 (d, J=339 Hz, 1H), 4.53 (d, J=3.77 Hz, 2H).

4-Chloro-N-[5-(piperazine-1-sulfonyl)-thiophen-2-ylmethyl]-benzamide 1

A solution of 1b (1 g, 2.9 mmol) in 0.5 mL DMF and 2 mL $CH_2Cl_2$ was added slowly at 0° C. to piperazine (985 mg, 11.4 mmol) in $CH_2Cl_2$ (11 mL). The reaction was stirred for 2 h while room temperature was reached. The reaction mixture was washed with sat. $NaHCO_3$ and dried over $MgSO_4$. After evaporating the solvent 1.76 g (62%) of 1c was isolated. $^1H$ NMR (DMSO-d6) δ 938 (t, J=5.27 Hz, 1H), 7.90 (d, J=8.67 Hz, 2H), 7.56 (d, J=8.67 Hz, 2H), 7.46 (d, J=3.77 Hz, 1H), 7.18 (d, J=4.14 Hz, 1H), 4.67 (d, J=6.03 Hz, 2H), 2.66-2.84 (m, 8H).

Example 2

Preparation of 4-Chloro-N-{5-[4-(3-Trifluoromethanesulfonyl-phenylamino)-piperidine-1-sulfonyl]-thiophen-2-ylmethyl}-benzamide 2

To a stirred solution of 4-((3-Trifluoromethanesulfonyl)-phenylamino)-piperidine (580 mg, 1.88 mmol) and $iPr_2NEt$ (1.46 μl, 8.6 mmol) in $CH_2Cl_2$ (250 mL) was added 1b (600 mg, 1.71 mmol) in DMF/$CH_2Cl_2$ (1:3,15 mL). After 3 h the reaction mixture was washed with HCl (0.1 N) and sat. NaCl solution, and dried over $MgSO_4$. The solvent was evaporated and the residue was filtered through silica gel using cyclohexane/ethylacetate 1:1 as eluent. 2 was isolated as white solid (840 mg, 79%).mp.: 198-199° C. $^1H$ NMR (DMSO-d6) δ 938 (t, J=5.6 Hz, 1H), 7.74 (d, J=8.6 Hz, 2H), 7.45-733 (m, 4H), 7.28 (d, J=7.9 Hz, 1H), 7.06 (d, J=3.8 Hz, 1H), 7.02 (s, 1H), 6.90 (d, J=7.9 Hz, 1H), 6.69 (t, J=5.6 Hz, 1H), 4.68 (d, J=5.6 Hz, 2H), 4.00 (s, b, Hz, 1H), 3.71 (d, J=12.1 Hz, 2H), 332 (s, b, 1H), 2.62 (dd, J=12.1 Hz, 2.26 Hz, 2H), 2.11 (d, J=13.56 Hz, 2H), 1.65-1.48 (m, 2H). M/Z APCI: 622.2 (M+1), 620.1 (M−1). $C_{24}H_{23}ClF_3N_3O_5S_3$ Calc.: C, 46.34%. H, 3.73%. N, 6.75%. Found: C, 46.05%, H, 3.84%, N, 6.69%.

Alternatively 2 can be synthesised in a parallel solution phase approach.

In a 4 mL Alltech® tube 1 eq. of amine is shaked with polymerbound NMM (4 eq.) in 1.2 mL $CH_2Cl_2$/DMF. After 15 min 1 mL of a stock solution of 1b in $CH_2Cl_2$/DMF (1.2 eq.) is added and the reaction slurry is shaked. After 3 h Aminomethyl Merryfield resin (0.4 eq) is added and the reaction is shaked overnight. The solution is filtered off, the resins are washed 3× with $CH_2Cl_2$, and the solvents are evaporated at medium temperature in a Savant Speed Vac® Plus vacuum centrifuge for The following compounds were prepared on a parallel fashion according to the examples described above The following table provides HPLC data and mass spectroscopy data of the mentioned examples. [1,2]

| | Example Name | Rt HPLC | Purity | Gradient HPLC | Mass M + 1 | Mass M |
|---|---|---|---|---|---|---|
| 3 | 4-chloro-N-({5-[(4-pyridin-2-ylpiperazin-1-yl)-sulfonyl]thien-2-yl}methyl)benzamide | 17.87 | 97 | c | 477 | 475 |
| 4 | 4-chloro-N-[(5-{[4-(4-fluorobenzoyl)piperidin-1-yl]sulfonyl}thien-2-yl)methyl]benzamide | 15.33 | 96.2 | b | | |

-continued

| Example | Name | Rt HPLC | Purity | Gradient HPLC | Mass M + 1 | Mass M |
|---|---|---|---|---|---|---|
| 5 | 4-chloro-N-{[5-({4-[4-(trifluoromethyl)phenyl]-piperazin-1-yl}sulfonyl)thien-2-yl]methyl}-benzamide | 15.82 | 93 | b | 545 | 543 |
| 6 | 4-chloro-N-({5-[(4-{2-nitrophenyl}piperazin-1-yl)sulfonyl]thien-2-yl}methyl)benzamide | 14.43 | 99 | b | 521 | 519 |
| 7 | 4-chloro-N-({5-[(4-{4-nitrophenyl}piperazin-1-yl)sulfonyl]thien-2-yl}methyl)benzamide | 13.99 | 93.3 | b | 522 | 520 |
| 8 | 4-chloro-N-[(5-{[4-(2-furoyl)piperazin-1-yl]sulfonyl}thien-2-yl)methyl]benzamide | 11.76 | 82 | b | 494 | 492 |
| 9 | 4-chloro-N-[(5-{[4-(4-hydroxyphenyl)piperazin-1-yl]sulfonyl}thien-2-yl)methyl]benzamide | 11.98 | 78 | b | 492 | 490 |
| 10 | 4-chloro-N-[(5-{[4-(2-oxo-2-pyrrolidin-1-ylethyl)piperazin-1-yl]sulfonyl}thien-2-yl)methyl]benzamide | 11.05 | 90 | b | 511 | 509 |
| 11 | 4-chloro-N-[(5-{[4-(2-morpholin-4-yl-2-oxoethyl)-piperazin-1-yl]sulfonyl}thien-2-yl)methyl]-benzamide | 10.44 | 89 | b | 527 | 525 |
| 12 | 4-chloro-N-[(5-{[4-(pyridin-4-ylmethyl)piperazin-1-yl]sulfonyl}thien-2-yl)methyl]benzamide | 11.62 | 89 | b | 491 | 489 |
| 13 | 4-chloro-N-[(5-{[4-(2-thien-2-ylethyl)piperazin-1-yl]sulfonyl}thien-2-yl)methyl]benzamide | 14.58 | 90 | b | 510 | 508 |
| 14 | 4-chloro-N-[(5-{[4-(3,5-dimethoxyphenyl)piperazin-1-yl]sulfonyl}thien-2-yl)methyl]benzamide | 14.04 | 93 | b | 536 | 534 |
| 15 | 4-chloro-N-[(5-{[4-(cyclohexylmethyl)piperazin-1-yl]sulfonyl}thien-2-yl)methyl]benzamide | 17.27 | 88 | b | 496 | 494 |
| 16 | 4-chloro-N-[(5-{[4-(2-methoxyphenyl)piperazin-1-yl]sulfonyl}thien-2-yl)methyl]benzamide | 14.59 | 88 | b | 506 | 504 |
| 17 | N-({5-[(4-benzylpiperazin-1-yl)sulfonyl]thien-2-yl}methyl)-4-chlorobenzamide | 14.75 | 82 | b | 490 | 488 |
| 18 | 4-chloro-N-[(5-{[4-(2-phenylethyl)piperazin-1-yl]sulfonyl}thien-2-yl)methyl]benzamide | 10.27 | 93 | b | 504 | 502 |
| 19 | 4-chloro-N-[(5-{[4-(4-fluorobenzyl)piperazin-1-yl]sulfonyl}thien-2-yl)methyl]benzamide | 14.82 | 91 | b | 508 | 506 |
| 20 | 4-chloro-N-[(5-{[4-(2-cyanophenyl)piperazin-1-yl]sulfonyl}thien-2-yl)methyl]benzamide | 14.14 | 87 | b | 501 | 499 |
| 21 | 4-chloro-N-{[5-({4-[4-chloro-3-(trifluoromethyl)-phenyl]piperazin-1-yl}sulfonyl)thien-2-yl]methyl}-benzamide | 16.49 | 94 | b | 578.5 | 576.5 |
| 22 | 4-chloro-N-[(5-{[4-(3-piperidin-1-ylpropyl)-piperazin-1-yl]sulfonyl}thien-2-yl)methyl]-benzamide | 7.87 | 95 | b | 525 | 523 |
| 23 | 4-chloro-N-({5-[(4-{4-chloro-2-nitrophenyl}-piperazin-1-yl)sulfonyl]thien-2-yl}methyl)benzamide | 15.38 | 99 | b | 555.5 | 553.4 |
| 24 | 4-chloro-N-[(5-{[4-(6-methylpyridin-2-yl)piperazin-1-yl]sulfonyl}thien-2-yl)methyl]benzamide | 9.3 | 91 | b | 491 | 489 |
| 25 | 4-chloro-N-({5-[(4-hydroxy-4-phenylpiperidin-1-yl)sulfonyl]thien-2-yl}methyl)benzamide | 12.84 | 94 | b | 491 | 489 |
| 26 | N-({5-[(4-benzoylpiperidin-1-yl)sulfonyl]thien-2-yl}methyl)-4-chlorobenzamide | 14.35 | 90 | b | 503 | 501 |
| 27 | 4-chloro-N[(5-{[4-(2-oxo-2,3-dihydro-1H-benzimidazol-1-yl)piperidin-1-yl]sulfonyl}thien-2-yl)methyl]benzamide | 12.22 | 93 | b | 531 | 529 |
| 28 | N-({5-[(4-benzylpiperidin-1-yl)sulfonyl]thien-2-yl}methyl)-4-chlorobenzamide | 16.03 | 93 | b | 489 | 487 |
| 29 | 4-chloro-N-({5-[(4-oxo-1-phenyl-1,3,8-triazaspiro-[4.5]dec-8-yl)sulfonyl]thien-2-yl}methyl)benzamide | 13.14 | 89 | b | 545 | 543 |
| 30 | 4-chloro-N-{[5-({4-[2-(methylanilino)-2-oxoethyl]-piperazin-1-yl}sulfonyl)thien-2-yl]methyl}-benzamide | 9.86 | 97 | b | 547 | 545 |
| 31 | 4-chloro-N-{[5-({4-[hydroxy(diphenyl)methyl]-piperidin-1-yl}sulfonyl)thien2-yl]methyl}-benzamide | 15.36 | 96 | b | 581 | 579 |
| 32 | 4-chloro-N-[(5-{[4-(3-cyanopyrazin-2-yl)piperazin-1-yl]sulfonyl}thien-2-yl)methyl]benzamide | 13.06 | 86 | b | 503 | 501 |
| 33 | 4-chloro-N-({5-[(4-{5-nitropyridin-2-yl}piperazin-1-yl)sulfonyl]thien-2-yl}methyl)benzamide | 13.76 | 76 | b | 522 | 520 |
| 34 | 4-chloro-N-{[5-({4-[3-chloro-5-(trifluoromethyl)-pyridin-2-yl]piperazin-1-yl}sulfonyl)thien-2-yl]methyl}benzamide | 16.32 | 90 | b | 579.5 | 577.6 |
| 35 | 4-chloro-N-{[5-({4-[5-(trifluoromethyl)pyridin-2-yl]piperazin-1-yl}sulfonyl)thien-2-yl]methyl}-benzamide | 14.88 | 80 | b | 545 | 543 |
| 36 | 4-chloro-N-{[5-({4-[3-(trifluoromethyl)pyridin-2-yl]piperazin-1-yl}sulfonyl)thien-2-yl]methyl}-benzamide | 14.63 | 95 | b | 545 | 543 |

-continued

| Example | Name | Rt HPLC | Purity | Gradient HPLC | Mass M + 1 | Mass M |
|---|---|---|---|---|---|---|
| 37 | 4-chloro-N-[(5-{[4-(2,4-difluorobenzoyl)piperidin-1-yl]sulfonyl}thien-2-yl)methyl]benzamide | 14.72 | 95 | b | 539 | 537 |
| 38 | methyl 5-{4-[(5-{[(4-chlorobenzoyl)amino]methyl}thien-2-yl)sulfonyl]piperazin-1-yl}-7-(trifluoromethyl)thieno[3,2-b]pyridine-3-carboxylate | 16.13 | 93 | b | 659 | 657 |
| 39 | ethyl 2-{4-[(5-{[(4-chlorobenzoyl)amino]methyl}-thien-2-yl)sulfonyl]piperazin-1-yl}-5-cyano-6-methylnicotinate | 14.97 | 89 | b | 588 | 586 |
| 40 | 4-chloro-N-{[5-({4-[5-cyano-4,6-bis(dimethyl-amino)pyridin-2-yl]piperazin-1-yl}sulfonyl)thien-2-yl]methyl}benzamide | 12.79 | 85 | b | 588 | 586 |
| 41 | 4-chloro-N-{[5-({4-[6-methyl-2-(trifluoromethyl)-quinolin-4-yl]piperazin-1-yl}sulfonyl)thien-2-yl]methyl}benzamide | 15.88 | 96 | b | 609 | 607 |
| 42 | tert-butyl 4-[(5-{[(4-chlorobenzoyl)amino]-methyl}thien-2-yl)sulfonyl]piperazine-1-carboxylate | 14.04 | 94 | b | 500 | 498 |
| 43 | 2-{4-[(5-{[(4-chlorobenzoyl)amino]methyl}thien-2-yl)sulfonyl]piperazin-1-yl}-8-ethyl-5-oxo-5,8-dihydropyrido[2,3-d]pyrimidine-6-carboxylic acid | 12.9 | 73 | b | 617 | 615 |
| 44 | 7-{4-[(5-{[(4-chlorobenzoyl)amino]methyl}thien-2-yl)sulfonyl]piperazin-1-yl}-1-ethyl-6-fluoro-4-oxo-1,4-dihydro[1,8]naphthyridine-3-carboxylic acid | 13.05 | 87 | b | 634 | 632 |
| 45 | 7-{4-[(5-{[(4-chlorobenzoyl)amino]methyl}thien-2-yl)sulfonyl]piperazin-1-yl}-1-ethyl-6-fluoro-4-oxo-1,4-dihydroquinoline-3-carboxylic acid | 13.1 | 96 | b | 633 | 631 |
| 46 | 4-chloro-N-[(5-{[4-(2,3-dihydro-1,4-benzodioxin-2-ylcarbonyl)piperazin-1-yl]sulfonyl}thien-2-yl)methyl]benzamide | 13.5 | 95 | b | 562 | 560 |
| 47 | 4-chloro-N-{[5-({4-[(2E)-3-phenylprop-2-enyl]-piperazin-1-yl}sulfonyl)thien-2-yl]methyl}-benzamide | 10.65 | 93 | b | 516 | 514 |
| 48 | 4-chloro-N-[(5-{[4-(3-phenylpropyl)piperazin-1-yl]sulfonyl}thien-2-yl)methyl]benzamide | 10.61 | 97 | b | 518 | 516 |
| 49 | 4-chloro-N-[(5-{[4-(3,4,5-trimethoxyphenyl)-piperazin-1-yl]sulfonyl}thien-2-yl)methyl]-benzamide | 13.16 | 90 | b | 566 | 564 |
| 50 | N-[(5-{[4-(4-tert-butylbenzyl)piperazin-1-yl]-sulfonyl}thien-2-yl)methyl]-4-chlorobenzamide | 11.81 | 95 | b | 546 | 544 |
| 51 | 4-chloro-N-[(5-{[4-(4-fluorophenyl)piperazin-1-yl]sulfonyl}thien-2-yl)methyl]benzamide | 14.93 | 90 | b | 494 | 492 |
| 52 | 4-chloro-N-[(5-{[4-(2-hydroxyphenyl)piperazin-1-yl]sulfonyl}thien-2-yl)methyl]benzamide | 12.1 | 93 | b | 492 | 490 |
| 53 | 4-chloro-N-{[5-({4-[4-(trifluoromethyl)pyridin-2-yl]piperazin-1-yl}sulfonyl)thien-2-yl]methyl}benzamide | 14.42 | 91 | b | 545 | 543 |
| 54 | 4-chloro-N-[(5-{[4-(5-cyanopyridin-2-yl)piperazin-1-yl]sulfonyl}thien-2-yl)methyl]benzamide | 13.15 | 94 | b | 502 | 500 |
| 55 | tert-butyl 1-[(5-{[(4-chlorobenzoyl)amino]-methyl}thien-2-yl)sulfonyl]piperidin-4-ylcarbamate | 13.77 | 98 | b | 514 | 512 |
| 56 | 4-chloro-N-({5-[(4-phenylpiperazin-1-yl)sulfonyl]-thien-2-yl}methyl)benzamide | 14.18 | 94 | b | 476 | 474 |
| 57 | 4-chloro-N-{[5-(piperidin-1-ylsulfonyl)thien-2-yl]methyl}benzamide | 13.13 | 96 | b | 399 | 397 |
| 58 | 4-chloro-N-[(5-{[4(1-naphthyl)piperazin-1-yl]sulfonyl}thien-2-yl)methyl]benzamide | 16.38 | 75 | b | 526 | 524 |
| 59 | 4-chloro-N-[(5-{[4-(3,4-dichlorophenyl)piperazin-1-yl]sulfonyl}thien-2-yl)methyl]benzamide | 16.48 | 81 | b | 545 | 543 |
| 60 | 4-chloro-N-{[5-({4-[3-(trifluoromethyl)phenyl]-piperazin-1-yl}sulfonyl)thien-2-yl]methyl}-benzamide | 15.86 | 93 | b | 544 | 542 |
| 61 | 4-chloro-N-{[5-({3-hydroxy-4-[3-(trifluoromethyl)-phenyl]piperidin-1-yl}sulfonyl)thien-2-yl]methyl}-benzamide | 14.79 | 95 | b | 559 | 557 |
| 62 | 4-chloro-N-[(5-{[4-(2-methylphenyl)piperazin-1-yl]sulfonyl}thien-2-yl)methyl]benzamide | 15.64 | 79 | b | 490 | 488 |
| 63 | N-[(5-{[(1R,4R)-5-benzyl-2,5-diazabicyclo[2.2.1]-hept-2-yl]sulfonyl}thien-2-yl)methyl]-4-chloro-benzamide | 9.51 | 97 | b | 502 | 500 |
| 64 | N-[(5-{[4-(benzyloxy)piperidin-1-yl]sulfonyl}thien-2-yl)methyl]-4-chlorobenzamide | 15.08 | 93 | b | 505 | 503 |
| 65 | 4-chloro-N-[(5-{[4-(2-chlorodibenzo[b,f][1,4]-oxazepin-11-yl)piperazin-1-yl]sulfonyl}thien-2-yl)methyl]benzamide | 12.86 | 94 | b | 627.5 | 625.6 |
| 66 | N-(4-chlorophenyl)-2-(5-{[4-(2-oxo-2,3-dihydro-1H-benzimidazol-1-yl)piperidin-1-yl]sulfonyl}thien-2-yl)acetamide | 12.76 | 84 | b | 531 | 529 |

-continued

| Example | Name | Rt HPLC | Purity | Gradient HPLC | Mass M + 1 | Mass M |
|---|---|---|---|---|---|---|
| 67 | 4-chloro-N-({5-[(4-hydroxypiperidin-1-yl)sulfonyl]-thien-2-yl}methyl)benzamide | 10.35 | 95 | b | 415 | 413 |
| 68 | N-[(5-{[4-(4-acetylphenyl)piperazin-1-yl]solfonyl}-thien-2-yl)methyl]-4-chlorobenzamide | 13.15 | 96 | b | 518 | 516 |
| 69 | 4-chloro-N-[(5-{[4-(3,5-dichloropyridin-4-yl)-piperazin-1-yl]sulfonyl}thien-2-yl)methyl]-benzamide | 13.89 | 92 | b | 546 | 544 |
| 70 | 4-chloro-N-[(5-{[4-(3-methoxyphenyl)pipenzin-1-yl]sulfonyl}thien-2-yl)methyl]benzamide | 14.24 | 89 | b | 506 | 504 |
| 71 | N-({5-[(4-benzyl-4-hydroxypiperidin-1-yl)sulfonyl]thien-2-yl}methyl)-4-chlorobenzamide | 13.72 | 92 | b | 505 | 503 |
| 72 | N-{[5-({4-[(2-tert-butyl-1H-indol-5-yl)amino]-piperidin-1-yl}sulfony)thien-2-yl]methyl}-4-chlorobenzamide | 11.55 | 97 | b | 585 | 583 |
| 73 | 4-chloro-N-{[5-({4-[(phenylacetyl)amino]piperidin-1-yl}sulfonyl)thien-2-yl]methyl}benzamide | 12.61 | 88 | b | 532 | 530 |
| 74 | 4-chloro-N-[(5-{[4-(tetrahydrofuran-2-ylcarbonyl)-piperazin-1-yl]sulfonyl}thien-2-yl)methyl]-benzamide | 10.87 | 94 | b | 498 | 496 |
| 75 | 4-chloro-N-[(5-{[4-(6-chloropyridin-2-yl)piperazin-1-yl]sulfonyl}thien-2-yl)methyl]benzamide | 14.93 | 95 | b | 511 | 509 |
| 76 | 4-chloro-N-[(5-{[4-(4-chlorophenyl)piperazin-1-yl]sulfonyl}thien-2-yl)methyl]benzamide | 15.49 | 91 | b | 510 | 508 |
| 77 | N-[(5-{[4-(2H-1,2,3-benzotriazol-2-yl)piperidin-1-yl]sulfonyl}thien-2-yl)methyl]-4-chlorobenzamide | 6.57 | 89 | a | 516 | 514 |
| 78 | 4-chloro-N-[(5-{[4-(4-chlorobenzoyl)piperidin-1-yl]sulfonyl}thien-2-yl)methyl]benzamide | 6.99 | 92.1 | b | 537 | 535 |
| 79 | 4-chloro-N-({5-[(4-phenoxypiperidin-1-yl)sulfonyl]thien-2-yl}methyl)benzamide | 6.81 | 72 | a | 491 | 489 |
| 80 | N-{[5-({4-[benzyl(methyl)amino]piperidin-1-yl}sulfonyl)thien-2-yl]methyl}-4-chlorobenzamide | 4.93 | 93.3 | a | 518 | 516 |
| 81 | 4-chloro-N-{[5-({4-[3-(2,4-dichlorophenyl)-1H-pyrazol-5-yl]piperidin-1-yl}sulfonyl)thien-2-yl]methyl}benzamide | 6.89 | 92.6 | a | 609 | 607 |
| 82 | 4-chloro-N-[(5-{[4-(5-thien-2-yl-1H-pyrazol-3-yl)piperidin-1-yl]sulfonyl}thien-2-yl)methyl]benzamide | 5.93 | 93.8 | a | 547 | 545 |
| 83 | 4-chloro-N-[(5-{[4-(2,3,4,5,6-pentamethylbenzoyl)-piperidin-1-yl]sulfonyl}thien-2-yl)methyl]-benzamide | 7.48 | 90.6 | a | 573 | 571 |
| 84 | 4-chloro-N-[(5-{[4-(phenylacetyl)-1,4-diazepan-1-yl]sulfonyl}thien-2-yl)methyl]benzamide | 5.83 | 94.5 | a | 532 | 530 |
| 85 | 4-chloro-N-{[5-({4-[5-(4-methoxyphenyl)-1H-pyrazol-3-yl]piperidin-1-yl}sulfonyl)thien-2-yl]methyl}benzamide | 5.72 | 92.7 | a | 571 | 499 |
| 86 | N-({5-[(4-anilinopiperidin-1-yl)sulfonyl]thien-2-yl}methyl)-4-chlorobenzamide | 4.84 | 91 | a | 490 | 488 |
| 87 | 4-chloro-N-[(5-{[4-(3-phenyl-1,2,4-thiadiazol-5-yl)piperazin-1-yl]sulfonyl}thien-2-yl)methyl]-benzamide | 6.76 | 98.7 | a | 560 | 558 |
| 88 | 4-chloro-N-[(5-{[4-(2-phenylethyl)piperidin-1-yl]sulfonyl}thien-2-yl)methyl]benzamide | 7.62 | 99 | a | 503 | 501 |
| 89 | 4-chloro-N-({5-[(4-heptylpiperazin-1-yl)sulfonyl]thien-2-yl}methyl)benzamide | 5.29 | 99.1 | a | 498 | 496 |
| 90 | 4-chloro-N-({5-[(4-octylpiperazin-1-yl)sulfonyl]-thien-2-yl}methyl)benzamide | 5.59 | 97.8 | a | 512 | 510 |

[1]HPLC conditions: C8 Symmetry a- MeCN, 0.09% TFA, 0 to 100% (10 min)
HPLC conditions: C18 b- MeCN, 0.09% TFA, 0 to 100% (20 min), c- MeCN, 0.09% TFA, 0 to 100% (30 min).
[2]Mass spectrum APCI

Example 91

Preparation of N-[(5-{[4-(1H-1,2,3-benzotriazol-1-yl)piperidin-1-yl]sulfonyl}thien-2-yl)methyl]-4-chlorobenzamide 91

4-1H-1,2,3-benzotriazol-1-yl)piperidinium trifluoroacetate, 91a

To a solution of Boc-4-hydroxy-piperidine (201 mg, 1 mmol), Benzotriazole (238 mg, 2 mmol) and Triphenylphosphine (523 mg, 2 mmol) in 15 mL THF was added a solution of Diethylazodicarboxylate (326 ul, 2 mmol) in 10 mL THF.

The yellow solution was stirred overnight, the solvent was evaporated to dryness and the crude residue was eluted on silica gel (AcOEt/cyclohexane 7:3). The fractions were isolated containing the 1- and 2-regiosomers.

Fraction 1 contained the 2-benzotriazole-piperidine isomer (250 mg, 82%). $^1$H NMR (CDCl$_3$) δ 7.84 (m, 2H), 738 (m, 2H), 4.90 (quint, J=6.8 Hz.), 4.20 (m, 2H), 3.09 (m, 2H), 2.27 (m, 4H), 1.68 (s, 9H). M/Z APCI: 303.2 (M+1), 247 (M-$^t$butyl+1), 203 (M-Boc+1).

Fraction 2 contained the 1-benzotriazole-piperidine isomer (50 mg, 16%): $^1$H NMR (CDCl$_3$) δ 8.06 (d, J=8.3 Hz., 1H), 7.92 (d, J=83 Hz, 1H), 7.58 (t, J=8.3 Hz.), 7.42 (t, J=8.3

Hz.), 5.25 (m, 1H), 3.52 (m, 2H), 3.20 (m, 2H), 2.55-2.25 (m, 4H), 1.66 (s, 9H). M/Z APCI: 303.2 (M+1), 247 (M-$^t$butyl+1), 203 (M-Boc+1).

91a (250 mg, 0.82 mmol) was dissolved in 5 mL CH$_2$Cl$_2$. 1 mL of TFA was added dropwise and the solution was stirred for 3 h. The solvents were evaporated to dryness and the oily residue was precipitated with diethylether to give 240 mg (95%) of XXI: $^1$H NMR (DMSO-d6) δ 9.10 (b, m, 1H), 8.72 (b, m, 1H), 8.07 (d, J=8.3 Hz., 1H), 7.96 (d, J=8.3 Hz, 1H), 7.55 (t, J=8.3 Hz.), 7.40 (t, J=8.3 Hz.), 5.25 (m, 1H), 3.52 (m, 2H), 3.20 (m, 2H), 2.55-2.25 (m, 4H), M/Z APCI: 203.2 (M+1).

N-[(5-{[4-(1H-1,2,3-benzotriazol-1-yl)piperidin-1-yl]sulfonyl}thien-2-yl)methyl]-4-chlorobenzamide 91

91 was synthesised according to the protocol for the synthesis of 2. After flash chromatography the main fractions were recrystallized from CH$_2$Cl$_2$/Cyclohexane. Isolated yield: 3.1 g (71%). mp.: 174-175° C. $^1$H NMR (DMSO-d6) δ 9.41 (t, J=6.0 Hz, 1H), 8.03 (d, J=7.9 Hz, 1H), 7.91 (d, J=8.7 Hz, 2H), 7.87 (d, J=8.7 Hz, 1H), 7.61-7.54 (m, 3H), 7.52 (t, J=8.3 Hz, 1H), 7.39 (t, J=8.3 Hz, 1H), 7.23 (d, J=3.77 Hz, 1H)), 5.01 (m, 1H), 4.70 (d, J=5.6 Hz, 2H), 3.78 (d, J=10.6 Hz, 2H), 2.80-2.64 (m, 2H), 2.34-2.17 (m, 4H). M/Z APCI: 516.2 (M+1), 514.1 (M−1). C$_{23}$H$_{22}$ClN$_5$O$_3$S$_2$ Calc.: C, 53.53%. H, 4.30%. N, 13.57%. Found: C, 52.74%, H, 4.29%, N, 13.26%.

Alternatively 3 can be synthesised in a parallel solution phase approach using the protocol applied for 2.

The following compounds were prepared on a parallel fashion according to the examples described above The following table provides HPLC data and mass spectroscopy data of the mentioned examples

| Example | Name | Rt HPLC | Purity | Gradient HPLC | Mass M + 1 | Mass M |
|---|---|---|---|---|---|---|
| 92 | 2-(5-{[4-(1H-1,2,3-benzotriazol-1-yl)piperidin-1-yl]sulfonyl}thien-2-yl)-N-(4-chlorophenyl)-acetamide | 6.37 | 91 | a | 516 | 514 |
| 93 | 2-{1-[(5-{[(4-chlorobenzoyl)amino]methyl}thien-2-yl)sulfonyl]piperidin-4-yl}-2H-1,2,3-benzotriazole-5-carboxylic acid | 5.62 | 100 | a | | |
| 94 | 4-chloro-N-[(5-{[4-(5-chloro-1H-1,2,3-benzotriazol-1-yl)piperidin-1-yl]sulfonyl}thien-2-yl)methyl]benzamide | 6.46 | 99 | a | 550 | 548 |
| 95 | methyl 1-{1-[(5-{[(4-chlorobenzoyl)amino]methyl}-thien-2-yl)sulfonyl]piperidin-4-yl}-1H-1,2,3-benzotriazole-5-carboxylate | 6.19 | 83.7 | a | 574 | 572 |
| 96 | methyl 1-{1-[(5-{[(4-chlorobenzoyl)amino]methyl}-thien-2-yl)sulfonyl]piperidin-4-yl}-1H-1,2,3-benzotriazole-6-carboxylate | 6.18 | 90.5 | a | 574 | 572 |
| 97 | methyl 2-{1-[(5-{[(4-chlorobenzoyl)amino]methyl}-thien-2-yl)sulfonyl]piperidin-4-yl}-2H-1,2,3-benzotriazole-5-carboxylate | 6.51 | 94.5 | a | 574 | 572 |
| 98 | 4-chloro-N-[(5-{[4-(6-chloro-1H-1,2,3-benzotriazol-1-yl)piperidin-1-yl]sulfonyl}thien-2-yl)methyl]-benzamide | 6.53 | 96 | a | 550 | 548 |
| 99 | 4-chloro-N-{[5-({4-[5-(trifluoromethyl)-1H-1,2,3-benzotriazol-1-yl]piperidin-1-yl}sulfonyl)thien-2-yl]methyl}benzamide | 6.85 | 94.3 | a | 584 | 582 |
| 100 | N-[(5-{[4-(7-aza-1H-benzimidazol-1-yl)piperidin-1-yl]sulfonyl}thien-2-yl)methyl]-4-chlorobenzamide | 4.5 | 97.6 | a | 0 | 514 |
| 101 | 1-{1-[(5-{[(4-chlorobenzoyl)amino]methyl}thien-2-yl)sulfonyl]piperidin-4-yl}-1H-1,2,3-benzotriazole-5-carboxylic acid | 5.46 | 95.5 | a | 0 | 0 |
| 102 | 1-{1-[(5-{[(4-chlorobenzoyl)amino]methyl})thien-2-yl)sulfonyl]piperidin-4-yl}-1H-1,2,3-benzotriazole-6-carboxylic acid | 5.36 | 97.9 | a | 0 | 0 |
| 103 | N-[(5-{[4-(2-amino-9H-purin-9-yl)piperidin-1-yl]sulfonyl}thien-2-yl)methyl]-4-chlorobenzamide | 4.07 | 94.6 | a | 532 | 530 |
| 104 | 4-chloro-N-[(5-{[4-(9H-purin-9-yl)piperidin-1-yl]sulfonyl}thien-2-yl)methyl]benzamide | 4.67 | 98.4 | a | 517 | 515 |
| 105 | N-[(5-{[4-(6-amino-9H-purin-9-yl)piperidin-1-yl]sulfonyl}thien-2-yl)methyl]-4-chlorobenzamide | 4.15 | 91.7 | a | 532 | 530 |
| 106 | 4-chloro-N-({5-[(4-{6-nitro-1H-benzimidazol-1-yl}piperidin-1-yl)sulfonyl]thien-2-yl}methyl)benzamide | 5.31 | 67 | a | 0 | 558 |
| 107 | 4-chloro-N-({5-[(4-{5-nitro-1H-benzimidazol-1-yl}piperidin-1-yl)sulfonyl]thien-2-yl}methyl)-benzamide | 5.46 | 86.6 | a | 560 | 558 |
| 108 | 4-chloro-N-[(5-{[4-(2H-1,2,3-triazol-2-yl)piperidin-1-yl]sulfonyl}thien-2-yl)methyl]benzamide | 5.77 | 96.8 | a | 466 | 464 |
| 109 | N-[(5-{[4-(1H-benzimidazol-1-yl)piperidin-1-yl]sulfonyl}thien-2-yl)methyl]-4-chlorobenzamide | 4.43 | 99 | a | 515 | 513 |

Example 110

Preparation of 4-chloro-N-{[5-({4-[3-propylanilino]piperidin-1-yl}sulfonyl)thien-2-yl]methyl}benzamide 110

4-(3-propylanilino)piperidine trifluoroacetate salt, 110b

Boc-piperidin-4-one (2.5 g, 12.5 mmol) and 3-propylaniline hydrochloride (2.15 g, 12.5 mmol) and 2.1 ml, DIEA were stirred in 15 mL DCE for 1 h. To this solution acetic acid (750 ul, 12.5 mmol) and sodium triacetoxyborohydride (3.72 g, 17.6 mmol) were added and the solution was stirred overnight under Ar. The reaction mixture was diluted with diethylether, and 12 mL of NaOH (2N) were added (pH9-10). The organic phase was to washed twice with brine and dried over $MgSO_4$. The crude was purified by flash chromatography on silica gel using petroleum ether/EtOAc 7:1 as eluant. 3.7 g (94%) of pure 110a were isolated as a colorless solid. $^1$H NMR (DMSO-d6) δ 6.93 (t, J=7.7, 1H), 6.31-6.39 (m, 3H), 531 (d, J=8.2, 1H), 3.84 (d, J=13.2 Hz, 2H), 3.33 (m, 1H.), 2.89 (m, 2H), 239 (t, J=7.7 Hz, 2H), 1.84 (d J=113 Hz, 2H), 1.55 (m, 2H), 1.51 (s, 9H), 1.20 (m, 2H), 0.86 (t, J=73 Hz, 3H), M/Z ESI: 319.2 (M+1).

110a (1.5 g, 4.71 mmol) was dissolved in 20 mL $CH_2Cl_2$. 5 mL of TFA were added dropwise and the solution was stirred for 3 h. The solvents were evaporated to dryness and the oily residue was precipitated with diethylether to give 1.45 g (92%) of 110b. $^1$H NMR (DMSO-d6) S8.59 (m, 2H), 7.00 (t, J=7.7, 1H), 6.44-6.50 (m, 3H), 3.51 (m, to 1H), 3.27 (m, 2H), 3.00 (m, 2H), 2.42 (t, J=7.7 Hz, 2H), 2.00 (d J=11.3 Hz, 2H), 1.57-1.47 (m, 4H), 0.87 (t, J=73 Hz, 3H), M/Z ESI: 219.2 (M+1).

4-chloro-N-{[5-({4-[3-propylanilino]piperidin-1-yl}sulfonyl)thien-2-yl]methyl}-benzamide 110

110 was synthesised according to the protocol for the synthesis of 2. After flash chromatography the main fractions were recrystallized from $CH_2Cl_2$/Cyclohexane. Isolated yield: 430 mg (56%). mp.: 169-170° C. $^1$H NMR (DMSO-d6) δ 9.36 (t, J=5.8 Hz, 1H), 7.89 (d, J=8.7 Hz, 2H), 7.56 (d, J=8.7 Hz, 2H), 7.47 (d, J=3.8 Hz, 1H), 7.19 (d, J=3.8 Hz, 1H), 6.90 (t, J=7.5 Hz, 1H), 6.49-6.42 (m, 3H), 5.33 (d, J=7.9 Hz, 1H), 4.68 (d, J=5.6 Hz, 2H), 3.51 (d, J=11.7 Hz, 2H), 3.29 (m, 1H), 2.55 (t, J=10.5 Hz, 2H), 2.36 (t, J=7.3 Hz, 2H), 1.97 (d, J=10.9 Hz, 2H). 136-137 (m, 4H), 0.84 (t, J=7.3 Hz, 3H). M/Z APCI: 532.2 (M+1), 530.1 (M−1). $C_{26}H_{30}ClN_3O_3S_2$ Calc.: C, 58.70%. H, 5.68%. N, 7.90%. Found: C, 58.55%, H, 5.67%, N, 7.93%.

Alternatively 110 can be synthesised in a parallel solution phase approach:

In a 4 ml Alltech® tube 1 eq. of piperidine trifluoracetate salt is shaked with polymerbound NMM (4 eq.) in 1.2 mL $CH_2Cl_2$/DMF. After 15 min 1 mL of a stock solution of 1b in $CH_2Cl_2$/DMF (1.2 eq.) is added and the reaction slurry is shaked. After 3 h Aminomethyl Merryfield resin (0.4 eq) is added and the reaction is shaked overnight. Occasionally remaining amine is removed with polymerbound isocyanate (0.2 eq.). The slurry is again shaked for 1 h. The solution is filtered off, the resins are washed 3× with $CH_2Cl_2$, and the solvents are evaporated at medium temperature in a Savant Speed Vac® Plus vacuum centrifuge for 1 h.

The following compounds were prepared on a parallel fashion according to the examples described above The following table provides HPLC data and mass spectroscopy data of the mentioned examples

| Example | Name | Rt HPLC | Purity | Gradient HPLC | Mass M + 1 | Mass M |
|---|---|---|---|---|---|---|
| 111 | 4-chloro-N-{[5-({4-[3-(trifluoromethyl)anilino]-piperidin-1-yl}sulfonyl)thien-2-yl]methyl}-benzamide | 7.4 | 96 | a | 558 | 556 |
| 112 | 4-chloro-N-{[5-({4-[3-(dimethylamino)anilino]-piperidin-1-yl}sulfonyl)thien-2-yl]methyl}-benzamide | 4.86 | 94.8 | a | 533 | 531 |
| 113 | methyl 3-({1-[(5-{[(4-chlorobenzoyl)amino]-methyl}thien-2-yl)sulfonyl]piperidin-4-yl}amino)-benzoate | 6.33 | 96.6 | a | 548 | 546 |
| 114 | 4-chloro-N-{[5-({4-[3-(methylsulfanyl)anilino]-piperidin-1-yl}sulfonyl)thien-2-yl]methyl}-benzamide | 6.07 | 97.4 | a | 536 | 534 |
| 115 | 4-chloro-N-({5-[(4-{3-nitroanilino}piperidin-1-yl)sulfonyl]thien-2-yl}methyl)benzamide | 6.93 | 88.3 | a | 535 | 533 |
| 116 | 4-chloro-N-[(5-{[4-(2-methoxyanilino)piperidin-1-yl]sulfonyl}thien-2-yl)methyl]benzamide | 5.12 | 96.2 | a | 520 | 518 |
| 117 | 3-({1-[(5-{[(4-chlorobenzoyl)amino]methyl}thien-2-yl)sulfonyl]piperidin-4-yl}amino)benzamide | 4.52 | 69 | a | 533 | 531 |
| 118 | 4-chloro-N-{[5-({4-[2-(trifluoromethyl)anilino]-piperidin-1-yl}sulfonyl)thien-2-yl]methyl}-benzamide | 7.7 | 97.5 | a | 558 | 556 |
| 119 | 4-chloro-N-({5-[(4-{2-nitro-4-[(trifluoromethyl)-sulfonyl]anilino)piperidin-1-yl)sulfonyl]thien-2-yl}methyl)benzamide | 7.55 | 84.8 | a | 667 | 665 |
| 120 | 4-chloro-N-[(5-{[4-(4-chloroanilino)piperidin-1-yl]sulfonyl}thien-2-yl)methyl]benzamide | 6.6 | 86.2 | a | 524 | 522 |
| 121 | 4-chloro-N-{[5-({4-[4-(trifluoromethyl)anilino]-piperidin-1-yl}sulfonyl)thien-2-yl]methyl}-benzamide | 7.45 | 96.8 | a | 558 | 556 |
| 122 | 4-chloro-N-({5-[(4-{4-[(trifluoromethyl)sulfonyl]-anilino}piperidin-1-yl)sulfonyl]thien-2-yl}methyl)-benzamide | 7.3 | 95.5 | a | 622 | 620 |
| 123 | 4-chloro-N-({5-[(4-{2-nitroanilino}piperidin-1-yl)sulfonyl]thien-2-yl}methyl)benzamide | 7.13 | 92.8 | a | 535 | 533 |

-continued

| Example | Name | Rt HPLC | Purity | Gradient HPLC | Mass M + 1 | Mass M |
|---|---|---|---|---|---|---|
| 124 | N-{[5-({4-[4-(aminocarbonyl)anilino]piperidin-1-yl}sulfonyl)thien-2-yl]methyl}-4-chlorobenzamide | 4.9 | 74 | a | 533 | 531 |
| 125 | 4-chloro-N-{[5-({4-[4-(1,3-dithiolan-2-yl)anilino]-piperidin-1-yl}sulfonyl)thien-2-yl]methyl}-benzamide | 6.2 | 94.2 | a | 594 | 0 |
| 126 | N-[(5-{[4-(3-chloroanilino)piperidin-1-yl]sulfonyl}-thien-2-yl)methyl]-3-nitrobenzamide | 6.68 | 97.8 | a | 535 | 533 |
| 127 | 4-chloro-N-[(5-{[4-(3-chloroanilino)piperidin-1-yl]sulfonyl}thien-2-yl)methyl]benzamide | 7.06 | 93.9 | a | 524 | 522 |
| 128 | 4-chloro-N-[(5-{[4-(3-methoxyanilino)piperidin-1-yl]sulfonyl}thien-2-yl)methyl]benzamide | 5.4 | 92 | a | 519 | 517 |
| 129 | 4-chloro-N-{[5-({4-[3-(methylsulfonyl)anilino]-piperidin-1-yl}sulfonyl)thien-2-yl]methyl}-benzamide | 6.06 | 91.7 | a | 568 | 566 |
| 130 | N-({5-[(4-{3-[amino(imino)methyl]anilino}-piperidin-1-yl)sulfonyl]thien-2-yl}methyl)-4-chlorobenzamide | 4.3 | 91.4 | a | 532 | 530 |
| 131 | 4-chloro-N-({5-[(4-{3-[(2-hydroxyethyl)sulfonyl]-anilino}piperidin-1-yl)sulfonyl]thien-2-yl}methyl)-benzamide | 5.16 | 92.3 | a | 598 | 596 |
| 132 | N-[(5-{[4-(2-aminoanilino)piperidin-1-yl]sulfonyl}-thien-2-yl)methyl]-4-chlorobenzamide | 4.63 | 78 | a | 506 | 504 |
| 133 | 4-chloro-N-[(5-{[4-(2-hydroxyanilino)piperidin-1-yl]sulfonyl}thien-2-yl)methyl]benzamide | 4.47 | 94.3 | a | 506 | 504 |
| 134 | 4-chloro-N-[(5-{[4-(4-hydroxyanilino)piperidin-1-yl]sulfonyl}thien-2-yl)methyl]benzamide | 4.3 | 86.8 | a | 506 | 504 |
| 135 | 4-chloro-N-({5-[(4-{3-[(trifluoromethyl)sulfanyl]-anilino}piperidin-1-yl)sulfonyl]thien-2-yl}methyl)-benzamide | 7.1 | 89.1 | a | 590 | 588 |
| 136 | 4-chloro-N-[(5-{[4-(3-toluidino)piperidin-1-yl]sulfonyl}thien-2-yl)methyl]benzamide | 4.73 | 85.3 | a | 504 | 502 |
| 137 | 4-chloro-N-({5-[(4-{[3-chloro-5-(trifluoromethyl)pyridin-2-yl]amino}piperidin-1-yl)sulfonyl]thien-2-yl}methyl)benzamide | 7.58 | 99 | a | 593 | 591 |
| 138 | 4-chloro-N-{[5-({4[3-(1,3-oxazol-5-yl)anilino]-piperidin-1-yl}sulfonyl)thien-2-yl]methyl}-benzamide | 5.68 | 86.5 | a | 557 | 555 |
| 139 | N-[(5-{[4-(3-tert-butylanilino)piperidin-1-yl]sulfonyl}thien-2-yl)methyl]-4-chlorobenzamide | 5.77 | 98 | a | 546 | 544 |
| 140 | 4-chloro-N-[(5-{[4-(2-propylanilino)piperidin-1-yl]sulfonyl}thien-2-yl)methyl]benzamide | 6.42 | 96.1 | a | 532 | 530 |
| 141 | 4-chloro-N-{[5-({4-[(2,2-dioxido-1,3-dihydro-2-benzothien-5-yl)amino]piperidin-1-yl}sulfonyl)-thien-2-yl]methyl}benzamide | 5.47 | 95 | a | 580 | 578 |
| 142 | 4-chloro-N-[(5-{[4-(2,3-dihydro-1H-inden-5-ylamino)piperidin-1-yl]sulfonyl}thien-2-yl)methyl]-benzamide | 5.15 | 97.4 | a | 530 | 528 |
| 143 | 4-chloro-N-[(5-{[4-(4-propylanilino)piperidin-1-yl]sulfonyl}thien-2-yl)methyl]benzamide | 5.49 | 98.7 | a | 532 | 530 |
| 144 | 4-chloro-N-[(5-{[4-({3-nitropyridin-2-yl}amino)-piperidin-1-yl]sulfonyl}thien-2-yl)methyl]-benzamide | 6.62 | 99.3 | a | 537 | 535 |
| 145 | N-{[5-({4-[(3-aminopyridin-2-yl)amino]piperidin-1-yl}sulfonyl)thien-2-yl]methyl}-4-chlorobenzamide | 4.37 | 96.1 | a | 506 | 504 |
| 146 | N-[(5-{[4-([1,1'-biphenyl]-3-ylamino)piperidin-1-yl]sulfonyl}thien-2-yl)methyl]-4-chlorobenzamide | 6.25 | 92.4 | a | 566 | 564 |
| 147 | N-[(5-{[4-(3-benzylanilino)piperidin-1-yl]sulfonyl}thien-2-yl)methyl]-4-chlorobenzamide | 7.29 | 96.1 | a | 589 | 587 |
| 148 | 4-chloro-N-[(5-{[4-(pyrimidin-2-ylamino)piperidin-1-yl]sulfonyl}thien-2-yl)methyl]benzamide | 4.55 | 97.7 | a | 492 | 490 |
| 149 | 4-chloro-N-{[5-({4-[4-(morpholin-4-ylsulfonyl)-anilino]piperidin-1-yl}sulfonyl)thien-2-yl]methyl}-benzamide | 6.2 | 96.2 | a | 639 | 637 |
| 150 | 4-chloro-N-({5-[(4-{[4-(trifluoromethyl)pyrimidin-2-yl]amino}piperidin-1-yl)sulfonyl]thien-2-yl}methyl)benzamide | 6.06 | 94.2 | a | 560 | 558 |
| 151 | 4-chloro-N-[(5-{[4-(3-cyclohexyl-4-hydroxyanilino)piperidin-1-yl]sulfonyl}thien-2-yl)methyl]benzamide | 5.01 | 85.2 | a | 588 | 586 |
| 152 | N-({5-[(4-{3-[(butylamino)sulfonyl]anilino}-piperidin-1-yl)sulfonyl]thien-2-yl}methyl)-4-chlorobenzamide | 6.05 | 99.7 | a | 626 | 624 |
| 153 | 4-chloro-N-[(5-{[4-(3-ethylanilino)piperidin-1-yl]sulfonyl}thien-2-yl)methyl]benzamide | 4.86 | 98.4 | a | 518 | 516 |
| 154 | 4-chloro-N-[(5-{[4-(5,6,7,8-tetrahydronaphthalen-1-ylamino)piperidin-1-yl]sulfonyl}thien-2-yl)methyl]benzamide | 5.36 | 86.9 | a | 544 | 542 |

| Example | Name | Rt HPLC | Purity | Gradient HPLC | Mass M + 1 | Mass M |
|---|---|---|---|---|---|---|
| 155 | N-{[5-({4-[3-(aminosulfonyl)anilino]piperidin-1-yl}sulfonyl)thien-2-yl]methyl}-4-chlorobenzamide | 5.57 | 98.9 | a | 0 | 566 |
| 156 | 4-chloro-N-[(5-{[4-(quinolin-5-ylamino)piperidin-1-yl]sulfonyl}thien-2-yl)methyl]benzamide | 4.57 | 95.8 | a | 541 | 539 |
| 157 | 4-chloro-N-[(5-{[4-(quinolin-8-ylamino)piperidin-1-yl]sulfonyl}thien-2-yl)methyl]benzamide | 5.65 | 97 | a | 541 | 539 |

Example 158

Preparation of 4-Chloro-N-[(5-{[4-(3-propylphenoxy)piperidin-1-yl]sulfonyl}thien-2-yl)methyl]benzamide 158

4-(3-propylphenoxy)piperidinium trifluoroacetate. 158a

To a solution of Boc-4-hydroxy-piperidine (1 g, 4.97 mmol), 3-propylphenol (677 mg, 4.97 mmol) and Triphenylphosphine (1.304 g, 4.97 mmol) in 30 mL THF was added a solution of Diethylazodicarboxylate (866 mg, 4.97 mmol) in 10 mL THY. The yellow solution was stirred overnight, the solvent was evaporated to dryness and the crude residue was eluted on silica gel (AcOEt/cyclohexane 1:9) to provide 880 mg (56%) of pure 158a.

158a was dissolved in 10 mL $CH_2Cl_2$ and 2 mL TFA were added. After 3 h the reaction mixture was evaporated to dryness and the residual oil was precipitated with diethylether to afford 800 mg (92%) of pure TFA salt 158a: $^1H$ NMR (DMSO-d6) δ 8.42 (b, m, 2H), 7.04 (d, J=7.7 Hz, 1H), 6.65 (m, 3H), 4.47 (m, 1H), 320-2.80 (b, m, 4H), 2.46 (m, 2H), 1.90 (m, 2H), 1.65 (m, 2H), 1.43 (m, 2H), 0.74 (t, J=73 Hz, 3H).

4-Chloro-N-[(5-{[4-(3-propylphenoxy)piperidin-1-yl]sulfonyl}thien-2-yl)methyl]-benzamide 158

158 was synthesised according to the protocol for the synthesis of 2. After flash chromatography the main fractions were recrystallized from $CH_2Cl_2$/Cyclohexane. Isolated yield: 24 mg (88%). NMR (DMSO-d6) δ 9.38 (t, J=5.6 Hz, 1H), 7.90 (d, J=8.7 Hz, 2H), 7.56 (d, J=8.7 Hz, 2H), 7.50 (d, J=3.7 Hz, 1H), 7.19 (d, J=3.7 Hz, 1H), 7.09 (t, J=8.1 Hz, 1H), 6.85-6.66 (m, 3H), 4.68 (d, J=5.6 Hz, 2H), 3.51 (d, J=11.7 Hz, 2H), 3.29 (m, 1H), 2.87 (t, J=10.5 Hz, 2H), 2.45 (t, J=73 Hz, 2H), 2.00 (d, J=10.9 Hz, 2H). 1.56-1.37 (m, 4H), 0.84 (t, J=7.2 Hz, 3H). M/Z APCI: 533.2 (M+1), 531.1 (M−1).

Protocol #2

Example 159

Preparation of 4-chloro-N-{[5-({4-[(2E)-3-phenylprop-2-enoyl]piperazin-1-yl}sulfonyl)thien-2-yl]methyl}benzamide 159

To a stirred solution of 1 (36 mg, 0.09 mmol) and $iPr_2NEt$ (32 μl, 0.189 mmol) in $CHCl_3$ (2 mL) was added [(2E)-3-phenylprop-2-enoyl]chloride (15 mg, 0.09 mmol). After 4 h the reaction mixture was washed with HCl (1 N) and sat. NaCl solution, and dried over $MgSO_4$. The solvent was evaporated and the residue was filtered through silica gel using AcOEt/MeOH 1% as eluent to afford 159 as white solid (10 mg, 20%). M/Z APCI: 531.2 (M+1), 529.1 (M−1). Anal. HPLC: rt.=6.18 min (method a).

The following compounds were prepared on a parallel fashion according to the examples described above The following table provides HPLC data and mass spectroscopy data of the mentioned examples

| Example | Name | Rt HPLC | Purity | Gradient HPLC | Mass M + 1 | Mass M |
|---|---|---|---|---|---|---|
| 160 | 4-chloro-N-({5-[(4-{4-nitrobenzoyl}piperazin-1-yl)sulfonyl]thien-2-yl}methyl)benzamide | 12.75 | 96 | b | 549 | 547 |
| 161 | N-({5-[(4-benzoylpiperazin-1-yl)sulfonyl]thien-2-yl}methyl)-4-chlorobenzamide | | 85 | b | 504 | 502 |
| 162 | 4-chloro-N-{[5-({4-[4-(trifluoromethyl)benzoyl]-piperazin-1-yl}sulfonyl)thien-2-yl]methyl}-benzamide | | 98 | b | 572 | 570 |
| 163 | 4-chloro-N-{[5-({4-[4-(dimethylamino)benzoyl]-piperazin-1-yl}sulfonyl)thien-2-yl]methyl}-benzamide | | 93 | b | 547 | 545 |
| 164 | 4-chloro-N-[(5-{[4-(2-fluorobenzoyl)piperazin-1-yl]sulfonyl}thien-2-yl)methyl]benzamide | | 98 | b | 522 | 520 |
| 165 | 4-chloro-N-[(5-{[4-(2,6-difluorobenzoyl)piperazin-1-yl]sulfonyl}thien-2-yl)methyl]benzamide | | 96 | b | 540 | 538 |
| 166 | 4-chloro-N-[(5-{[4-(3-fluorobenzoyl)piperazin-1-yl]sulfonyl}thien-2-yl)methyl]benzamide | | 93 | b | 522 | 520 |
| 167 | 4-chloro-N-[(5-{[4-(2-naphthoyl)piperazin-1-yl]sulfonyl}thien-2-yl)methyl]benzamide | 13.6 | 90 | b | 554 | 552 |
| 168 | 4-chloro-N-[(5-{[4-(1-naphthoyl)piperazin-1-yl]sulfonyl}thien-2-yl)methyl]benzamide | 13.44 | 93 | b | 554 | 552 |
| 169 | 4-chloro-N-({5-[(4-{2-nitrobenzoyl}piperazin-1-yl)sulfonyl]thien-2-yl}methyl)benzamide | | 12.26 | 87 | b | 549 | 547 |
| 170 | 4-chloro-N-[(5-{[4-(pyridin-3-ylcarbonyl)piperazin-1-yl]sulfonyl}thien-2-yl)methyl]benzamide | 9.17 | 84 | b | 505 | 503 |

-continued

| Example | Name | Rt HPLC | Purity | Gradient HPLC | Mass M + 1 | Mass M |
|---|---|---|---|---|---|---|
| 171 | N-[(5-{[4-(2,1,3-benzoxadiazol-5-ylcarbonyl)piperazin-1-yl]sulfonyl}thien-2-yl)methyl]-4-chlorobenzamide | 12.75 | 99 | b | 546 | 544 |
| 172 | 4-chloro-N-[(5-{[4-(2,4-difluorobenzoyl)piperazin-1-yl]sulfonyl}thien-2-yl)methyl]benzamide | 12.84 | 90 | b | 540 | 538 |
| 173 | 4-chloro-N-[(5-{[4-(2,4,6-trifluorobenzoyl)-piperazin-1-yl]sulfonyl}thien-2-yl)methyl]-benzamide | 13.06 | 89 | b | 558 | 556 |
| 174 | 4-chloro-N-[(5-{[4-(2,6-dichlorobenzoyl)piperazin-1-yl]sulfonyl}thien-2-yl)methyl]benzamide | 13.19 | 95 | b | 574 | 572 |
| 175 | 4-chloro-N-({5-[(4-heptanoylpiperazin-1-yl)sulfonyl]thien-2-yl}methyl)benzamide | 6.35 | 99.4 | a | 512 | 510 |
| 176 | 4-chloro-N-[(5-{[4-(quinolin-8-ylsulfonyl)piperazin-1-yl]sulfonyl}thien-2-yl)methyl]benzamide | 5.86 | 93.6 | a | 591 | 589 |

Protocol #3

Example 177

Preparation of 4-nitro-N-({5-[(4-{3-[(trifluoromethyl)sulfonyl]anilino}-piperidin-1-yl)sulfonyl]thien-2-yl}methylbenzamide 177

{[(3-Nitrobenzoyl)amino]methyl}thiophene-2-sulfonyl chloride 177a

To a solution of 2-Aminomethylthiophene (10.6 mL, 103 mmol) and pyridine (9.1 mL, 104 mmol) in 100 mL of chloroform was added at 0° C. a solution of 3-Nitrobenzoylchloride (19.2 g, 103 mmol) in $CH_2Cl_2$. The reaction was allowed to warm to rt. during 1 h and stirred for additional 3 h. Water was added while 3-Nitro-N-(thien-2-ylmethyl)-benzamide (10.1 g) precipitated. The solid was filtered of and washed with water. The remaining organic layer was washed with brine, dried over $MgSO_4$ and evaporated to dryness to afford additional 3-Nitro-N-(thien-2-ylmethyl)benzamide (15.2 g). The overall yield was 25.3 g (99.9%). 3-Nitro-N-(thien-2-ylmethyl)benzamide was used for the next step without further purification.

Chlorosulfonic acid (5.62 mL, 84 mmol) was dissolved in 20 mL $CH_2Cl_2$ and added to a solution of 3-Nitro-N-(thien-2-ylmethyl)benzamide (11.0 g, 42 mmol) in 100 mL $CH_2Cl_2$ under vigorous stirring. A gummy solid was formed and the reaction mixture was stirred for 3 h. The reaction was quenched with ice, and ice cold NaHCO3 solution was added to reach pH8.5. The aqueous layer was washed twice with $CH_2Cl_2$. Tetrabutylammoniumhydroxide (40% in water) (32 mL, 50 mmol) was added to the aqueous layer, while a solid was formed. The precipitate was extracted into $CH_2Cl_2$ and the aqueous layer was washed 3× with $CH_2Cl_2$. The combined organic layers were dried over $MgSO_4$ and evaporated to dryness to afford a slightly colored foam of Tetrabutylammonium 5-{[(3-Nitrobenzoyl)amino]methyl}thiophene-2-sulfonate (24 g, 97%). NMR spectra indicated pure compound, which was used for the following chlorination step.

To a solution of Tetrabutylammonium 5-{([(3-Nitrobenzoyl)amino]methyl}thiophene-2-sulfonate (2.0 g, 3.4 mmol) in 50 mL $CH_2Cl_2$ was added triphosgene (800 mg, 2.7 mmol, 2.3 eq.), dissolved in 10 mL $CH_2Cl_2$. To this reaction mixture DMF (0.1 mL, 1.4 mmol) was added dropwise during 10', while gas evolution could be observed. The gases were trapped at the outlet of the reaction flask in a 2N NaOH solution. The reaction mixture was stirred for 3 h, and the crude was directly filtered through silica gel using EtOAc/hexane 1:2 as eluent. An orange solid could be isolated which was recrystallised from cyclohexane/$CH_2Cl_2$. 177a (730 mg, 60%) was obtained as colorless needles. $^1$H NMR (CDCl$_3$) δ 8.83 (t, J=1.5 Hz, 1H), 8.35 (t, J=7.5 Hz, 1H), 7.76 (t, J=4.1 Hz, 1H), 7.70-7.58 (m, 3H), 732-7.40 (m, 2H), 7.05 (t, J=3.8 Hz, 1H).

3-Nitro-N-({5-[(4-{3-[(trifluoromethyl)sulfonyl]anilino}piperidin-1-yl)sulfonyl]thien-2-yl}methyl)benzamide 177

A suspension of the sulfonyl chloride 177a (573 mg, 1.58 mmol), 4-(3-trifluoro-methanesulfonyl-phenylamino)-piperidine (490 mg, 138 mmol), and Et$_3$N (330 ul, 2.38 mmol) in $CH_2Cl_2$ (30 mL) was stirred for 3 h at 23° C., whereupon the suspension turned to a clear solution. The standard work-up (HCl 1N; brine; MgSO$_4$) gave the crude product as a yellow foam. This was dissolved in DMSO (1 mL) and CH$_3$CN (3 mL), and injected on a reverse-phase prep. HPLC (C8, gradient H$_2$O:CH$_3$CN 60:40→0:100 over 40 min, retention time=20 min). Freeze-drying of the desired fractions afforded 667 mg (67%) of the title sulfonamide as a pale yellow powder. $^1$H NMR (DMSO-d6) δ 9.69 (t, J=5.8 Hz, 1H), 8.72 (t, J=1.9 Hz, 1H), 8.41 (dd, J=83, 1.9 Hz, 1H), 8.34 (d, J=7.9 Hz, 1H), 7.81 (t, J=8.1 Hz, 1H), 7.50 (d, J=3.8 Hz, 1H), 7.45 (t, J=7.9 Hz, 1H), 7.23 (d, J=3.8 Hz, 1H), 7.15-7.11 (m, 3H), 6.52 (d, J=7.9 Hz, 1H), 4.73 (d, J=5.7 Hz, 2H), 3.57-3.42 (br. d, J=11.7 Hz, 2H), 3.52-3.33 (m, 1H), 2.62 (t, J=10.4 Hz, 2H), 2.00-1.90 (br. d, J=10.6 Hz), 1.43 (qd, Jz: 10.2, 3 Hz, 2H). $^{13}$C NMR (DMSO-d6) 5164.66 (s, C═O), 150.51 (s), 149.32 (s), 148.20 (s), 135.30 (s), 134.22 (s), 134.11 (d), 132.98 (d), 131.49 (d), 130.67 (d), 130.44 (s), 127.00 (d), 126.60 (d), 122.38 (d), 120.41 (d), 119.81 (q, J=326 Hz, CF$_3$), 116.72 (d), 112.79 (d), 47.43 (d), 45.15 (t), 38.58 (t), 30.66 (t). M/Z APCI: 633 (M+1), 631 (M−1). Anal. HPLC: R.t=6.41 min (method a). C$_{24}$H$_{23}$F$_3$N$_4$O$_7$S$_3$ Calc.: C, 45.56%. H, 3.66%. N, 8.86%. Found: C, 45.30%, H, 3.73%, N, 8.85%.

In the here-described sequence, the 3-nitrobenzoyl chloride initially used could be replaced with other acylating reagents, which include (but are not limited to): 4-nitrobenzoyl, 4-chlorobenzoyl chloride, 3-methoxybenzoylchloride, trifluoroacetic anhydride.

The following compounds were prepared on a parallel fashion according to the examples described above The following table provides HPLC data and mass spectroscopy data of the mentioned examples

| Example | Name | Rt HPLC | Purity | Gradient HPLC | Mass M + 1 | Mass M |
|---|---|---|---|---|---|---|
| 178 | N-[(5-{[4-(1H-1,2,3-benzotriazol-1-yl)piperidin-1-yl]sulfonyl}thien-2-yl)methyl]-3-nitrobenzamide | 5.62 | 63.1 | a | 527 | 525 |
| 179 | 4-nitro-N-({5-[(4-{3-[(trifluoromethyl)sulfonyl]-anilino}piperidin-1-yl)sulfonyl]thien-2-yl}methyl)-benzamide | 6.77 | 87.3 | a | 633 | 631 |
| 180 | N-[(5-{[4-(2,4-difluorobenzoyl)piperidin-1-yl]sulfonyl}thien-2-yl)methyl]-4-nitrobenzamide | 6.3 | 92.7 | a | 550 | 548 |
| 181 | N-[(5-{[4-(1H-1,2,3-benzotriazol-1-yl)piperidin-1-yl]sulfonyl}thien-2-yl)methyl]-4-nitrobenzamide | 5.6 | 77.3 | a | 527 | 525 |
| 182 | N-[(5-{[4-(1H-1,2,3-benzotriazol-1-yl)piperidin-1-yl]sulfonyl}thien-2-yl)methyl]-3-nitrobenzamide | 5.62 | 63.1 | a | 527 | 525 |
| 183 | 4-nitro-N-({5-[(4-{3-[(trifluoromethyl)sulfonyl]-anilino}piperidin-1-yl)sulfonyl]thien-2-yl}methyl)-benzamide | 6.77 | 87.3 | a | 633 | 631 |
| 184 | N-[(5-{[4-(2,4-difluorobenzoyl)piperidin-1-yl]-sulfonyl}thien-2-yl)methyl]-4-nitrobenzamide | 6.3 | 92.7 | a | 550 | 548 |
| 185 | N-[(5-{[4-(1H-1,2,3-benzotriazol-1-yl)piperidin-1-yl]sulfonyl}thien-2-yl)methyl]-4-nitrobenzamide | 5.6 | 77.3 | a | 527 | 525 |
| 186 | 3-nitro-N-[(5-{[4-(3-methoxyanilino)piperidin-1-yl]sulfonyl}thien-yl)-methyl]benzamide | 4.86 | 88.3 | a | 533 | 531 |
| 187 | 3-nitro-N-{5-({4-[3-(trifluoromethyl)anilino]-piperidin-1-yl}sulfonyl)thien-2-yl]methyl}-benzamide | 7.03 | 91 | a | 568 | 566 |
| 188 | N-{[5-({4-[3-(dimethylamino)anilino]piperidin-1-yl}sulfonyl)thien-2-yl]methyl}-3-nitrobenzamide | 4.2 | 97.5 | a | 544 | 542 |
| 189 | 3-nitro-N-{[5-({4-[3-(methylsulfonyl)anilino]-piperidin-1-yl}sulfonyl)thien-2-yl]methyl}-benzamide | 5.71 | 91.4 | a | 579 | 0 |
| 190 | 3-nitro-N-{[5-({4-[3-(methylsulfanyl)anilino]-piperidin-1-yl}sulfonyl)thien-2-yl]melhyl}-benzamide | 5.64 | 92.2 | a | 547 | 0 |
| 191 | N-{[5-({4-[3-(aminosulfonyl)anilino]piperidin-1-yl}sulfonyl)thien-2-yl]methyl}-3-nitrobenzamide | 5.32 | 63 | a | 580 | 0 |
| 192 | methyl 3-{[1-({5-[({3-nitrobenzoyl}amino)methyl]-thien-2-yl}sulfonyl)-piperidin-4-yl]amino}benzoate | 5.89 | 88.3 | a | 559 | 557 |
| 193 | N-{[5-({4-[3-(aminocarbonyl)anilino]piperidin-1-yl}sulfonyl)thien-2-yl]methyl}-3-nitrobenzamide | 4.44 | 65.2 | a | 0 | 542 |
| 194 | 3-nitro-N-({5-[(4-{3-nitroanilino}piperidin-1-yl)sulfonyl]thien-2-yl}methyl)benzamide | 6.53 | 88.4 | a | 546 | 544 |
| 195 | 3-nitro-N-[(5-{[4-(2-methoxyanilino)piperidin-1-yl]sulfonyl}thien-2-yl)methyl]benzamide | 4.71 | 86.1 | a | 532 | 530 |
| 196 | 3-nitro-N-{[5-({4-[2-(trifluoromethyl)anilino]-piperidin-l-yl}sulfonyl)thien-2-yl]methyl}-benzamide | 7.23 | 94.5 | a | 569 | 567 |
| 197 | 3-nitro-N-({5-[(4-{(2-nitroanilino}piperidin-1-yl)sulfonyl]thien-2-yl}methyl)benzamide | 6.68 | 91.4 | a | 546 | 544 |
| 198 | N-[(5-{[4-(4-chloroanilino)piperidin-1-yl]sulfonyl}thien-2-yl)methyl]-3-nitrobenzamide | 6.12 | 94.7 | a | 535 | 533 |
| 199 | 3-nitro-N-{[5-({4-[4-(trifluoromethyl)anilino]-piperidin-1-yl}sulfonyl)thien-2-yl]methyl}-benzamide | 7.09 | 91.3 | a | 569 | 567 |
| 200 | 3-nitro-N-({5-[(4-{4-[(trifluoromethyl)sulfonyl]-anilino}piperidin-1-yl)sulfonyl]thien-2-yl}methyl)-benzamide | 6.92 | 92.4 | a | 633 | 631 |
| 201 | N-{[5-({4-[4-(aminocarbonyl)anilino]piperidin-1-yl}sulfonyl)thien-2-yl]methyl}-3-nitrobenzamide | 4.91 | 61.1 | a | 544 | 542 |
| 202 | N-[(5-{[4-(3-propylanilino)piperidin-1-yl]sulfonyl}thien-2-yl)methyl]-3-nitrobenzamide | 5.44 | 81.3 | a | 543 | 541 |
| 203 | N-[(5-{[4-(3-chloroanilino)piperidin-1-yl]sulfonyl]-thien-2-yl)methyl]-4-nitrobenzamide | 6.18 | 92.5 | a | 535 | 533 |
| 204 | 4-nitro-N-[(5-{[4-(3-methoxyanilino)piperidin-1-yl]sulfonyl}thien-2-yl)methyl]benzamide | 5.01 | 97 | a | 531 | 529 |
| 205 | 4-nitro-N-{[5-({4-[3-(trifluoromethyl)anilino]-piperidin-1-yl}sulfonyl)thien-2-yl]methyl}-benzamide | 6.98 | 97.1 | a | 569 | 567 |
| 206 | N-{[5-({4-[3-(dimethylamino)anilino]piperidin-1-yl}sulfonyl)thien-2-yl]methyl}-4-nitrobenzamide | 4.23 | 89.7 | a | 544 | 542 |
| 207 | 4-nitro-N-[(5-{[4-(3-propylanilino)piperidin-1-yl]sulfonyl}thien-2-yl)methyl]benzamide | 5.44 | 97.5 | a | 543 | 541 |
| 208 | 4-nitro-N-{[5-({4-[3-(methylsulfonyl)anilino]-piperidin-1-yl}sulfonyl)thien-2-yl]methyl}-benzamide | 5.36 | 92.1 | a | 579 | 577 |
| 209 | 4-nitro-N-{[5-({4-[3-(methylsulfanyl)anilino]-piperidin-1-yl}sulfonyl)thien-2-yl]methyl}-benzamide | 5.29 | 90.1 | a | 547 | 545 |
| 210 | N-{[5-({4-[3-(aminosulfonyl)anilino]piperidin-1-yl}sulfonyl)thien-2-yl]methyl}-4-nitrobenzamide | 4.96 | 90.8 | a | 580 | 578 |

| Example | Name | Rt HPLC | Purity | Gradient HPLC | Mass M + 1 | Mass M |
|---|---|---|---|---|---|---|
| 211 | methyl 3-{[1-({5-[({4-nitrobenzoyl}amino)methyl]-thien-2-yl}sulfonyl)piperidin-4-yl]amino}benzoate | 5.5 | 99 | a | 559 | 557 |
| 212 | 3-{[1-({5-[({4-nitrobenzoyl}amino)methyl]thien-2-yl}sulfonyl)piperidin-4-yl]amino}benzamide | 4.4 | 87 | a | 544 | 542 |
| 213 | 4-nitro-N-({5-[(4-{3-nitroanilino}piperidin-1-yl)sulfonyl]thien-2-yl}methyl)benzamide | 6.13 | 86.3 | a | 546 | 544 |
| 214 | 4-nitro-N-[(5-{[4-(2-methoxyanilino)piperidin-1-yl]sulfonyl}thien-2-yl)methyl]benzamide | 4.4 | 97.8 | a | 531 | 529 |
| 215 | 4-nitro-N-{5-({4-[2-(trifluoromethyl)anilino]-piperidin-1-yl}sulfonyl)thien-2-yl]methyl}-benzamide | 6.76 | 97.7 | a | 569 | 567 |
| 216 | 4-nitro-N-({5-[(4-{2-nitroanilino}piperidin-1-yl)sulfonyl]thien-2-yl}methyl)benzamide | 6.66 | 99.5 | a | 546 | 544 |
| 217 | N-[(5-{[4-(4-chloroanilino)piperidin-1-yl]sulfonyl}thien-2-yl)methyl]-4-nitrobenzamide | 6.11 | 99 | a | 535 | 533 |
| 218 | 4-nitro-N-{[5-({4-[4-(trifluoromethyl)anilino]-piperidin-1-yl}sulfonyl)thien-2-yl]methyl}-benzamide | 6.62 | 94.7 | a | 569 | 567 |
| 219 | 4-nitro-N-({5-[(4-{4-[(trifluoromethyl)sulfonyl]-anilino}piperidin-1-yl)sulfonyl]thien-2-yl}methyl)-benzamide | 6.48 | 96.8 | a | 633 | 631 |
| 220 | N-{[5-({4-[4-(aminocarbonyl)anilino]piperidin-1-yl}sulfonyl)thien-2-yl]methyl}-4-nitrobenzamide | 4.92 | 96.7 | a | 543 | 541 |
| 221 | N-{[5-({4-[4-(1,3-dithiolan-2-yl)anilino]piperidin-1-yl}sulfonyl)thien-2-yl]methyl}-4-nitrobenzamide | 5.41 | 92.4 | a | 605 | 603 |
| 222 | N-({5-[(4-{3-[amino(imino)methyl]anilino}-piperidin-1-yl)sulfonyl]thien-2-yl}methyl)-3-nitrobenzamide | 4.24 | 90.4 | a | 543 | 541 |
| 223 | N-({5-[(4-{3-[(2-hydroxyethyl)sulfonyl]anilino}-piperidin-1-yl)sulfonyl]thien-2-yl}methyl)-3-nitrobenzamide | 5.22 | 94.7 | a | 610 | 608 |
| 224 | N-({5-[(4-anilinopiperidin-1-yl)sulfonyl]thien-2-yl}methyl)-3-nitrobenzamide | 4.35 | 87.9 | a | 501 | 499 |
| 225 | N-({5-[(4-{3-[(2-hydroxyethyl)sulfonyl]anilino}-piperidin-1-yl)sulfonyl]thien-2-yl}methyl)-4-nitro-benzamide | 4.91 | 94 | a | 610 | 608 |
| 226 | N-({5-[(4-anilinopiperidin-1-yl)sulfonyl]thien-2-yl}methyl)-4-nitrobenzamide | 4.34 | 94.4 | a | 501 | 499 |
| 227 | N-({5-[(4-{3-[amino(imino)methyl]anilino}-piperidin-1-yl)sulfonyl]thien-2-yl}methyl)-4-nitrobenzamide | 4.23 | 90.8 | a | 543 | 541 |
| 228 | 3-nitro-N-({5-[(4-{3-[(trifluoromethyl)sulfanyl]-anilino}piperidin-1-yl)sulfonyl]thien-2-yl}methyl)-benzamide | 7.23 | 88 | a | 601 | 599 |
| 229 | 4-nitro-N-({5-[(4-{3-[(trifluoromethyl)sulfanyl]-anilino}piperidin-1-yl)sulfonyl]thien-2-yl}methyl)-benzamide | 7.28 | 90.4 | a | 601 | 599 |
| 230 | 3-nitro-N-[(5-{[4-({3-nitropyridin-2-yl}amino)-piperidin-1-yl]sulfonyl}thien-2-yl)methyl]-benzamide | 6.35 | 95.8 | a | 547 | 545 |
| 231 | N-{[5-({4-[(2,2-dioxido-1,3-dihydro-2-benzothien-5-yl)amino]piperidin-1-yl}sulfonyl)thien-2-yl]methyl}-3-nitrobenzamide | 5.18 | 94.5 | a | 591 | 589 |
| 232 | N-[(5-{[4-(2,3-dihydro-1H-inden-5-ylamino)-piperidin-1-yl]sulfonyl}thien-2-yl)methyl]-3-nitrobenzamide | 4.88 | 92 | a | 541 | 539 |
| 233 | 3-nitro-N-[(5-{[4-(2-propylanilino)piperidin-1-yl]sulfonyl}thien-2-yl)methyl]benzamide | 6.14 | 90.2 | a | 543 | 541 |
| 234 | 3-nitro-N-[(5-{[4-(4-propylanilino)piperidin-1-yl]sulfonyl}thien-2-yl)methyl]benzamide | 5.23 | 93.2 | a | 543 | 541 |
| 235 | N-[(5-{[4-(3-tert-butylanilino)piperidin-1-yl]sulfonyl}thien-2-yl)methyl]-3-nitrobenzamide | 5.5 | 94.4 | a | 557 | 555 |
| 236 | 3-nitro-N-{[5-({4-[3-(1,3-oxazol-5-yl)anilino]-piperidin-1-yl}sulfonyl)thien-2-yl]methyl}-benzamide | 5.44 | 91.1 | a | 568 | 566 |
| 237 | 3-nitro-N-[(5-{[4-(2-phenylethyl)piperidin-1-yl]sulfonyl}thien-2-yl)methyl]benzamide | 7.36 | 97.5 | a | 514 | 512 |
| 238 | N-({5-[(4-{[3-chloro-5-(trifluoromethyl)pyridin-2-yl]amino}piperidin-1-yl)sulfonyl]thien-2-yl}methyl)-3-nitrobenzamide | 7.27 | 90.3 | a | 604 | 602 |
| 239 | N-[(5-{[4-([1,1'-biphenyl]-3-ylamino)piperidin-1-yl]sulfonyl}thien-2-yl)methyl]-3-nitrobenzamide | 5.97 | 82.3 | a | 577 | 575 |
| 240 | N-[(5-{[4-(3-benzylanilino)piperidin-1-yl]sulfonyl}thien-2-yl)methyl]-3-nitrobenzamide | 5.86 | 69 | a | 591 | 589 |
| 241 | 3-nitro-N-{[5-({4-[3-(morpholin-4-ylsulfonyl)-anilino]piperidin-1-yl}sulfonyl)thien-2-yl]methyl}-benzamide | 5.92 | 96.4 | a | 650 | 648 |

-continued

| Example | Name | Rt HPLC | Purity | Gradient HPLC | Mass M + 1 | Mass M |
|---|---|---|---|---|---|---|
| 242 | 3-nitro-N-[(5-{[4-(3-propylphenoxy)piperidin-1-yl]sulfonyl}thien-2-yl)methyl]benzamide | 7.56 | 75 | a | 544 | 542 |
| 243 | 4-nitro-N-[(5-{[4-(pyrimidin-2-ylamino)piperidin-1-yl]sulfonyl}thien-2-yl)methyl]benzamide | 4.28 | 92 | a | 503 | 501 |
| 244 | N-{[5-({4-[(3-aminopyridin-2-yl)amino]piperidin-1-yl}sulfonyl)thien-2-yl]methyl}-4-nitrobenzamide | 4.06 | 90 | a | 517 | 515 |
| 245 | 4-nitro-N-[(5-{[4-({3-nitropyridin-2-yl}amino)-piperidin-1-yl]sulfonyl}thien-2-yl)methyl]-benzamide | 6.31 | 94.3 | a | 547 | 545 |
| 246 | N-[(5-{[4-(2,3-dihydro-1H-inden-5-ylamino)-piperidin-1-yl]sulfonyl}thien-2-yl)methyl]-4-nitrobenzamide | 4.92 | 89.9 | a | 541 | 539 |
| 247 | 4-nitro-N-[(5-{[4-(2-propylanilino)piperidin-1-yl]sulfonyl}thien-2-yl)methyl]benzamide | 6.17 | 93.9 | a | 543 | 541 |
| 248 | 4-nitro-N-[(5-{[4-(4-propylanilino)piperidin-1-yl]sulfonyl}thien-2-yl)methyl]benzamide | 5.27 | 93.8 | a | 543 | 541 |
| 249 | N-[(5-{[4-(3-tert-butylanilino)piperidin-1-yl]sulfonyl}thien-2-yl)methyl]-4-nitrobenzamide | 5.54 | 92.7 | a | 557 | 555 |
| 250 | 4-nitro-N-{[5-({4-[3-(1,3-oxazol-5-yl)anilino]-piperidin-1-yl}sulfonyl)thien-2-yl]methyl}-benzamide | 5.43 | 94.3 | a | 568 | 566 |
| 251 | 4-nitro-N-[(5-{[4-(2-phenylethyl)piperidin-1-yl]sulfonyl}thien-2-yl)methyl]benzamide | 7.32 | 97.9 | a | 514 | 512 |
| 252 | N-({5-[(4-{[3-chloro-5-(trifluoromethyl)pyridin-2-yl]amino}piperidin-1-yl)sulfonyl]thien-2-yl}methyl)-4-nitrobenzamide | 7.29 | 86.1 | a | 604 | 602 |
| 253 | N-[(5-{[4-([1,1'-biphenyl]-3-ylamino)piperidin-1-yl]sulfonyl}thien-2-yl)methyl]-4-nitrobenzamide | 6 | 85.2 | a | 577 | 575 |
| 254 | N-[(5-{[4-(3-benzylanilino)piperidin-1-yl]sulfonyl}-thien-2-yl)methyl]-4-nitrobenzamide | 5.9 | 90.4 | a | 591 | 589 |
| 255 | 4-nitro-N-{[5-({4-[3-(morpholin-4-ylsulfonyl)-anilino]piperidin-1-yl}sulfonyl)thien-2-yl]methyl}-benzamide | 5.95 | 95.5 | a | 650 | 648 |
| 256 | N-[(5-{[4-(2-aminoanilino)piperidin-1-yl]sulfonyl}-thien-2-yl)methyl]-3-nitrobenzamide | 4.37 | 75.6 | a | 516 | 514 |
| 257 | 3-nitro-N-[(5-{[4-(pyrimidin-2-ylamino)piperidin-1-yl]sulfonyl}thien-2-yl)methyl]benzamide | 4.24 | 89.1 | a | 503 | 501 |
| 258 | N-{[5-({4-[(3-aminopyridin-2-yl)amino]piperidin-1-yl}sulfonyl)thien-2-yl]methyl}-3-nitrobenzamide | 4.03 | 80 | a | 517 | 515 |
| 259 | N-({5-[(4-{2-nitro-4-[(trifluoromethyl)sulfonyl]-anilino}piperidin-1-yl)sulfonyl]thien-2-yl}methyl)-3-methoxybenzamide | 6.66 | 96.8 | a | 690 | 988 |
| 259 | ethyl 5-{[[(3-methoxybenzoyl)amino]methyl}-2-[(4-{3-[(trifluoromethyl)sulfonyl]anilino}piperidin-1-yl)sulfonyl]thiophene-3-carboxylate | 6.66 | 96.8 | a | 690 | 988 |
| 260 | 3-nitro-N-[(5-{[4-(3-phenylpropyl)piperazin-1-yl]sulfonyl}thien-2-yl)methyl]benzamide | 4.41 | 99.3 | a | 529 | 527 |
| 261 | 3-nitro-N-({5-[(4-{[4-(trifluoromethyl)pyrimidin-2-yl]amino}piperidin-1-yl)sulfonyl]thien-2-yl}methyl)benzamide | 5.78 | 99.3 | a | 571 | 569 |
| 262 | N-[(5-{[4-(3-cyclohexyl-4-hydroxyanilino)-piperidin-1-yl]sulfonyl}thien-2-yl)methyl]-3-nitrobenzamide | 4.78 | 81 | a | 599 | 597 |
| 263 | N-({5-[(4-{3-[(butylamino)sulfonyl]anilino}-piperidin-1-yl)sulfonyl]thien-2-yl}methyl)-3-nitrobenzamide | 5.8 | 99.4 | a | 636 | 634 |
| 264 | N[(5-{[4-(3-ethylanilino)piperidin-1-yl]sulfonyl}-thien-2-yl)methyl]-3-nitrobenzamide | 4.64 | 97.6 | a | 529 | 527 |
| 265 | 3-nitro-N-[(5-{[4-(5,6,7,8-tetrahydronaphthalen-1-ylamino)piperidin-1-yl]sulfonyl}thien-2-yl)methyl]-benzamide | 5.13 | 88.5 | a | 555 | 553 |
| 266 | 4-nitro-N-[(5-{[4-(3-propylphenoxy)piperidin-1-yl]sulfonyl}thien-2-yl)methyl]benzamide | 7.57 | 75.8 | a | 544 | 542 |
| 267 | N-[(5-{[4-(2,4-difluorobenzoyl)piperidin-1-yl]sulfonyl}thien-2-yl)methyl]-3-nitrobenzamide | 6.33 | 97.7 | a | 550 | 553 |

Protocol #4

Example 268

Preparation of N-[(5-{[4-(2,4-difluorobenzoyl)piperidin-1-yl]sulfonyl}-thien-2-yl)methyl]-3-methoxybenzamide 268

{[(3-Methoxybenzoyl)amino]methyl}thiophene-2-sulfonyl chloride 268a

The title sulfonylchloride was prepared according to the synthetic protocol#3 (example 177).

After flash chromatography using cyclohexane/EtOAc 1:1 as eluent, the main fractions were recrystallized from $CH_2Cl_2$/cyclohexane to afford pure 17.5 g of 268a.

$^1$H NMR (CDCl$_3$) δ 7.79 (t, J=4.0 Hz, 1H), 7.65 (t, J=7.9 Hz, 1H), 738 (m, 1H), 7.70-7.35 (t, J=8.1 Hz, 1H), 7.06 (m, 2H), 5.07 (d, J=3.8 Hz, 2H), 3.88 (s, 3H).

N-[(5-{[4-(2,4-difluorobenzoyl)piperidin-1-yl]sulfonyl}thien-2-yl)methyl]-3-methoxybenzamide, 268

268 was prepared using the general procedure protocol applied for the preparation of 2 and could be isolated as colorless solid in 98% yield (62 mg).). M/Z APCI: 535 (M+1), 533 (M−1). Anal. HPLC: rt.=6.22 min (method a).

Example 269

Preparation of 2-Hydroxy-N-({5-[(4-{3-[(trifluoromethyl)sulfonyl]-anilino}piperidin-1-yl)sulfonyl]thien-2-yl}methyl)benzamide 269

Diallyl-thiophen-2-ylmethylamine 269a

A solution of 2-aminomethyl-thiophene (51.4 g, 956 mmol) and i-Pr$_2$NEt (140 g, 1081 mmol) in CH$_2$Cl$_2$ (1 l) was placed in a 3-l flask equipped with a condenser and an efficient magnetic agitation. Allyl bromide (115.7 g, 454 mmol) was added, whereupon the moderately exothermic reaction spontaneously reached the reflux temperature after 2 h. The mixture was stirred overnight (16 h), washed (NaHCO$_3$ sat.; brine), dried (MgSO$_4$), and concentrated. The resulting oil was filtered over silica gel (EtOAc:hexane 1:4). The filtrate was concentrated and the filtration was repeated to afford 70.3 g (80%) of the title diallylamine as a brown-yellow oil, clean by NMR: $^1$H NMR (CDCl$_3$) δ 7.25 (br. d, J=5.9 Hz, 1H), 6.98 (br. dd, J=5.1, 2.8 Hz, 1H), 6.94-6.92 (m, 1H), 5.99-5.86 (m, 2H), 5.29-5.18 (m, 4H), 3.85 (s, 2H), 3.16 (dd, J=6.3, 0.9 Hz, 4H).

5-Diallylaminomethyl-thiophene-2-sulfonyl chloride 269b

A solution of the allyl-protected thiophene 269a (6.2 g, 32.1 mmol) in Et$_2$O was cooled to −70° C. by means of an acetone/dry ice bath. A solution of t-BuLi in pentane (21.38 mL, 1.5M, 32.1 mmol) was added over 2 min whereupon the internal temperature momentarily rose to −50° C. and the mixture turned orange. After 10 min., SO$_2$ was bubbled for 2 min, which led to the immediate formation of a thick precipitate. The reaction was allowed to reach 0° C., and a suspension of NCS (4.63 g, 32.1 mmol) in THF (20 mL) was added, whereupon the slurry turned purple. After 45 min at r.t., the mixture was filtered over SiO$_2$, eluting with EtOAc. Evaporation, dilution with EtOAc:hexane 1:5 and filtration over SiO$_2$ gave 5.0 g (53%) of the title sulfonyl chloride 269b as a pale brown oil which was used without further purification.

N,N-Diallyl-N-({5-[(4-{3-[(trifluoromethyl)sulfonyl]anilino}piperidin-1-yl)sulfonyl]-thien-2-yl}methyl)amine 269c A solution of 4-(3-trifluoromethanesulfonyl-phenylamino)-piperidine (731 mg, 237 mmol) and Et$_3$N (0.5 mL, 3.58 mmol) in CH$_2$Cl$_2$ (20 mL) was treated with the diallylamino sulfonyl chloride 269b 23° C. A thick precipitate appeared within 5 min, and the mixture was stirred overnight (even if complete within minutes). Dilution with CH$_2$Cl$_2$ (50 mL), washing (1120; brine), drying (MgSO$_4$), and evaporation afforded the crude product, which was filtered over silica gel (AcOEt:cyclohexane 1:1) to afford 1.15 g (86%) of the title bisallylamine, which was used in the next step without further purification.

2-Hydroxy-N-({5-[(4-{3-[(trifluoromethyl)sulfonyl]anilino}piperidin-1-yl)sulfonyl]-thien-2-yl}methyl)benzamide 269

A solution of the bisallylamine 269c (1.15 g, 2.04 mmol), N,N'-dimethylbarbituric acid (NDMBA, 637 mg, 4.08 mmol), and Pd(PPh$_3$)$_4$ (110 mg, 0.096 mmol) in CH$_2$Cl$_2$ (20 mL) was degassed by bubbling argon for 10 min. The reaction was stirred at 23° C. over the week-end (3 d), concentrated, diluted with DMF (12 mL), and treated with salicylic acid (290 mg, 2.10 mmol), 1-hydroxybenzotriazole (HOBt, 283 mg, 2.10 mmol), and N-ethyl-N'-(3-dimethylaminopropyl)-carbodiimide (EDC, 402 mg, 2.10 mmol) for 24 h at 23° C. Dilution with EtOAc, washing (H$_2$O, NaHCO$_3$ sat., brine), drying (MgSO$_4$), and evaporation afforded the crude 3-hydroxybenzamide. Purification by reverse-phase prep. HPLC (C8, H$_2$O:CH$_3$CN 60:40→0:100 over 40 min, r.t=23 min) and freeze-drying afforded 466 mg (38% from 269c) of the title 3-hydroxybenzamide as a white powder: NMR (DMSO-d6) δ 12.1 (s, 1H), 9.48 (t, J=5.9 Hz, 1H), 7.86 (dd, 7.9, 1.5 Hz, 1H), 7.50 (d, J=3.8 Hz, 1H), 7.45 (t, J=8.1 Hz, 1H), 7.41 (dd, J=8.9, 1.5 Hz, 1H), 7.21 (d, J=3.8 Hz, 1H), 7.18-7.10 (m, 3H), 6.93 (d, J=83 Hz, 1H), 6.91 (td, J=8.4, 1.1 Hz, 1H), 6.52 (d, J=7.7 Hz, 1H), 4.73 (d, J=5.8 Hz, 2H), 3.57-3.47 (br. d, 12.1, 2H), 3.52-3.35 (br. m., 1H), 2.62 (t, J=10.4 Hz, 2H), 2.07 (s, 1.2H, residual CH$_3$CN), 2.02-1.92 (br. d, J=10.4 Hz, 2H), 1.47 (qd, 11.2, 3.6 Hz, 2H). $^{13}$C NMR (DMSO-d6) δ167.52 (s, C=O), 158.36 (s), 148.98 (s), 147.85 (s), 132.83 (d), 132.74 (s), 131.47 (d), 130.00 (d), 128.98 (s), 127.09 (d), 125.52 (d), 124.83 (s), 118.92 (q, residual CH$_3$CN), 11834 (q, J=326 Hz, CF$_3$), 117.75 (d), 116.24 (d), 115.23 (d), 114.19 (q), 111.33 (d), 45.93 (d), 43.66 (t), 36.66 (t), 29.18 (t), 0.00 (s, residual CH$_3$CN). M/Z APCI: 604 (M+1), 602 (M−1). Anal. HPLC: R.t=6.60 min (method a). C$_{24}$H$_{24}$F$_3$N$_3$O$_6$S$_3$·0.3 CH$_3$CN 1.0 H$_2$O Calc.: C, 47.53%. H, 4.36%. N, 7.44%. Found: C, 47.41%, H, 4.09%, N, 7.49%.

In this protocol, salicylic acid could be replaced with other carboxylic acids, which include (but are not limited to): 4-chlorobenzoic acid, 4-nitrobenzoic acid, 3-nitrobenzoic acid, 3-methoxybenzoic acid, 5-nitro-1H-pyrazole-3-carboxylic acid, 2-hydroxynicotinic acid, 2-mercaptonicotinic acid, 3,4-dihydroxybenzoic acid, 2-picolinic acid.

The following compounds were prepared on a parallel fashion according to the examples described above The following table provides HPLC data and mass spectroscopy data of the mentioned examples

| Example | Name | Rt HPLC | Purity | Gradient HPLC | Mass M + 1 | Mass M |
|---|---|---|---|---|---|---|
| 270 | N-[(5-{[4-(1H-1,2,3-benzotriazol-1-yl)piperidin-1-yl]sulfonyl}thien-2-yl)methyl]-3-methoxybenzamide | 5.55 | 91.6 | a | 512 | 510 |
| 271 | N-[(5-{[4-(1H-1,2,3-benzotriazol-1-yl)piperidin-1-yl]sulfonyl}thien-2-yl)methyl]-2-hydroxybenzamide | 5.6 | 89.4 | a | 498 | 496 |
| 272 | N-{5-({4-[4-(1,3-dithiolan-2-yl)anilino]piperidin-1-yl}sulfonyl)thien-2-yl]methyl}-3-nitrobenzamide | 5.74 | 88.1 | a | 605 | 603 |
| 273 | 3-methoxy-N-[(5-{[4-(3-methoxyanilino)piperidin-1-yl]sulfonyl}thien-2-yl)methyl]benzamide | 4.58 | 88.6 | a | 516 | 514 |
| 274 | 3-methoxy-N-{[5-({4-[3-(trifluoromethyl)anilino]-piperidin-1-yl}sulfonyl)thien-2-yl]methyl}-benzamide | 6.5 | 97.5 | a | 554 | 552 |
| 275 | N-{[5-({4-[3-(dimethylamino)anilino]piperidin-1-yl}sulfonyl)thien-2-yl]methyl}-3-methoxy-benzamide | 4.4 | 83.1 | a | 530 | 528 |
| 276 | 3-methoxy-N-[(5-{[4-(3-propylanilino)piperidin-1-yl]sulfonyl}thien-2-yl)methyl]benzamide | 5.29 | 93.3 | a | 528 | 526 |
| 277 | 3-methoxy-N-{[5-({4-[3-(methylsulfonyl)-anilino]-piperidin-1-yl}sulfonyl)thien-2-yl]methyl}-benzamide | 5.59 | 95.7 | a | 564 | 562 |
| 278 | 3-methoxy-N-{[5-({4-[3-(methylsulfanyl)anilino]-piperidin-1-yl}sulfonyl)thien-2-yl]methyl}-benzamide | 5.5 | 97 | a | 532 | 530 |
| 279 | N-{[5-({4-[3-(aminosulfonyl)anilino]piperidin-1-yl}sulfonyl)thien-2-yl]methyl}-3-methoxy-benzamide | 5.2 | 93.8 | a | 565 | 563 |
| 280 | methyl 3-({1-[(5-{[(3-methoxybenzoyl)amino]-methyl}thien-2-yl)sulfonyl]piperidin-4-yl}amino)-benzoate | 5.76 | 96.8 | a | 544 | 542 |
| 281 | N-{[5-({4-[3-(aminocarbonyl)anilino]piperidin-1-yl}sulfonyl)thien-2-yl]methyl}-3-methoxy-benzamide | 4.08 | 95.4 | a | 529 | 527 |
| 282 | 3-methoxy-N-[(5-{[4-(2-methoxyanilino)piperidin-1-yl]sulfonyl}thien-2-yl)methyl]benzamide | 4.58 | 90.2 | a | 516 | 514 |
| 283 | N-({5-[(4-{3-nitroanilino}piperidin-1-yl)sulfonyl]thien-2-yl}methyl)-3-methoxybenzamide | 6.44 | 89.3 | a | 531 | 529 |
| 284 | 3-methoxy-N-{[5-({4-[2-(trifluoromethyl)anilino]-piperidin-1-yl}sulfonyl)thien-2-yl]methyl}-benzamide | 7.15 | 96.9 | a | 554 | 552 |
| 285 | N-({5-[(4-{2-nitroanilino}piperidin-1-yl)sulfonyl]-thien-2-yl}methyl)-3-methoxybenzamide | 6.59 | 95.2 | a | 531 | 529 |
| 286 | N-{[5-({4-[4-(aminocarbonyl)anilino]piperidin-1-yl}sulfonyl)thien-2-yl]methyl}-3-methoxy-benzamide | 4.57 | 95.2 | a | 529 | 0 |
| 287 | N-{[5-({4-[4-(1,3-dithiolan-2-yl)anilino]piperidin-1-yl}sulfonyl)thien-2-yl]methyl}-3-methoxy-benzamide | 5.64 | 96.6 | a | 599 | 597 |
| 288 | N-[(5-{[4-(3-chloroanilino)piperidin-1-yl]sulfonyl}-thien-2-yl)methyl]-3-methoxybenzamide | 6.57 | 97.7 | a | 520 | 518 |
| 289 | N-[(5-{[4-(4-chloroanilino)piperidin-1-yl]sulfonyl}-thien-2-yl)methyl]-3-methoxybenzamide | 6.86 | 100 | a | 520 | 518 |
| 290 | 3-methoxy-N-({5-[(4-{4-[(trifluoromethyl)-sulfonyl]anilino}piperidin-1-yl)sulfonyl]thien-2-yl}methyl)benzamide | 6.88 | 98 | a | 618 | 616 |
| 291 | N-({5-[(4-{3-[amino(imino)methyl]anilino}-piperidin-1-yl)sulfonyl]thien-2-yl}methyl)-3-methoxybenzamide | 4.18 | 91.3 | a | 528 | 526 |
| 292 | N-({5-[(4-{3-[(2-hydroxyethyl)sulfonyl]anilino}-piperidin-1-yl)sulfonyl]thien-2-yl}methyl)-3-methoxybenzamide | 5.11 | 92.2 | a | 594 | 592 |
| 293 | 3-methoxy-N-({5-[(4-{3-[(trifluoromethyl)sulfonyl]-anilino}piperidin-1-yl)sulfonyl]thien-2-yl}methyl)-benzamide | 6.55 | 88.1 | a | 618 | 616 |
| 294 | N-({5-[(4-anilinopiperidin-1-yl)sulfonyl]thien-2-yl}methyl)-3-methoxybenzamide | 4.52 | 88.5 | a | 486 | 484 |
| 295 | 3-methoxy-N-({5-[(4-{3-[(trifluoromethyl)sulfanyl]-anilino}piperidin-1-yl)sulfonyl]thien-2-yl}methyl)-benzamide | 6.54 | 92.9 | a | 586 | 584 |
| 296 | N-[(5-{[4-(4-hydroxyanilino)piperidin-1-yl]sulfonyl}thien-2-yl)methyl]-3-methoxybenzamide | 3.98 | 88 | a | 502 | 500 |
| 297 | 3-nitro-N-({5-[(4-{3-[(trifluoromethyl)sulfanyl]-anilino}piperidin-1-yl)sulfonyl]thien-2-yl}methyl)-benzamide | 7.23 | 88 | a | 601 | 599 |
| 298 | 4-nitro-N-({5-[(4-{3-[(trifluoromethyl)sulfanyl]-anilino}piperidin-1-yl)sulfonyl]thien-2-yl}methyl)-benzamide | 7.28 | 90.4 | a | 601 | 599 |
| 299 | N-[(5-{[4-(2-hydroxyanilino)piperidin-1-yl]sulfonyl}thien-2-yl)methyl]-3-methoxybenzamide | 4.12 | 89.8 | a | 502 | 500 |

-continued

| Example | Name | Rt HPLC | Purity | Gradient HPLC | Mass M + 1 | Mass M |
|---|---|---|---|---|---|---|
| 300 | 3-methoxy-N-[(5-{[4-(pyrimidin-2-ylamino)-piperidin-1-yl]sulfonyl}thien-2-yl)methyl]-benzamide | 4.15 | 92.7 | a | 488 | 486 |
| 301 | N-{[5-({4-[(3-aminopyridin-2-yl)amino]piperidin-1-yl}sulfonyl)thien-2-yl]methyl}-3-methoxy-benzamide | 3.96 | 93.1 | a | 502 | 500 |
| 302 | N-[(5-({4-[(3-nitropyridin-2-yl}amino)piperidin-1-yl]sulfonyl}thien-2-yl)methyl]-3-methoxybenzamide | 6.22 | 100 | a | 532 | 530 |
| 303 | N-{[5-({4-[(2,2-dioxido-1,3-dihydro-2-benzothien-5-yl)amino]piperidin-1-yl}sulfonyl)thien-2-yl]methyl}-3-methoxybenzamide | 5.04 | 98.5 | a | 576 | 574 |
| 304 | N-[(5-{[4-(2,3-dihydro-1H-inden-5-ylamino)-piperidin-1-yl]sulfonyl}thien-2-yl)methyl]-3-methoxybenzamide | 4.81 | 97.1 | a | 526 | 524 |
| 305 | 3-methoxy-N-[(5-{[4-(2-propylanilino)piperidin-1-yl]sulfonyl}thien-2-yl)methyl]benzamide | 5.99 | 99 | a | 528 | 526 |
| 306 | 3-methoxy-N-[(5-{[4-(4-propylanilino)piperidin-1-yl]sulfonyl}thien-2-yl)methyl]benzamide | 5.15 | 97.9 | a | 528 | 526 |
| 307 | N-[(5-{([4-(3-tert-butylanilino)piperidin-1-yl]sulfonyl}thien-2-yl)methyl]-3-methoxybenzamide | 5.41 | 98.9 | a | 542 | 540 |
| 308 | N-({5-[(4-{[3-chloro-5-(trifluoromethyl)pyridin-2-yl]amino}piperidin-1-yl)sulfonyl]thien-2-yl}methyl)-3-methoxybenzamide | 7.23 | 96.1 | a | 589 | 587 |
| 309 | 3-methoxy-N-{[5-({4-[3-(1,3-oxazol-5-yl)anilino]-piperidin-1-yl}sulfonyl)thien-2-yl]methyl}-benzamide | 5.25 | 94.9 | a | 553 | 551 |
| 310 | N-[(5-{[4-([1,1'-biphenyl]-3-ylamino)piperidin-1-yl]sulfonyl}thien-2-yl)methyl]-3-methoxybenzamide | 5.82 | 97.1 | a | 562 | 560 |
| 311 | 3-methoxy-N-[(5-{[4-(3-propylphenoxy)piperidin-1-yl]sulfonyl}thien-2-yl)methyl]benzamide | 7.55 | 78.7 | a | 529 | 527 |
| 312 | 3-methoxy-N-{[5-({4-[3-(morpholin-4-ylsulfonyl)-anilino]piperidin-1-yl}sulfonyl)thien-2-yl]methyl}-benzamide | 5.85 | 96.9 | a | 635 | 633 |
| 313 | 3-methoxy-N-[(5-{[4-(2-phenylethyl)piperidin-1-yl]sulfonyl}thien-2-yl)methyl]benzamide | 7.2 | 98.3 | a | 499 | 497 |
| 314 | N-[(5-{[4-(3-benzylanilino)piperidin-1-yl]sulfonyl}-thien-2-yl)methyl]-3-methoxybenzamide | 5.77 | 97.6 | a | 576 | 574 |
| 315 | 3-methoxy-N-[(5-{[4-(3-phenylpropyl)piperazin-1-yl]sulfonyl}thien-2-yl)methyl]benzamide | 4.33 | 99.7 | a | 514 | 512 |
| 316 | 3-methoxy-N-({5-[(4-{[4-(trifluoromethyl)-pyrimidin-2-yl]amino}piperidin-1-yl)sulfonyl]thien-2-yl}methyl)benzamide | 5.69 | 100 | a | 556 | 554 |
| 317 | N-[(5-{[4-(3-cyclohexyl-4-hydroxyanilino)-piperidin-1-yl]sulfonyl}thien-2-yl)methyl]-3-methoxybenzamide | 4.76 | 91.7 | a | 584 | 582 |
| 318 | N-({5-[(4-{3-[(butylamino)sulfonyl]anilino}-piperidin-1-yl)sulfonyl]thien-2-yl}methyl)-3-methoxybenzamide | 5.77 | 99.3 | a | 621 | 619 |
| 319 | N-[(5-{[4-(3-ethylanilino)piperidin-1-yl]sulfonyl}-thien-2-yl)methyl]-3-methoxybenzamide | 4.54 | 94.4 | a | 514 | 512 |
| 320 | 3-methoxy-N-[(5-{[4-(5,6,7,8-tetrahydronaphthalen-1-ylamino)piperidin-1-yl]sulfonyl}thien-2-yl)methyl]benzamide | 5.02 | 88.2 | a | 540 | 538 |
| 321 | N-[(5-{[4-(1H-1,2,3-benzotriazol-1-yl)piperidin-1-yl]sulfonyl}thien-2-yl)methyl]-5-nitro-1H-pyrazole-3-carboxamide | 5.12 | 96.2 | a | 517 | 515 |
| 322 | N-[(5-{[4-(1H-1,2,3-benzotriazol-1-yl)piperidin-1-yl]sulfonyl}thien-2-yl)methyl]-2-oxo-1,2-dihydropyridine-3-carboxamide | 4.15 | 93 | a | 499 | 497 |
| 323 | N-[(5-{[4-(1H-1,2,3-benzotriazol-1-yl)piperidin-1-yl]sulfonyl}thien-2-yl)methyl]-2-thioxo-1,2-dihydropyridine-3-carboxamide | 4.43 | 85.8 | a | 515 | 513 |
| 324 | N-[(5-{[4-(1H-1,2,3-benzotriazol-1-yl)piperidin-1-yl]sulfonyl}thien-2-yl)methyl]-3,4-dilydroxybenzamide | 4.62 | 89.1 | a | 514 | 512 |
| 325 | N-[(5-{[4-(1H-1,2,3-benzotriazol-1-yl)piperidin-1-yl]sulfonyl}thien-2-yl)methyl]pyridine-2-carboxamide | 5.22 | 98.9 | a | 483 | 481 |

Example 326

Preparation of N-[(5-{[4-(hexyloxy)piperidin-1-yl]sulfonyl}thien-2-yl)methyl]-3-methoxybenzamide 326

N,N-diallyl-N-[(5-{[4-(hexyloxy)piperidin-1-yl]sulfonyl}thien-2-yl)methyl]amine 326a To a solution of 4-hydroxy-piperidine (190 mg, 1.88 mmol) and DIEA (0.87 mL, 5.13 mmol) in 10 mL $CH_2Cl_2$ was added a solution of 5-({[1-(4-Chloro-phenyl)-methanoyl]-amino}-methyl)-thiophene-2-sulfonyl chloride 1b (500 mg, 1.71 mmol) in hot DCE. The reaction mixture was stirred for 4 h. 100 mL EtOAc were added and excess of amines were removed by extraction with HCl (1N). The sulfonamide intermediate was used without any further purification, where 300 mg (0.84 mmol) were dissolved in dry DMF under Ar. NaH (60 mg, 50% in parafine oil, 1.01 mmol) were added as a solid. The colour of the reaction changed to orange. The reaction mixture was stirred for 15' until no gas evolution was observed anymore. Iodohexane (356 mg, 1.68 mmol) dissolved in 1 mL DMF was added to the above solution and the reaction mixture was heated at 70° C. overnight. DMF was evaporated to dryness and the crude was taken up in $CH_2Cl_2$. The organic layer was washed twice with water, dried over $MgSO_4$ and evaporated to dryness. The crude was purified on silica gel using cyclohexane/EtOAc 3:1 as eluent to obtain 210 mg (59%) of pure 326a as a colorless oil.

N-[(5-{[4-(hexyloxy)piperidin-1-yl]sulfonyl}thien-2-yl)methyl]-methoxybenzamide 326

A solution of 326a (134 mg, 0.3 mmol), 1,3 Dimethylbarbituric acid (94 mg, 0.6 mmol) and Tetrakis(triphenylphosphine)palladium (12 mg, 0.01 mmol) were stirred under Argon in 3 mL $CH_2Cl_2$. The reaction was followed by HPLC until all starting material disappeared. The crude was evaporated to dryness and taken up in dry THF. To this solution was added DIEA (230 ul, 1.5 mmol) and 3-anisoylchloride 0.3 mmol). The reaction was stirred for 3 h, EtOAc was added and the organic layer was extracted with NaHCO3 sat, HCl (0.1N) and brine. The dry solution was evaporated and purified by flash chromatography on silica gel using cyclohexane/EtOAc 7:3 as eluent. 326 was obtained as an oil (54 mg, 37%): $H^1$ NMR ($CDCl_3$) δ 7.43-7.25 (m, 4H), 7.15-7.05 (m, 2H), 6.60 (m, 1H), 4.83 (d, J=6.0 Hz, 2H), 3.86 (s, 3H), 3.35 (d, J=6.6, 2H), 335-3.23 (m, 3H), 2.95 (m, 2H), 1.94 (m, 2H), 1.86 (m, 2H), 1.70-1.50 (m, 5H), 1.30-1.20 (m, 8H), 0.87 (t, J=6.8, 3H), M/Z APCI: 495.2 (M+1).

Example 327

Preparation of N-({5-[(4-heptanoylpiperidin-1-yl)sulfonyl]thien-2-yl}methyl)-3-methoxybenzamide 327

Methyl 1-({5-[(diallylamino)methyl]thien-2-yl}sulfonyl)piperidine-4-carboxylate 327a 5-Diallylaminomethyl-thiophene-2-sulfonyl chloride 229b (270 mg, 1.88 mmol) and DIEA (0.88 mL, 5.13 mmol) were dissolved in 10 mL chloroform. This solution was added methylisonipecotate (269 mg, 1.88 mmol) in 1 mL chloroform. The reaction was stirred for 3 h, diluted with $CH_2Cl_2$ and extracted with HCl (0.1N), $NaHCO_3$ sat. and brine. The organic layer was dried over $MgSO_4$ and evaporated to dryness. The crude was purified by flash chromatography on silica gel using cyclohexane/EtOAc 1:1 as eluent to obtain 440 mg (65%) of 327a as colorless oil: H' NMR ($CDCl_3$) δ 7.30 (d, J=3.6 Hz, 1H), 6.83 (d, J=3.6 1H), 5.78 (m, 2H), 5.18 (m, 4H), 3.70 (s, 2H), 3.52 (m, 6H), 3.07 (m, 4H), 2.50 (m, 2H), 2.25 (m, 1H), 1.93 (m, 2H), 1.84 (m, 2H). M/Z APCI: 399.2 (M+1)

1-({5-[(diallylamino)methyl]thien-2-yl}sulfonyl)-N-methoxy-N-methylpiperidine-4-carboxamide 327b 327a (390 mg, 1 mmol) and N,O-dimethylhydroxylamine (148 mg, 1.52 mmol) were stirred at −20° C. in anhydrous THF, while Isopropylmagnesium chloride in THF (2M, 1.65 mL, 3.23 mmol) were slowly added. The reaction mixture was allowed to warm to r.t. during 30', followed by an additional stirring at r.t. for 30'. The reaction is quenched with ammoniumchloride solution (20%). The aqueous layer is extracted with t-butylmethylether, and the combined organic layers are washed with brine, dried over $MgSO_4$ and evaporated to dryness. The crude is purified by flash chromatography on silica gel using cyclohexan/EtOAc 1:1 as eluent. 327b (380 mg, 90%) was obtained as a colourless solid: $H^1$ NMR (DMSO d6) δ7.53 (d, J=3.7 Hz, 1H), 7.16 (d, J=3.6 1H), 5.89 (m, 2H), 5.24 (m, 4H), 3.86 (s, 2H), 3.62 (m, 5H), 3.15 (m, 7H), 2.74 (m, 1H), 2.50 (m, 2H), 2.25 (m, 2H), 1.84 (m, 2H), 1.63 (m, 2H). M/Z APCI: 428.1 (M+1).

1-[1-({5-[(diallylamino)methyl]thien-2-yl}sulfonyl)piperidin-4-yl]heptan-1-one 327c 327b (376 mg, 0.88 mmol) was dissolved in anhydrous THF and cooled to −20° C. To this solution was added dropwise at −20° C. hexyllithium (2M in hexane) (2.46 mL, 6.2 mmol). The reaction was allowed to warm to rt. during 3 h and poured on 100 mL HCl/EtOH (5%). The aqueous phase was extracted with $CH_2Cl_2$ and the combined organic layers are washed with NaOH (2N) and brine, dried over $MgSO_4$ and evaporated to dryness. The crude material was purified by flash chromatography on silica gel using cyclohexane/EtOAc 4:1 as eluent to obtain 186 mg (47%) of (327c) as a brownish oil: $H^1$ NMR ($CDCl_3$) δ 7.40 (d, J=3.6 Hz, 1H), 725 (d, J=3.6 1H), 5.95 (m, 2H), 5.50 (m, 4H), 4.32 (s, 2H), 3.70-3.50 (m, 6H), 2.50 (m, 2H), 2.32 (m, 3H), 1.85 (m, 2H), 1.68 (m, 2H), 1.46 (m, 2H), 0.130-1.12 (m, 6H), 0.80 (t, J=6.6 Hz, 3H), M/Z APCI: 453.2 (M+1)

N-({5-[(4-heptanoylpiperidin-1-yl)sulfonyl]thien-2-yl}methyl)-3-methoxybenzamide 327

A solution of 327c (100 mg, 0.22 mmol), 1,3-Dimethylbarbituric acid (69 mg, 0.44 mmol) and Tetrakis(triphenylphosphine)palladium (12 mg, 0.01 mmol) were stirred in 3 mL $CH_2Cl_2$ overnight. The deprotection was followed by TLC. After complete cleavage of the protecting groups, the solvent was evaporated to dryness. The crude was taken up in THF, DIEA (76 ul, 0.33 mmol) was added, followed by the slow addition of 3-anisoylchloride (38 mg, 0.22 mmol) in THF. The reaction was stirred for 3 h, diluted with EtOAc and extracted with $NaHCO_3$ and brine. The organic layers were dried over Na2SO4 and evaporated to dryness. The crude mixture was purified by flash chromatography on silica gel using cyclohexane/EtOAc 1:1 as eluent to obtain 30 mg (50%) of 327 as a colorless oil: $H^1$ NMR ($CDCl_3$) δ 7.40-7.10 (m, 3H), 6.95 (m, 2H), 6.45 (m, 1H), 4.70 (d, J=6.0 Hz, 2H), 3.74 (s, 3H), 3.58 (m, 2H), 2.40 (m, 2H), 2.27 (t, J=7.5 Hz, 2H), 2.19 (m, 1H), 1.77 (m, 2H), 1.64 (m, 2H), 1.13 (m, 8H), 0.74 (t, J=6.8 Hz, 3H), M/Z APCI: 506.3 (M+1).

Example 328

Preparation of 4-chloro-N-[(5-{[4-(3-propylanilino)piperidin-1-yl]sulfonyl}-2-furyl)methyl]benzamide 328

4-Chloro-N-2-furylmethyl-benzamide 328a

A solution of 4-chlorobenzoyl chloride (3.2 g, 18.5 mol) in 50 ml dry $CH_2Cl_2$ was added over 30 min to a stirred solution of 2-furfurylamine (2 g, 20.6 mol) and $^iPr_2NEt$ (7 ml, 41 mol) in $CH_2Cl_2$ (200 ml) at 0° C. The reaction was allowed to warm to room temperature over 3 h. The mixture was diluted with 200 ml of $CH_2Cl_2$, washed twice with HCl aq. (1N) and dried over $MgSO_4$. Evaporation of the solvent afforded 4 g (83%) of the title benzamide as a white solid: $^1$H NMR: (DMSO-d$^6$) δ 9.05 (t, J=5.7 Hz, 1H), 7.89 (d, J=8.7 Hz, 2H), 7.57 (m, 1H), 7.53 (d, J=8.7 Hz, 2H), 6.40 (dd, J=3.7, 1.1 Hz, 1H), 6.28 (d, J=3.7 Hz, 1H), 4.46 (d, J=5.6 Hz, 2H). M/Z APCI: 236.6 (M+1), 234.8 (M−1).

5-({[1-(4-Chloro-phenyl)-methanoyl]-amino}-methyl)-furane-2-sulfonyl chloride 328b Chlorosulfonic acid (494 mg, 4.24 mmol) in $CH_2Cl_2$ (10 ml) was added dropwise to a solution of 9a (500 mg, 2.12 mmol) in $CH_2Cl_2$ (20 ml) at −80° C. The mixture was allowed to reach room temperature in 5 h. Excess of sulfonic acid was quenched with ice and $NaHCO_3$. 1.62 ml (40% aqueous soL, 2.54 mmol) of Tetrabutylammonium hydroxide were added, and the so formed salt was extracted with DCM. The organic layer was dried over MgSO4, filtered and evaporated to dryness. A red coloured oil (1.11 g) could isolated in 94% yield, which was used for the following step with any further purification.

The intermediate sulfonic acid tetrabutylammonium salt (1.1 g, 1.97 mmol) was dissolved in 20 ml DCM and flushed with Argon. Triphosgene (410 mg, 138 mmol) was added as a solid followed by the addition of a solution of 60 µl DMF in 2 ml DCM. The reaction was stirred under Ar. for 3 h at r.t. The solvent was evaporated using reduced pressure, and the crude oily residue was purified by flash chromatography using PE/EtOAc 2:1 as eluant. Main fractions afforded 450 mg (69%) of title sulfonylchloride 328b. $^1$H NMR (CDCl$_3$) δ 7.57 (d, J=8.7 Hz, 2H), 7.27 (d, J=8.7 Hz, 2H), 7.09 (d, J=3.4 Hz, 1H), 6.43 (t, b, 1H), 6.40 (d, J=3.4 Hz, 1H), 4.57 (d, J=6.0 Hz, 2H).

4-chloro-N-[(5-{[4-(3-propylanilino)piperidin-1-yl]sulfonyl}-2-furyl)methyl]benzamide 328

328 was synthesised according to the protocol for the synthesis of 2. Isolated yield: 21 mg (82%). Anal. HPLC: R.t=534 min (method a). M/Z APCI: 516.2 (M+1), 514.1 (M−1).

The following compounds were prepared on a parallel fashion according to the examples described above The following table provides HPLC data and mass spectroscopy data of the mentioned examples

| Example | Name | rt HPLC | Purity | Gradient HPLC | Mass M + 1 | Mass M |
|---|---|---|---|---|---|---|
| 329 | 4-chloro-N-[(5-{[4-(3-chloroanilino)piperidin-1-yl]sulfonyl}-2-furyl)methyl]benzamide | 6.41 | 97.8 | a | 508 | 506 |
| 330 | 4-chloro-N-[(5-{[4-(3-methoxyanilino)piperidin-1-yl]sulfonyl}-2-furyl)methyl]benzamide | 4.86 | 92 | a | 504 | 502 |
| 331 | 4-chloro-N-{[5-({4-[3-(trifluoromethyl)anilino]piperidin-1-yl}sulfonyl)-2-furyl]methyl}benzamide | 6.73 | 96.8 | a | 542 | 540 |
| 332 | 4-chloro-N-{[5-({4-[3-(dimethylamino)anilino]-piperidin-1-yl}sulfonyl)-2-furyl]methyl}benzamide | 4.29 | 93.6 | a | 517 | 515 |
| 333 | 4-chloro-N-{[5-({4-[3-(methylsulfonyl)anilino]-piperidin-1-yl}sulfonyl)-2-furyl]methyl}benzamide | 5.42 | 98 | a | 552 | 550 |
| 334 | 4-chloro-N-{[5-({4-[3-(methylsulfanyl)anilino]-piperidin-1-yl}sulfonyl)-2-furyl]methyl}benzamide | 5.46 | 96 | a | 520 | 518 |
| 335 | N-{[5-({4-[3-(aminosulfonyl)anilino]piperidin-1-yl}sulfonyl)-2-furyl]methyl}-4-chlorobenzamide | 5.08 | 94 | a | 553 | 551 |
| 336 | methyl 3-({1-[(5-{[(4-chlorobenzoyl)amino]-methyl}-2-furyl)sulfonyl]piperidin-4-yl}amino)-benzoate | 5.64 | 98 | a | 532 | 530 |
| 337 | 3-({1-[(5-{[(4-chlorobenzoyl)amino]methyl}-2-furyl)sulfonyl]piperidin-4-yl}amino]benzamide | 4.3 | 97.1 | a | 517 | 515 |
| 338 | 4-chloro-N-({5-[(4-{3-nitroanilino}piperidin-1-yl]sulfonyl]-2-furyl}methyl)benzamide | 6.22 | 87.4 | a | 519 | 517 |
| 339 | 4-chloro-N-[(5-{[4-(2-methoxyanilino)piperidin-1-yl]sulfonyl}-2-furyl)methyl]benzamide | 4.56 | 98.4 | a | 504 | 502 |
| 340 | 4-chloro-N-{[5-({4-[2-(trifluoromethyl)anilino]-piperidin-1-yl}sulfonyl)-2-furyl]methyl}benzamide | 6.86 | 97.6 | a | 542 | 540 |
| 341 | 4-chloro-N-({5-[(4-{2-nitroanilino}piperidin-1-yl]sulfonyl]-2-furyl}methyl)benzamide | 6.29 | 97.9 | a | 519 | 517 |
| 342 | 4-chloro-N-[(5-{[4-(4-chloroanilino)piperidin-1-yl]sulfonyl}-2-furyl)methyl]benzamide | 5.88 | 98.1 | | 508 | 506 |
| 343 | 4-chloro-N-{[5-({4-[4-(trifluoromethyl)anilino]-piperidin-1-yl}sulfonyl)-2-furyl]methyl}benzamide | 6.73 | 96.9 | | 542 | 540 |
| 344 | 4-chloro-N-({5-[(4-{4-[(trifluoromethyl)sulfonyl]-anilino}piperidin-1-yl)sulfonyl]-2-furyl}methyl)-benzamide | 6.57 | 99.1 | | 606 | 604 |
| 345 | N-{[5-({4-[4-(aminocarbonyl)anilino]piperidin-1-yl}sulfonyl)-2-furyl]methyl}-4-chlorobenzamide | 4.61 | 94.3 | | 517 | 515 |

| Example | Name | rt HPLC | Purity | Gradient HPLC | Mass M + 1 | Mass M |
|---|---|---|---|---|---|---|
| 346 | 4-chloro-N-{[5-({4-[4-(1,3-dithiolan-2-yl)anilino]-piperidin-1-yl}sulfonyl)-2-furyl]methyl}benzamide | 5.55 | 96.7 | | 578 | 576 |
| 347 | N-({5-[(4-{3-[amino(imino)methyl]anilino}-piperidin-1-yl)sulfonyl]-2-furyl}methyl)-4-chloro-benzamide | 4.07 | 94.5 | | 516 | 514 |
| 348 | 4-chloro-N-({5-[(4-{3-[(trifluoromethyl)sulfonyl]-anilino}piperidin-1-yl)sulfonyl]-2-furyl}methyl)-benzamide | 6.77 | 94.7 | a | 606 | 604 |
| 349 | N-({5-[(4-anilinopiperidin-1-yl)sulfonyl]-2-furyl}-methyl)-4-chlorobenzamide | 4.52 | 93.8 | | 474 | 472 |
| 350 | 4-nitro-N-({5-[(4-{3-[(trifluoromethyl)sulfanyl]-anilino}piperidin-1-yl)sulfonyl]2-furyl}methyl)-benzamide | 7.12 | 97 | a | 574 | 572 |

Example 351

Preparation of 4-chloro-N-({5-[(3-{3-[(trifluoromethyl)sulfonyl]-anilino}pyrrolidin-1-yl)sulfonyl]thien-2-yl}methyl)benzamide 351

4-chloro-N-[(5-{[(3R)-3-hydroxypyrrolidin-1-yl]sulfonyl}thien-2-yl)methyl]benzamide 351a To a suspension of R-3-pyrrolidinol hydrochloride (530 mg, 429 mmol) and DMA (0.75 ml, 14.3 mmol) in $CH_2Cl_2$/DMF 1:1 was added a solution of 5-({[1-(4-Chlorophenyl)-methanoyl]-amino}-methyl)-thiophene-2-sulfonyl chloride 1b (1.0 g, 2.86 mmol). At the end of addition the suspension disappeared. The reaction mixture was stirred overnight. 100 ml EtOAc were added and the excess of amine was extracted with HCl (1N), followed by washings with brine. The organic layers were dried over $MgSO_4$ and evaporated to dryness to provide 351a (1.14 g, 99.9%) as a colourless foam: $H^1$ NMR (DMSO d6) δ 9.34 (t, J=5.8 Hz, 1H), 7.89 (d, J=8.7 Hz, 2H), 7.49 (d, J=3.8 Hz, 1H), 7.55 (d, J=8.7 Hz, 2H), 7.13 (d, J=3.8 Hz, 1H), 4.95 (d, J=3.4 Hz, 1H), 4.65 (d, J=5.6 Hz, 2H), 4.16 (m, 1H), 3.40-3.20 (m, 5H), 3.00 (m, 1H), 3.35-3.23 (m, 3H), 1.80-1.60 (m, 2H), M/Z APCI: 401.2 (M+1), 398.9 (M−1).

4-chloro-N-({5-[(3-oxopyrrolidin-1-yl)sulfonyl]thien-2-yl}methyl)benzamide 351b

At −80° C. oxalylchloride (36 mg, 0.28 mmol) was dissolved in dry $CH_2Cl_2$, while DMSO (50 ul, 0.6 mmol) were added slowly. The solution was stirred under Ar. For 15'. 351a (100 mg, 0.25 mmol) was dissolved in 2 ml $CH_2Cl_2$, and this solution was added dropwise to the above reaction mixture at −80° C. The reaction was stirred for 15' at low temperature, before DIEA (0.21 ml, 1.25 mmol) was added. The reaction was stirred at −80° C. for 30' and allowed to warm to it during 2 h. A white solid was formed, the reaction was quenched with water and extracted with $CH_2Cl_2$ several times. The combined organic layers were dried over $MgSO_4$ and evaporated to dryness. The crude was purified by flash chromatography on silica gel using EtOAc/cyclohexane 2:1 as eluent. 351b (80 mg, 80%) was obtained as a colourless solid.: H' NMR ($CDCl_3$) δ 7.72 (d, J=8.7 Hz, 2H), 7.46 (d, J=3.8 Hz, 1H), 7.42 (d, J=8.7 Hz, 2H), 7.08 (d, J=3.8 Hz, 1H), 6.59 (t, J=5.8, 1H), 4.80 (d, J=6.0 Hz, 2H), 3.58 (t, J=7.5 Hz, 2H), 3.50 (s, 3H), 2.54 (t, J=7.5, 2H), 3.35-3.23 (m, 3H), 2.95 (m, 2H), 1.94 (m, 2H), 1.86 (m, 2H), 1.70-1.50 (m, 5H), 130-1.20 (m, 8H), 0.87 (t, J=6.8, 3H), M/Z APCI-399.0 (M+1), 397.2 (M−1)

4-chloro-N-({5-[(3-{3-[(trifluoromethyl)sulfonyl]anilino}pyrrolidin-1-yl)sulfonyl]thien-2-yl}methyl)benzamide 351

351b was prepared according to the protocol #1 example 110 and was isolated as colourless solid in 84% yield (15 mg). M/Z APCI: 609 (M+1), 607 (M−1).)

Example 352

Preparation of 4-chloro-N-({5-[(4-{3-[(trifluoromethyl)sulfonyl]anilino}-azepan-1-yl)sulfonyl]thien-2-yl}methyl)benzamide 352

352 was prepared according to the protocol #1 example 110 and was isolated as colourless solid in 47% yield (12 mg). M/Z APCI: 637 (M+1), 639 (M−1).).

Example 353

Preparation of a Pharmaceutical Formulation

The following formulation examples illustrate representative pharmaceutical compositions according to the present invention being not restricted thereto.
Formulation 1—Tablets A sulfonamide compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active sulfonamide compound per tablet) in a tablet press.
Formulation 2—Capsules A sulfonamide compound of formula I is admixed as a dry powder with a starch diluent in an approximate 1:1 weight ratio. The mixture is filled into 250 mg capsules (125 mg of active sulfonamide compound per capsule).
Formulation 3—Liquid A sulfonamide compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.
Formulation 4—Tablets A sulfonamide compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active sulfonamide compound) in a tablet press.

Formulation 5—Injection

A sulfonamide compound of formula I is dissolved in a buffered sterile saline injectable aqueous medium to a concentration of approximately 5 mg/mL.

Example 354

Biological Assays

Biological Results

The activities of the sulfonamide derivatives claimed in the formula I were assessed using the above described in vitro and in vivo biological assays.

JNK 2 and 3 in vitro assays: JNK3 and/or 2 assays are performed in 96 well MTT plates, by incubation of 0.5 µg of recombinant pre-activated GST-JNK or GST-JNK2 with 1 µg of recombinant, biotinylated GST-c-Jun and 2 µM $^{33}\gamma$-ATP (2 nCi/µl), in the to presence or absence of sulfonamide inhibitors if formula I and in a reaction volume of 50 µl containing 50 mM Tris-HCl, pH 8.0; 10 mM MgCl$_2$; 1 mM Dithiothreitol, and 100 µM NaVO$_4$. The incubation is performed for 120 min. at R.T and stopped upon addition of 200 µl of a solution containing 250 µg of Streptavidine-coated SPA beads (Amersham, Inc.)*, 5 mM EDTA, 0.1% Triton X-100 and 50 µM ATP, in phosphate saline buffer. After incubation for 60 minutes at RT, beads are sedimented by centrifugation at 1500×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By substituting GST-c Jun for biotinylated GST-$_1$ATF$_2$ or myelin basic protein, this assay can be used to measure inhibition of preactivated p38 and ERK MAP Kinases, respectively.

| Example | JNK3 | JNK2 | p38 | ERK2 |
| --- | --- | --- | --- | --- |
| 37 | 0.68 | 1.19 | >30 | >30 |
| 84 | 0.86 | 1.30 | >30 | >30 |
| 86 | 0.80 | 1.05 | >30 | >30 |
| 91 | 0.15 | 0.64 | >30 | >30 |
| 109 | 0.23 | 0.59 | >30 | >30 |
| 110 | 0.11 | 0.31 | >30 | >30 |
| 120 | 0.40 | 0.56 | >30 | >30 |
| 131 | 0.71 | 2.23 | >30 | >30 |
| 155 | 0.53 | 0.50 | >30 | >30 |
| 168 | 0.89 | 1.20 | >30 | >30 |
| 204 | 0.17 | 0.22 | >30 | >30 |
| 211 | 0.27 | 0.39 | >30 | >30 |
| 271 | 0.36 | 0.22 | >30 | >30 |
| 285 | 0.19 | 0.23 | >30 | >30 |

The values indicated in respect of JNK2 and 3, p38 and ERK2 refer to the IC$_{50}$ (µM), i.e. the amount necessary to achieve 50% inhibition of said target (e.g. JNK2). From the above table it could be derived that said test compounds according to formula I do have a significant effect both on JNK2 and 3, but virtually no effect onto p38 and ERK2, thus delivering a quite selective inhibitory effect.

Sympathetic Neuron Culture and Survival Assay

Sympathetic neurons from superior cervical ganglia (SCG) of new-born rats (p4) are dissociated in dispase, plated at a density of 10$^4$ cells/cm$^2$ in 48 well MTT plates coated with rat tail collagen, and cultured in Leibowitz medium containing 5% rat serum, 0.75 µg/mL NGF 7S (Boehringer Mannheim Corp., Indianapolis, Ind.) and arabinosine 10$^5$M. Cell death is induced at day 4 after plating by exposing the culture to medium containing 10 µg/mL of anti NGF anti-body (Boehringer Mannheim Corp., Indianapolis, Ind.) and no NGF or arabinosine, in the presence or absence of sulfonamide inhibitors. 24 hours after cell death induction, determination of cell viability is performed by incubation of the culture for 1 hour, at 37° C. in 0.5 mg/mL of 3-(4,5-dimethylthiazol-2-yl)2,5 diphenyl tetrazolium bromide (MTT). After incubation in MTT cells are resuspended in DMSO, transferred to a 96 MTT plate and cell viability is evaluated by measuring optical density at 590 nm.

The results of this assay with various test compounds demonstrate that compounds of Formula I are rescuing neurons from cells death (% neurons alive between 10 and 80)

Il-2 Release Assay:

Jurkat cells, a human T cell leukemia cell line (American Type Culture Collection # TIB 152) were cultured in RPMI 1640 medium (Gibco, BRL) supplemented with 10% of heat-activated FCS, Glutamine and Penstrep. The cell suspension in the medium is diluted to give 2.10$^6$ cells/mL. The cells were plated (2.10$^5$ cells/well) on a 96-well plate containing different concentration of test compound (final concentration of compounds, 10, 3, 1, 03, 0.1 µM). This mixture is incubated 30 minutes at 37° C. in a humidified CO$_2$ atmosphere. Cells were then treated with 10 ul PMA+Ionomycine (0.1 µM and 1 µM final concentration) in all wells except negative control. In wells without compounds, 10 µl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

IL-2 ELISA Assay:

IL-2 release into the medium by PMA+Iono-stimulated Jurkat cells, in presence or absence of test compounds is assayed by ELISA. Following the procedure described below Solutions Wash buffer. PBS-Tween 0.05%

Diluent: PBS-Tween 0.05%

Substrate solution: Citric acid 0.1M/Na$_2$HPO$_4$ 0.1M

Stop solution: H$_2$SO$_4$ 20%

Matched Antibody Pairs/Standard:

From R&D Systems

Monoclonal anti-human IL-2 antibody (MAB602) (capture)

Biotinylated anti-human IL-2 antibody (BAF202) (detection)

Recombinant human IL-2 (202-IL-010) (standard)

Plate Preparation

Transfer 100 µl capture antibody diluted in PBS at 5 µg/mL into a 96 well ELISA plate and incubate overnight at room temperature.

Aspirate each well and wash 3 times with Wash buffer. After the last wash, damp the plate.

1. Saturate with 200 µl PBS-10% FCS. Incubate 1 hour at room temperature.
2. Repeat the wash step 2.

Assay Procedure

1. Add 100 µl of sample or standard (2000, 1000, 500, 250, 125, 62.5, 3125 pg/mL) and incubate 2 hours at room temperature.
2. Wash 3 times.
3. Add 100 µl of biotinylated anti-human IL-2 at 12.5 ng/mL. Incubate 2 hours at room temperature.
4. Wash 3 times.
5. Add 100 µl streptavidin-HRP (Zymed #43-4323) at 1:10'000. Incubate 30 minutes at room temperature.

6. Wash 3 times
7. Add 100 μl substrate solution (citric acid/$Na_2HPO_4$ (1:1)+ $H_2O_2$ 1:2000+OPD). Incubate 20-30 minutes at room temperature.
8. Add 50 μl of stop solution to each well.
9. Determine optical density using a microliter plate reader set to 450 nm with correction at 570 nm.

The result of this assay with various test compounds is summarized below:

| Example | % Inhibition of IL2 Production @3 uM |
|---|---|
| 37 | >30 |
| 84 | >30 |
| 86 | >30 |
| 91 | >30 |
| 109 | >30 |
| 110 | >30 |
| 120 | >30 |
| 131 | >30 |
| 155 | >30 |
| 168 | >30 |
| 204 | >30 |
| 211 | >30 |
| 271 | >30 |
| 285 | >30 |

C-Jun Reporter Assay
Cell Culture

Hlr c-Jun HeLa cells are cultured in DMEM High Glc supplemented with 10% FCS (Sigma), 2 mM Glutamine (Gibco), P/S, Hygromycin b 100 μg/mL and G418 250 μg/mL
Cell Culture Preparation
Cell Banks The cells are stored frozen in cryotubes under liquid nitrogen, as 1.8 mL volumes of cell suspension in culture medium containing 10% dimethyl sulfoxide.

Cells are kept in culture for no more than 20 passages.
Cell Culture Thawing

When necessary, frozen vials of cells are thawed rapidly at 37° C. in a water bath by gently swirling up to semi-complete thawing. Then the cell suspension are added to 10 mL of culture medium.

The cell suspension is then centrifuged for 5 minutes at 1200 rpm, the supernatant is removed and the cell pellet reconstituted in the medium and add to a 175 $cm^2$ flask containing 25 mL medium. The flasks are incubated at 37° C. in an atmosphere of 5% $CO_2$.
Cell Passage The cells are serially subcultured (passaged) when 80% confluent monolayers have been obtained.

The medium of each flask is removed and the monolayer is washed with 10-15 mL of phosphate buffer solution (PBS).

Trypsin-EDTA solution is added to the cell monolayer, incubated at 37° C. and tapped gently at intervals to dislodge the cells. Complete detachment and disaggregation of the cell monolayer is confirmed by microscopy examination. The cells are then resuspended in 10 mL of complete medium and centrifuged for 5 minutes at 1200 rpm. The supernatant are discarded, the cells are resuspended in culture medium and diluted 1/5 in 175 $cm^2$ flasks.
Day 0 Morning
Prepare Cells for Transfections The cells from flasks of near-confluent cultures are detached and disaggregated by treatment with trypsin as described above.

The cells are resuspended in culture medium and counted.

The cell suspension are diluted with medium to give about $3.5 \times 10^6$ cells/mL and 1 mL of cell suspension are put onto 2 10 cm culture dishes containing 9 mL of culture medium.

The plates are incubated at 37° C. in a humidified atmosphere of 5% $CO_2$ in air
Day 0 evening
Transfections
Control: 0.2 μg pTK *Renilla,* 5.8 μg pBluescript KS, 500 μl OPTIMEM (GIBCO), 18 μl Fugene 6
Induced: 0.1 μg pMEKK1, 0.2 μg pTK *Renilla,* 5.7 μg pBluescript KS, 500 μl OPTIMEM (GIBCO), 18 μl Fugene 6 30' RT The transfection mixture is added to the plated cells. The plates are incubated over night at 37° C. in a humidified atmosphere of 5% $CO_2$ in air
Day 1

A 96 wells plate containing 100 μl of culture medium per well is prepared

Negative control (vehicle): 2 μl of DMSO is added to the 100 μl (in triplicate).

Compound: 2 μl of Hit compound stock dilution are added to the 100 μl (in triplicate).

The transfected cells are trypsinised and ressuspend in 12 mL of culture medium.

100 μl of the dilution are added to each of the 96 wells plate.

The plate is incubated over night at 37° C. in a humidified atmosphere of 5% $CO_2$ in air
Hit Compound Dilutions Hit compound stock concentrations are the following: 3, 1 and 0.1 mM in 100% DMSO.
Day 2
Test Procedure
Dual-Luciferase™ Reporter Assay System (Promega)

The medium is removed from the plate and the cells washed two times with 100 μl PBS Completely remove the rinse solution before applying PLB reagent. Dispense into each culture well 5 μl of 1×PLB. Place the culture plates on a rocking platform or orbital shaker with gentle rocking/shaking to ensure complete and even coverage of the cell monolayer with 1×PLB. Rock the culture plates at room temperature for 15 minutes. Transfer 20 μl of the lysate into a white opaque 96 wells plate. Read in a luminometer.

Inject 50 μl of Luciferase Assay Reagent II wait 5", read 10"

Inject 50 μl of Stop & Glo® Reagent wait 5", read 10"
Check RLU Luciferase/RLU *Renilla* *1000

The result of this assay with various test compounds is summarized below:

| Example | % inhibition @ 10 uM |
|---|---|
| 37 | >30 |
| 84 | >30 |
| 86 | >30 |
| 91 | >30 |
| 109 | >30 |
| 110 | >30 |
| 120 | >30 |
| 131 | >30 |
| 155 | >30 |
| 168 | >30 |
| 204 | >30 |
| 211 | >30 |
| 271 | >30 |
| 285 | >30 |

LPS Induced Endotoxin Shock in Mice

The ability of the JNK inhibitors described in formula I to significantly reduce the level of inflammatory cytokines induced by LPS challenge was assessed using the following protocol:

LPS (*S. abortus*-Galanos Lab.-) was injected (200 µg/kg, i.v.) to Male C57BL/6 to induce endotoxin shock and compounds (0.1, 1, 10 mg/kg) or NaCl (200 uM) were injected intravenously (10 mL/kg) 15 min before the LPS challenge. Heparinized blood was obtained from the orbital sinus at different time points after the LPS challenge, and the blood was centrifuged at 9'000 rpm for 10 min at 4° C. to collect supernatant for the measurement of cytokines production by mouse ELISA kit such as IFNγ (Duoset R&D Ref. DY485). The test compounds displayed considerable capability to reduce inflammatory related cytokines.

Global Ischemia in Gerbils

The ability of the JNK inhibitors described in formula I to protect cell death during a stroke event was assessed using the following protocol:

1—Method

Surgery

Anesthesia: halothane or isoflurane (0.5-4%).

Sheaving of the gorge and incision of the skin.

The common carotid arteries (left and right) are freed from tissue.

Occlusion of the arteries using Bulldog microclamps during 5 min.

Disinfection of the surgery plan (Betadine®) and suture of the skin (Autoclip® ou Michel's hooks).

Stabulation of the animals under heating lamp until awake.

Stabulation of the animals in the animalry in individual cages.

Sacrifice of the Animals 7 days after ischemia (Decapitation or overdose of pentobarbital).

Sampling of the brain.

Histological Parameters

Freezing of the brain in isopentane (−20° C.)

Slicing of the hippocampus using a cryo-microtome (20 µm).

Staining with cresyl violet and/or TUNEL method

Evaluation of the lesions (in CA1/CA2 subfields of the hippocampus)

Gerhard & Boast score modified or

Cell counting in the CA1/CA2

Biochemical Parameters

Microdissection of the cerebral structures

Parameters determined: DNA fragmentation, lactate, calcium penetration.

Analytical methods: ELISA, colorimetry, enzymology, radiometry.

2—Treatment

Administration of the test article or the vehicle: 15 min after reperfusion (5-10 min after the recovery of the anesthesia).

Standard protocol 50 animals: 5 groups of 10 (group A: control, groups B-D: test article at 3 doses and group E: reference compound (ketamine 3×120 mg/kg, ip or Orotic acid 3×300 mg/kg, ip).

The test compounds displayed considerable capability to protect from neuronal apoptosis during induced global ischemia.

The invention claimed is:

1. A sulfonamide compound according to formula I $$Ar^1-\underset{X}{\overset{\phantom{|}}{C}}-\underset{R^1}{N}-(CH_2)_n-Ar^2-SO_2-Y \quad\quad I$$

with its geometrical isomers, in an optically active form as enantiomers, diastereomers, as well as in the form of racemates, as well as pharmaceutically acceptable salts thereof, wherein $Ar^1$ is selected from the group consisting of phenyl, thienyl, furanyl, pyridyl, and optionally substituted by substituted or unsubstituted $C_1$-$C_6$ alkyl, substituted or unsubstituted $C_1$-$C_6$ alkoxy, substituted or unsubstituted $C_2$-$C_6$ alkenyl, substituted or unsubstituted $C_2$-$C_6$ alkynyl, amino, acylamino, aminocarbonyl, $C_1$-$C_6$ alkoxycarbonyl, aryl, carboxyl, cyano, halo, hydroxy, nitro, sulfonyl, sulfoxy, acyloxy, $C_1$-$C_6$ thioalkoxy;

$Ar^2$ is selected from the group consisting of thienyl, furanyl, and pyridyl;

X is O or S;

$R^1$ is hydrogen or a $C_1$-$C_6$-alkyl group, or $R^1$ forms a substituted or unsubstituted 5-6-membered saturated or unsaturated ring with $Ar^1$;

n is an integer from 0 to 5;

Y is a piperidino group of the formula $$\underset{N}{\overset{(R^6)_{n'}}{\diagdown}}\!\!\!\!\!\!\!\overset{L^1}{\diagup}_{L^2}$$

wherein $L^1$ and $L^2$ are independently selected from the group consisting of H, substituted or unsubstituted $C_1$-$C_6$-alkyl, substituted or unsubstituted $C_2$-$C_6$-alkenyl, substituted or unsubstituted $C_2$-$C_6$-alkynyl, and substituted or unsubstituted cyclic $C_4$-$C_8$-alkyl optionally containing 1-3 heteroatoms and optionally fused with aryl or heteroaryl; or $L^1$ and $L^2$ are independently selected from the group consisting of substituted or unsubstituted aryl, substituted or unsubstituted heteroaryl, aryl-$C_1$-$C_6$-alkyl, heteroaryl-$C_1$-$C_6$-alkyl, —C(O)—OR$^3$, —C(O)—R$^3$, —C(O)—NR$^{3'}$R$^3$, —NR$^{3'}$R$^3$, —NR$^{3'}$C(O)R$^3$, —NR$^{3'}$C(O)NR$^{3'}$R$^3$, —(SO)R$^3$, —(SO$_2$)R$^3$, —NHSO$_2$R$^3$, and —SO$_2$NR$^{3'}$R$^3$, with $R^3$ and $R^{3'}$ being substituents independently selected from the group consisting of H, substituted or unsubstituted $C_1$-$C_6$-alkyl, substituted or unsubstituted $C_2$-$C_6$-alkenyl, substituted or unsubstituted aryl, substituted or unsubstituted heteroaryl, substituted or unsubstituted aryl-$C_1$-$C_6$-alkyl, and substituted or unsubstituted heteroaryl-$C_1$-$C_6$-alkyl;

said aryl or heteroaryl groups being optionally substituted $C_1$-$C_6$-alkyl, $C_1$-$C_6$-alkoxy, $C_2$-$C_6$-alkenyl, $C_2$-$C_6$-alkynyl, amino, acylamino, aminocarbonyl, $C_1$-$C_6$-alkoxycarbonyl, aryl, carboxyl, cyano, halogen, hydroxy, nitro, sulfonyl, sulfoxy or $C_1$-$C_6$-thioalkoxy; and $R^6$ is selected from the group consisting of hydrogen, substituted or unsubstituted $C_1$-$C_6$-alkyl, substituted or unsubstituted $C_1$-$C_6$-alkoxy, OH, halogen, nitro, cyano, sulfonyl, and oxo (=O); and n' is an integer from 0 to 4;

with the proviso that if $Ar^1$ is 4-chlorophenyl, then X is O, $R^1$ is H, $Ar^2$ is thienyl, and Y is not para-substituted by 2-hydroxyethyl;

wherein the term "substituted" means that the group that is substituted is substituted with from its 5 substituents, said substituents being a group selected from the group consisting of $C_1$-$C_6$ alkyl; $C_1$-$C_6$ alkyl aryl; $C_1$-$C_6$ alkyl heteroaryl; $C_2$-$C_6$ alkenyl; $C_2$-$C_6$ alkynyl; primary, secondary or tertiary amino groups; quaternary ammonium groups; acyl; acyloxy; acylamino; aminocarbonyl; alkoxycarbonyl; aryl; heteroaryl; carboxyl; cyano; halogen; hydroxyl; mercapto; nitro; sulfoxy; sulfonyl; alkoxy, thioalkoxy; and trihalomethyl.

2. A sulfonamide compound according to claim 1, wherein $Ar^1$ is selected from the group consisting of phenyl, thienyl, furyl, pyridyl, and optionally substituted by $C_1$-$C_6$-alkyl, $C_1$-$C_6$-alkoxy, $C_2$-$C_6$-alkenyl, $C_2$-$C_6$-alkynyl, amino, acylamino, aminocarbonyl, $C_1$-$C_6$-alkoxycarbonyl, aryl, carboxyl, cyano, halogen, hydroxy, nitro, sulfonyl and $C_1$-$C_6$-thioalkoxy.

3. A sulfonamide compound according to claim 2, wherein $Ar^1$ is an unsubstituted or substituted phenyl.

4. A sulfonamide compound according to claim 2, wherein $Ar^2$ is thienyl or furanyl group.

5. The sulfonamide compound according to claim 2 wherein the $C_1$-$C_6$ alkyl group is trihalomethyl.

6. A sulfonamide compound according to claim 1, wherein $Ar^1$ is selected from the group consisting of a 4-chlorophenyl, nitrophenyl, hydroxyphenyl, alkoxy phenyl, pyridyl, 3,4-dihydroxyphenyl, and X is O, $R^1$ is hydrogen, n is 1, $Ar^2$ is thienyl or furanyl.

7. A sulfonamide compound according to claim 6, wherein Y is

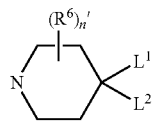

($R^6$) is selected from the group consisting of hydrogen, substituted or unsubstituted $C_1$-$C_6$ alkyl, substituted or unsubstituted $C_1$-$C_6$alkoxy, OH, halogen, nitro, cyano, sulfonyl, and oxo; n' is an integer of from 0 to 4; and wherein $L^1$ and $L^2$ are independently selected from each other from the group consisting of H, substituted or unsubstituted $C_1$-$C_6$-alkyl, substituted or unsubstituted $C_2$-$C_6$ alkenyl; or $L^1$ and $L^2$ are independently selected from the group consisting of substituted or unsubstituted aryl, substituted or unsubstituted heteroaryl, substituted or unsubstituted cyclic $C_4$-$C_8$ alkyl optionally containing 1-3 heteroatoms and optionally fused with aryl or heteroaryl, aryl-$C_1$-$C_4$ alkyl, heteroaryl-$C_2$-$C_4$ alkyl, —C(O)—OR$^3$, —C(O)—R$^3$, —C(O)—NR$^3$R$^3$, —NR$^3$R$^3$; —NR$^3$C(O)R$^3$, —NR$^3$C(O)R$^3$R$^3$, —(SO)R$^3$, —(SO$_2$)R$^3$, —NHSO$_2$R$^3$, and —SO$_2$NR$^3$R$^3$;

with R$^3$ and R$^3$' being substituents independently selected from the group consisting of H, substituted or unsubstituted $C_2$-$C_4$ alkyl, substituted or unsubstituted $C_2$-$C_6$ alkenyl, substituted or unsubstituted aryl, substituted or unsubstituted heteroaryl, substituted or unsubstituted aryl-$C_2$-$C_4$-alkyl, substituted or unsubstituted heteroaryl-$C_2$-$C_6$-alkyl;

said aryl or heteroaryl groups being optionally substituted with a member selected from the group consisting of $C_2$-$C_6$-alkyl, $C_2$-$C_6$-alkoxy, $C_2$-$C_6$-alkenyl, $C_2$-$C_6$-alkynyl, amino, acylamino, aminocarbonyl, $C_2$-$C_6$-alkoxycarbonyl, aryl, carboxyl, cyano, halogen, hydroxy, nitro, sulfonyl, sulfoxy and $C_2$-$C_6$-thioalkoxy.

8. A sulfonamide compound according to claim 7, wherein $R^6$ is H, $L^2$ is H, $L^1$ is a 5-membered cyclic group containing 3 heteroatoms or $L^1$ is —C(O)—R$^3$, or —NHR$^3$;

wherein Y is

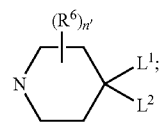

n' is an integer of from 0 to 4;

with R$^3$ being a substituent selected from the group comprising or consisting of $C_1$-$C_4$-alkyl, aryl, heteroaryl, aryl-$C_1$-$C_4$-alkyl and heteroaryl-$C_1$-$C_6$-alkyl;

said aryl or heteroaryl groups being optionally substituted by halogen, hydroxy, nitro, or sulfonyl.

9. The sulfonamide compound according to claim 1 wherein n is an integer of from 1 to 3.

10. The sulfonamide compound according to claim 9 wherein n is 1.

11. A sulfonamide compound according to claim 1, selected from the group consisting of:

4-chloro-N-{5-[4-(3-trifluoromethanesulfonyl-phenylamino)-piperidine-1-sulfonyl]-thiophen-2-ylmethyl}-benzamide;

4-chloro-N-[(5-{[4-(4-fluorobenzoyl)piperidin-1-yl]sulfonyl}thien-2-yl)methyl]benzamide;

4-chloro-N-({5-[(4-hydroxy-4-phenylpiperidin-1-yl)sulfonyl]thien-2-yl}methyl)benzamide;

N-({5-[(4-benzoylpiperidin-1-yl)sulfonyl]thien-2-yl}methyl)-4-chlorobenzamide;

4-chloro-N-[(5-{[4-(2-oxo-2,3-dihydro-1H-benzimidazol-1-yl)piperidin-1-yl]sulfonyl}thien-2-yl)methyl]benzamide;

N-({5-[(4-benzylpiperidin-1-yl)sulfonyl]thien-2-yl}methyl)-4-chlorobenzamide;

4-chloro-N-[(5-{[4-(2,4-difluorobenzoyl)piperidin-1-yl]sulfonyl}thien-2-yl)methyl]benzamide;

4-chloro-N-{[5-(piperidin-1-ylsulfonyl)thien-2-yl]methyl}benzamide;

4-chloro-N-{[5-({3-hydroxy-4-[3-(trifluoromethyl)phenyl]piperidin-1-yl}sulfonyl)thien-2-yl]methyl}benzamide;

N-({5-[(4-benzyl-4-hydroxypiperidin-1-yl)sulfonyl]thien-2-yl}methyl)-4-chlorobenzamide;

N-{[5-({4-[(2-tert-butyl-1H-indol-5-yl)amino]piperidin-1-yl}sulfonyl)thien-2-yl]methyl}-4-chlorobenzamide;

4-chloro-N-{[5-({4-[(phenylacetyl)amino]piperidin-1-yl}sulfonyl)thien-2-yl]methyl}benzamide;

N-[(5-{[4-(2H-1,2,3-benzotriazol-2-yl)piperidin-1-yl]sulfonyl}thien-2-yl)methyl]-4-chlorobenzamide;

4-chloro-N-[(5-{[4-(4-chlorobenzoyl)piperidin-1-yl]sulfonyl}thien-2-yl)methyl]benzamide;

N-{[5-({4-[benzyl(methyl)amino]piperidin-1-yl}sulfonyl)thien-2-yl]methyl}-4-chlorobenzamide;

4-chloro-N-{[5-({4-[3-(2,4-dichlorophenyl)-1H-pyrazol-5-yl]piperidin-1-yl}sulfonyl)thien-2-yl]methyl}benzamide;
4-chloro-N-[(5-{[4-(2,3,4,5,6-pentamethylbenzoyl)piperidin-1-yl]sulfonyl}thien-2-yl)methyl]benzamide;
4-chloro-N-{[5-({4-[5-(4-methoxyphenyl)-1H-pyrazol-3-yl]piperidin-1-yl}sulfonyl)thien-2-yl]methyl}benzamide;
N-({5-[(4-anilinopiperidin-1-yl)sulfonyl]thien-2-yl}methyl)-4-chlorobenzamide;
4-chloro-N-[(5-{[4-(2-phenylethyl)piperidin-1-yl]sulfonyl}thien-2-yl)methyl]benzamide;
N-[(5-{[4-(1H-1,2,3-benzotriazol-1-yl)piperidin-1-yl]sulfonyl}thien-2-yl)methyl]-4-chlorobenzamide;
2-{1-[(5-{[(4-chlorobenzoyl)amino]methyl}thien-2-yl)sulfonyl]piperidin-4-yl}-2H-1,2,3-benzotriazole-5-carboxylic acid;
methyl 1-{1-[(5-{[(4-chlorobenzoyl)amino]methyl}thien-2-yl)sulfonyl]piperidin-4-yl}-1H-1,2,3-benzotriazole-5-carboxylate;
methyl 1-{1-[(5-{[(4-chlorobenzoyl)amino]methyl}thien-2-yl)sulfonyl]piperidin-4-yl}-1H-1,2,3-benzotriazole-6-carboxylate;
methyl 2-{1-[(5-{[(4-chlorobenzoyl)amino]methyl}thien-2-yl)sulfonyl]piperidin-4-yl}-2H-1,2,3-benzotriazole-5-carboxylate;
4-chloro-N-[(5-{[4-(6-chloro-1H-1,2,3-benzotriazol-1-yl)piperidin-1-yl]sulfonyl}thien-2-yl)methyl]benzamide;
4-chloro-N-{[5-({4-[5-(trifluoromethyl)-1H-1,2,3-benzotriazol-1-yl]piperidin-1-yl}sulfonyl)thien-2-yl]methyl}benzamide;
N-[(5-{[4-(7-aza-1H-benzimidazol-1-yl)piperidin-1-yl]sulfonyl}thien-2-yl)methyl]-4-chlorobenzamide;
1-{1-[(5-{[(4-chlorobenzoyl)amino]methyl}thien-2-yl)sulfonyl]piperidin-4-yl}-1H-1,2,3-benzotriazole-5-carboxylic acid;
1-{1-[(5-{[(4-chlorobenzoyl)amino]methyl}thien-2-yl)sulfonyl]piperidin-4-yl}-1H-1,2,3-benzotriazole-6-carboxylic acid;
N-[(5-{[4-(2-amino-9H-purin-9-yl)piperidin-1-yl]sulfonyl}thien-2-yl)methyl]-4-chlorobenzamide;
4-chloro-N-[(5-{[4-(9H-purin-9-yl)piperidin-1-yl]sulfonyl}thien-2-yl)methyl]benzamide;
N-[(5-{[4-(6-amino-9H-purin-9-yl)piperidin-1-yl]sulfonyl}thien-2-yl)methyl]-4-chlorobenzamide;
4-chloro-N-({5-[(4-{6-nitro-1H-benzimidazol-1-yl}piperidin-1-yl)sulfonyl]thien-2-yl}methyl)benzamide;
4-chloro-N-({5-[(4-{5-nitro-1H-benzimidazol-1-yl}piperidin-1-yl)sulfonyl]thien-2-yl}methyl)benzamide;
4-chloro-N-[(5-{[4-(2H-1,2,3-triazol-2-yl)piperidin-1-yl]sulfonyl}thien-2-yl)methyl]benzamide;
N-[(5-{[4-(1H-benzimidazol-1-yl)piperidin-1-yl]sulfonyl}thien-2-yl)methyl]-4-chlorobenzamide;
4-chloro-N-{[5-({4-[3-propylanilino]piperidin-1-yl}sulfonyl)thien-2-yl]methyl}benzamide;
4-chloro-N-{[5-({4-[3-(dimethylamino)anilino]piperidin-1-yl}sulfonyl)thien-2-yl]methyl}benzamide;
methyl 3-({1-[(5-{[(4-chlorobenzoyl)amino]methyl}thien-2-yl)sulfonyl]piperidin-4-yl}amino)-benzoate;
4-chloro-N-{[5-({4-[3-(methylsulfanyl)anilino]piperidin-1-yl}sulfonyl)thien-2-yl]methyl}benzamide;
4-chloro-N-({5-[(4-{3-nitroanilino}piperidin-1-yl)sulfonyl]thien-2-yl}methyl)benzamide;
4-chloro-N-[(5-{[4-(2-methoxyanilino)piperidin-1-yl]sulfonyl}thien-2-yl)methyl]benzamide;
3-({1-[(5-{[(4-chlorobenzoyl)amino]methyl}thien-2-yl)sulfonyl]piperidin-4-yl}amino)benzamide;
4-chloro-N-({5-[(4-{2-nitro-4-[(trifluoromethyl)sulfonyl]anilino}piperidin-1-yl)sulfonyl]thien-2-yl}methyl)benzamide;
4-chloro-N-[(5-{[4-(4-chloroanilino)piperidin-1-yl]sulfonyl}thien-2-yl)methyl]benzamide;
4-chloro-N-({5-[(4-{4-[(trifluoromethyl)sulfonyl]anilino}piperidin-1-yl)sulfonyl]thien-2-yl}methyl)benzamide;
4-chloro-N-({5-[(4-{2-nitroanilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-4-chlorobenzamide;
N-[(5-{[4-(3-chloroanilino)piperidin-1-yl]sulfonyl}thien-2-yl)methyl]-3-nitrobenzamide;
4-chloro-N-[(5-{[4-(3-chloroanilino)piperidin-1-yl]sulfonyl}thien-2-yl)methyl]benzamide;
4-chloro-N-[(5-{[4-(3-methoxyanilino)piperidin-1-yl]sulfonyl}thien-2-yl)methyl]benzamide;
4-chloro-N-{[5-({4-[3-(methylsulfonyl)anilino]piperidin-1-yl}sulfonyl)thien-2-yl]methyl}benzamide;
N-[(5-{[4-(2-aminoanilino)piperidin-1-yl]sulfonyl}thien-2-yl)methyl]-4-chlorobenzamide;
4-chloro-N-[(5-{[4-(2-hydroxyanilino)piperidin-1-yl]sulfonyl}thien-2-yl)methyl]benzamide;
4-chloro-N-[(5-{[4-(4-hydroxyanilino)piperidin-1-yl]sulfonyl}thien-2-yl)methyl]benzamide;
4-chloro-N-[(5-{[4-(3-toluidino)piperidin-1-yl]sulfonyl}thien-2-yl)methyl]benzamide;
N-[(5-{[4-(3-tert-butylanilino)piperidin-1-yl]sulfonyl}thien-2-yl)methyl]-4-chlorobenzamide;
4-chloro-N-[(5-{[4-(2-propylanilino)piperidin-1-yl]sulfonyl}thien-2-yl)methyl]benzamide;
4-chloro-N-[(5-{[4-(4-propylanilino)piperidin-1-yl]sulfonyl}thien-2-yl)methyl]benzamide;
4-chloro-N-[(5-{[4-({3-nitropyridin-2-yl}amino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-4-chlorobenzamide;
4-chloro-N-[(5-{[4-(pyrimidin-2-ylamino)piperidin-1-yl]sulfonyl}thien-2-yl)methyl]benzamide;
4-chloro-N-({5-[(4-{[4-(trifluoromethyl)pyrimidin-2-yl]amino}piperidin-1-yl)sulfonyl]thien-2-yl}methyl)benzamide;
4-chloro-N-[(5-{[4-(3-ethylanilino)piperidin-1-yl]sulfonyl}thien-2-yl)methyl]benzamide;
4-chloro-N-[(5-{[4-(quinolin-5-ylamino)piperidin-1-yl]sulfonyl}thien-2-yl)methyl]benzamide;
4-chloro-N-[(5-{[4-(quinolin-8-ylamino)piperidin-1-yl]sulfonyl}thien-2-yl)methyl]benzamide;
4-nitro-N-({5-[(4-{3-[(trifluoromethyl)sulfonyl]anilino}piperidin-1-yl)sulfonyl]thien-2-yl}methyl)benzamide;
N-[(5-{[4-(1H-1,2,3-benzotriazol-1-yl)piperidin-1-yl]sulfonyl}thien-2-yl)methyl]-3-nitrobenzamide;
N-[(5-{[4-(2,4-difluorobenzoyl)piperidin-1-yl]sulfonyl}thien-2-yl)methyl]-4-nitrobenzamide;
N-[(5-{[4-(1H-1,2,3-benzotriazol-1-yl)piperidin-1-yl]sulfonyl}thien-2-yl)methyl]-4-nitrobenzamide;
3-nitro-N-[(5-{[4-(3-methoxyanilino)piperidin-1-yl]sulfonyl}thien-2-yl)methyl]benzamide;
N-{[5-({4-[3-(dimethylamino)anilino]piperidin-1-yl}sulfonyl)thien-2-yl]methyl}-3-nitrobenzamide;

3-nitro-N-{[5-({4-[3-(methylsulfonyl)anilino]piperidin-1-yl}sulfonyl)thien-2-yl]methyl}benzamide;
3-nitro-N-{[5-({4-[3-(methylsulfanyl)anilino]piperidin-1-yl}sulfonyl)thien-2-yl]methyl}benzamide;
methyl 3-{[1-({5-[({3-nitrobenzoyl}amino)methyl]-thien-2-yl}sulfonyl)-piperidin-4-yl]amino}benzoate;
N-{[5-({4-[3-(aminocarbonyl)anilino]piperidin-1-yl}sulfonyl)thien-2-yl]methyl}-3-nitrobenzamide;
3-nitro-N-({5-[(4-{3-nitroanilino}piperidin-1-yl)sulfonyl]thien-2-yl}methyl)benzamide;
3-nitro-N-[(5-{[4-(2-methoxyanilino)piperidin-1-yl]sulfonyl}thien-2-yl)methyl]benzamide;
3-nitro-N-({5-[(4-{2-nitroanilino}piperidin-1-yl)sulfonyl]thien-2-yl}methyl)benzamide;
N-[(5-{[4-(4-chloroanilino)piperidin-1-yl]sulfonyl}thien-2-yl)methyl]-3-nitrobenzamide;
3-nitro-N-({5-[(4-{4-[(trifluoromethyl)sulfonyl]anilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-3-nitrobenzamide;
N-[(5-{[4-(3-propylanilino)piperidin-1-yl]sulfonyl}thien-2-yl)methyl]-3-nitrobenzamide;
N-[(5-{[4-(3-chloroanilino)piperidin-1-yl]sulfonyl}thien-2-yl)methyl]-4-nitrobenzamide;
4-nitro-N-[(5-{[4-(3-methoxyanilino)piperidin-1-yl]sulfonyl}thien-2-yl)methyl]benzamide;
N-{[5-({4-[3-(dimethylamino)anilino]piperidin-1-yl}sulfonyl)thien-2-yl]methyl}-4-nitrobenzamide;
4-nitro-N-[(5-{[4-(3-propylanilino)piperidin-1-yl]sulfonyl}thien-2-yl)methyl]benzamide;
4-nitro-N-{[5-({4-[3-(methylsulfonyl)anilino]piperidin-1-yl}sulfonyl)thien-2-yl]methyl}benzamide;
4-nitro-N-{[5-({4-[3-(methylsulfanyl)anilino]piperidin-1-yl}sulfonyl)thien-2-yl]methyl}benzamide;
methyl 3-{[1-({5-[({4-nitrobenzoyl}amino)methyl]-thien-2-yl}sulfonyl)piperidin-4-yl]amino}benzoate;
3-{[1-({5-[({4-nitrobenzoyl}amino)methyl]thien-2-yl}sulfonyl)piperidin-4-yl]amino}benzamide;
4-nitro-N-({5-[(4-{3-nitroanilino}piperidin-1-yl)sulfonyl]thien-2-yl}methyl)benzamide;
4-nitro-N-[(5-{[4-(2-methoxyanilino)piperidin-1-yl]sulfonyl}thien-2-yl)methyl]benzamide;
4-nitro-N-({5-[(4-{2-nitroanilino}piperidin-1-yl)sulfonyl]thien-2-yl}methyl)benzamide;
N-[(5-{[4-(4-chloroanilino)piperidin-1-yl]sulfonyl}thien-2-yl)methyl]-4-nitrobenzamide;
4-nitro-N-({5-[(4-{4-[(trifluoromethyl)sulfonyl]anilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-4-nitrobenzamide;
N-({5-[(4-anilinopiperidin-1-yl)sulfonyl]thien-2-yl}methyl)-3-nitrobenzamide;
N-({5-[(4-anilinopiperidin-1-yl)sulfonyl]thien-2-yl}methyl)-4-nitrobenzamide;
3-nitro-N-[(5-{[4-({3-nitropyridin-2-yl}amino)piperidin-1-yl]sulfonyl}thien-2-yl)methyl]benzamide;
3-nitro-N-[(5-{[4-(2-propylanilino)piperidin-1-yl]sulfonyl}thien-2-yl)methyl]benzamide;
3-nitro-N-[(5-{[4-(4-propylanilino)piperidin-1-yl]sulfonyl}thien-2-yl)methyl]benzamide;
N-[(5-{[4-(3-tert-butylanilino)piperidin-1-yl]sulfonyl}thien-2-yl)methyl]-3-nitrobenzamide;
3-nitro-N-[(5-{[4-(2-phenylethyl)piperidin-1-yl]sulfonyl}thien-2-yl)methyl]benzamide;
4-nitro-N-[(5-{[4-(pyrimidin-2-ylamino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-4-nitrobenzamide;
4-nitro-N-[(5-{[4-({3-nitropyridin-2-yl}amino)piperidin-1-yl]sulfonyl}thien-2-yl)methyl]benzamide;
4-nitro-N-[(5-{[4-(2-propylanilino)piperidin-1-yl]sulfonyl}thien-2-yl)methyl]benzamide;
4-nitro-N-[(5-{[4-(4-propylanilino)piperidin-1-yl]sulfonyl}thien-2-yl)methyl]benzamide;
N-[(5-{[4-(3-tert-butylanilino)piperidin-1-yl]sulfonyl}thien-2-yl)methyl]-4-nitrobenzamide;
4-nitro-N-[(5-{[4-(2-phenylethyl)piperidin-1-yl]sulfonyl}thien-2-yl)methyl]benzamide;
N-[(5-{[4-(2-aminoanilino)piperidin-1-yl]sulfonyl}thien-2-yl)methyl]-3-nitrobenzamide;
3-nitro-N-[(5-{[4-(pyrimidin-2-ylamino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-3-nitrobenzamide;
N-({5-[(4-{2-nitro-4-[(trifluoromethyl)sulfonyl]anilino}piperidin-1-yl)sulfonyl]thien-2-yl}methyl)-3-methoxybenzamide;
N-[(5-{[4-(3-ethylanilino)piperidin-1-yl]sulfonyl}thien-2-yl)methyl]-3-nitrobenzamide;
N-[(5-{[4-(2,4-difluorobenzoyl)piperidin-1-yl]sulfonyl}thien-2-yl)methyl]-3-nitrobenzamide;
N-[(5-{[4-(2,4-difluorobenzoyl)piperidin-1-yl]sulfonyl}thien-2-yl)methyl]-3-methoxybenzamide;
2-Hydroxy-N-({5-[(4-{3-[(trifluoromethyl)sulfonyl]anilino}piperidin-1-yl)sulfonyl]thien-2-yl}methyl)benzamide;
N-[(5-{[4-(1H-1,2,3-benzotriazol-1-yl)piperidin-1-yl]sulfonyl}thien-2-yl)methyl]-3-methoxybenzamide;
N-[(5-{[4-(1H-1,2,3-benzotriazol-1-yl)piperidin-1-yl]sulfonyl}thien-2-yl)methyl]-2-hydroxybenzamide;
3-methoxy-N-[(5-{[4-(3-methoxyanilino)piperidin-1-yl]sulfonyl}thien-2-yl)methyl]benzamide;
N-{[5-({4-[3-(dimethylamino)anilino]piperidin-1-yl}sulfonyl)thien-2-yl]methyl}-3-methoxybenzamide;
3-methoxy-N-[(5-{[4-(3-propylanilino)piperidin-1-yl]sulfonyl}thien-2-yl)methyl]benzamide;
3-methoxy-N-{[5-({4-[3-(methylsulfonyl)anilino]piperidin-1-yl}sulfonyl)thien-2-yl]methyl}benzamide;
3-methoxy-N-{[5-({4-[3-(methylsulfanyl)anilino]piperidin-1-yl}sulfonyl)thien-2-yl]methyl}benzamide;
methyl 3-({1-[5-{[(3-methoxybenzoyl)amino]-methyl}thien-2-yl]sulfonyl]piperidin-4-yl}amino)-benzoate;
N-{[5-({4-[3-(aminocarbonyl)anilino]piperidin-1-yl}sulfonyl)thien-2-yl]methyl}-3-methoxybenzamide;
3-methoxy-N-[(5-{[4-(2-methoxyanilino)piperidin-1-yl]sulfonyl}thien-2-yl)methyl]benzamide;
N-({5-[(4-{3-nitroanilino}piperidin-1-yl)sulfonyl]thien-2-yl}methyl)-3-methoxybenzamide;
N-({5-[(4-{2-nitroanilino}piperidin-1-yl)sulfonyl]thien-2-yl}methyl)-3-methoxybenzamide;
N-{[5-({4-[4-(aminocarbonyl)anilino]piperidin-1-yl}sulfonyl)thien-2-yl]methyl}-3-methoxybenzamide;
N-[(5-{[4-(3-chloroanilino)piperidin-1-yl]sulfonyl}thien-2-yl)methyl]-3-methoxybenzamide;
N-[(5-{[4-(4-chloroanilino)piperidin-1-yl]sulfonyl}thien-2-yl)methyl]-3-methoxybenzamide;
3-methoxy-N-({5-[(4-{4-[(trifluoromethyl)sulfonyl]anilino}piperidin-1-yl)sulfonyl]thien-2-yl}methyl)benzamide;

3-methoxy-N-({5-[(4-{3-[(trifluoromethyl)sulfonyl]
anilino}piperidin-1-yl)sulfonyl]thien-2-yl}methyl)
benzamide;
N-({5-[(4-anilinopiperidin-1-yl)sulfonyl]thien-2-
yl}methyl)-3-methoxybenzamide;
N-[(5-{[4-(4-hydroxyanilino)piperidin-1-yl]
sulfonyl}thien-2-yl)methyl]-3-methoxybenzamide;
N-[(5-{[4-(2-hydroxyanilino)piperidin-1-yl]
sulfonyl}thien-2-yl)methyl]-3-methoxybenzamide;
3-methoxy-N-[(5-{[4-(pyrimidin-2-ylamino)piperidin-1-
yl]sulfonyl}thien-2-yl)methyl]benzamide;
N-{[5-({4-[(3-aminopyridin-2-yl)amino]piperidin-1-
yl}sulfonyl)thien-2-yl]methyl}-3-methoxybenzamide;
N-[(5-{[4-({3-nitropyridin-2-yl}amino)piperidin-1-yl]
sulfonyl}thien-2-yl)methyl]-3-methoxybenzamide;
3-methoxy-N-[(5-{[4-(2-propylanilino)piperidin-1-yl]
sulfonyl}thien-2-yl)methyl]benzamide;
3-methoxy-N-[(5-{[4-(4-propylanilino)piperidin-1-yl]
sulfonyl}thien-2-yl)methyl]benzamide;
N-[(5-{[4-(3-tert-butylanilino)piperidin-1-yl]
sulfonyl}thien-2-yl)methyl]-3-methoxybenzamide;
3-methoxy-N-[(5-{[4-(2-phenylethyl)piperidin-1-yl]
sulfonyl}thien-2-yl)methyl]benzamide;
N-[(5-{[4-(3-ethylanilino)piperidin-1-yl]sulfonyl}thien-
2-yl)methyl]-3-methoxybenzamide;
N-[(5-{[4-(1H-1,2,3-benzotriazol-1-yl)piperidin-1-yl]
sulfonyl}thien-2-yl)methyl]-2-oxo-1,2-dihydropyri-
dine-3-carboxamide;
N-[(5-{[4-(1H-1,2,3-benzotriazol-1-yl)piperidin-1-yl]
sulfonyl}thien-2-yl)methyl]-3,4-dihydroxybenzamide;
N-[(5-{[4-(1H-1,2,3-benzotriazol-1-yl)piperidin-1-yl]
sulfonyl}thien-2-yl)methyl]pyridine-2-carboxamide;
N-({5-[(4-heptanoylpiperidin-1-yl)sulfonyl]thien-2-
yl}methyl)-3-methoxybenzamide;
4-chloro-N-[(5-{[4-(3-propylanilino)piperidin-1-yl]sul-
fonyl}-2-furyl)methyl]benzamide;
4-chloro-N-[(5-{[4-(3-chloroanilino)piperidin-1-yl]sulfo-
nyl}-2-furyl)methyl]benzamide;
4-chloro-N-[(5-{[4-(3-methoxyanilino)piperidin-1-yl]
sulfonyl}-2-furyl)methyl]benzamide;
4-chloro-N-{[5-({4-[3-(trifluoromethyl)anilino]piperi-
din-1-yl}sulfonyl)-2-furyl]methyl}benzamide;
4-chloro-N-{[5-({4-[3-(dimethylamino)anilino]piperidin-
1-yl}sulfonyl)-2-furyl]methyl}benzamide;
4-chloro-N-{[5-({4-[3-(methylsulfonyl)anilino]piperidin-
1-yl}sulfonyl)-2-furyl]methyl}benzamide;
4-chloro-N-{[5-({4-[3-(methylsulfanyl)anilino]piperidin-
1-yl}sulfonyl)-2-furyl]methyl}benzamide;
methyl 3-({1-[(5-{[(4-chlorobenzoyl)amino]methyl}-2-
furyl)sulfonyl]piperidin-4-yl}amino)benzoate;
3-({1-[(5-{[(4-chlorobenzoyl)amino]methyl}-2-furyl)
sulfonyl]piperidin-4-yl}amino)benzamide;
4-chloro-N-({5-[(4-{3-nitroanilino}piperidin-1-yl)sulfo-
nyl]-2-furyl}methyl)benzamide;
4-chloro-N-[(5-{[4-(2-methoxyanilino)piperidin-1-yl]
sulfonyl}-2-furyl)methyl]benzamide;
4-chloro-N-({5-[(4-{2-nitroanilino}piperidin-1-yl)sulfo-
nyl]-2-furyl}methyl)benzamide;
4-chloro-N-[(5-{[4-(4-chloroanilino)piperidin-1-yl]sulfo-
nyl}-2-furyl)methyl]benzamide;
4-chloro-N-({5-[(4-{4-[(trifluoromethyl)sulfonyl]
anilino}piperidin-1-yl)sulfonyl]-2-furyl}methyl)ben-
zamide;
N-{[5-({4-[4-(aminocarbonyl)anilino]piperidin-1-
yl}sulfonyl)-2-furyl]methyl}-4-chlorobenzamide;
4-chloro-N-({5-[(4-{3-[(trifluoromethyl)sulfonyl]
anilino}piperidin-1-yl)sulfonyl]-2-furyl}methyl)ben-
zamide; and
N-({5-[(4-anilinopiperidin-1-yl)sulfonyl]-2-
furyl}methyl)-4-chlorobenzamide.

12. A sulfonamide compound according to claim 11, which is selected from the group consisting of:
4-chloro-N-[(5-{[4-(2,4-difluorobenzoyl)piperidin-1-yl]
sulfonyl}thien-2-yl)methyl]benzamide;
N-({5-[(4-anilinopiperidin-1-yl)sulfonyl]thien-2-
yl}methyl)-4-chlorobenzamide;
N-[(5-{[4-(1H-1,2,3-benzotriazol-1-yl)piperidin-1-yl]
sulfonyl}thien-2-yl)methyl]-4-chlorobenzamide;
N-[(5-{[4-(1H-benzimidazol-1-yl)piperidin-1-yl]
sulfonyl}thien-2-yl)methyl]-4-chlorobenzamide;
4-chloro-N-{[5-({4-[3-propylanilino]piperidin-1-
yl}sulfonyl)thien-2-yl]methyl}benzamide;
4-chloro-N-[(5-{[4-(4-chloroanilino)piperidin-1-yl]
sulfonyl}thien-2-yl)methyl]benzamide;
4-nitro-N-[(5-{[4-(3-methoxyanilino)piperidin-1-yl]
sulfonyl}thien-2-yl)methyl]benzamide;
methyl 3-{[1-({5-[({4-nitrobenzoyl}amino)methyl]thien-
2-yl}sulfonyl)piperidin-4-yl]amino}benzoate;
N-[(5-{[4-(1H-1,2,3-benzotriazol-1-yl)piperidin-1-yl]
sulfonyl}thien-2-yl)methyl]-2-hydroxybenzamide; and
N-({5-[(4-{2-nitroanilino}piperidin-1-yl)sulfonyl]thien-
2-yl}methyl)-3-methoxybenzamide.

13. A pharmaceutical composition containing at least one sulfonamide compound according to claim 1 and a pharmaceutically acceptable carrier, diluent or excipient.

14. A composition comprising a sulfonamide compound according to formula I

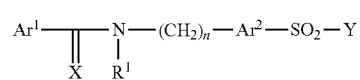

with its geometrical isomers, in an optically active form as enantiomers, diastereomers, as well as in the form of racemates, as well as pharmaceutically acceptable salts thereof, wherein X is O or S;

$Ar^1$ and $Ar^2$ are a substituted or unsubstituted aryl or heteroaryl group;

$R^1$ is hydrogen or a $C_1$-$C_6$-alkyl group, or $R^1$ forms a substituted or unsubstituted 5-6-membered saturated or unsaturated ring with $Ar^1$;

n is an integer from 0 to 5;

Y is a piperidino group of the formula

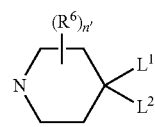

wherein $L^1$ and $L^2$ are independently selected from the group consisting of H, substituted or unsubstituted $C_1$-$C_6$-alkyl, substituted or unsubstituted $C_2$-$C_6$-alkenyl, substituted or unsubstituted $C_2$-$C_6$-alkynyl, and substituted or unsubstituted cyclic $C_4$-$C_8$-alkyl optionally containing 1-3 heteroatoms and optionally fused with aryl or heteroaryl; or $L^1$ and $L^2$ are independently selected from the group consisting of substituted or unsubstituted aryl, substituted or unsubstituted heteroaryl, aryl-$C_1$-$C_6$-alkyl, heteroaryl-$C_1$-$C_6$-alkyl, —C(O)—$OR^3$, —C(O)—$R^3$, —C(O)—$NR^{3'}R^3$, —$NR^{3'}R^3$, —$NR^{3'}C(O)R^3$, —$NR^{3'}C(O)NR^{3'}R^3$, —(SO)$R^3$, —(SO$_2$)$R^3$, —NHSO$_2R^3$, and —SO$_2NR^{3'}R^3$, with $R^3$ and $R^{3'}$ being substituents independently selected from the group consisting of H, substituted or unsubstituted $C_1$-$C_6$-alkyl, substituted or unsubstituted $C_2$-$C_6$-alkenyl, substituted or unsubstituted aryl, substituted or unsubstituted heteroaryl, substituted or unsubstituted aryl-$C_1$-$C_6$-alkyl, and substituted or unsubstituted heteroaryl-$C_1$-$C_6$-alkyl;

said aryl or heteroaryl groups being optionally substituted $C_1$-$C_6$-alkyl, $C_1$-$C_6$-alkoxy, $C_2$-$C_6$-alkenyl, $C_2$-$C_6$-alkynyl, amino, acylamino, aminocarbonyl, $C_1$-$C_6$-alkoxycarbonyl, aryl, carboxyl, cyano, halogen, hydroxy, nitro, sulfonyl, sulfoxy, or $C_1$-$C_6$-thioalkoxy; and $R^6$ is selected from the group consisting of hydrogen, substituted or unsubstituted $C_1$-$C_6$-alkyl, substituted or unsubstituted $C_1$-$C_6$-alkoxy, OH, halogen, nitro, cyano, sulfonyl, and oxo (=O); and n' is an integer from 0 to 4;

and a pharmaceutically acceptable carrier.

15. The composition according to claim 14 wherein n is an integer of from 1 to 3.

16. The composition according to claim 15 wherein n is 1.

17. The composition according to claim 14 wherein n is 1 or 2.

18. Process for the preparation of a sulfonamide compound according to claim 1, comprising reacting a sulfonyl chloride according to formula V

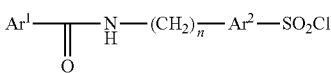

V with an amine according to formula VIII

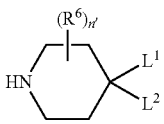

VIII whereby
n is an integer of from 0 to 5,
n' is an integer of from 0 to 4,
$R^6$ is selected from the group consisting of hydrogen, substituted or unsubstituted $C_1$-$C_6$ alkyl, substituted or unsubstituted $C_1$-$C_6$ alkoxy, OH, halogen, nitro, cyano, sulfonyl and oxo;

$L^1$ and $L^2$ are independently selected from the group consisting of hydrogen, substituted or unsubstituted $C_2$-$C_6$ alkyl, substituted or unsubstituted $C_2$-$C_6$ alkenyl, and substituted or unsubstituted $C_3$-$C_6$ alkynyl; or $L^1$ and $L^2$ are independently selected from the group consisting of substituted or unsubstituted aryl, substituted or unsubstituted heteroaryl, aryl-$C_1$-$C_6$ alkyl, heteroaryl-$C_1$-$C_6$ alkyl, substituted or unsubstituted cyclic $C_4$-$C_8$ alkyl optionally containing 1-3 heteroatoms and optionally fused with aryl or heteroaryl, —C(O)$R^3$, —C(O)$OR^3$, —C(O)—$NR^{3'}R^3$, —$NR^{3'}R^3$, —$NR^{3'}O(O)R^3$, —$NR^{3'}C(O)R^{3'}R^3$, —(SO)$R^3$, (SO$_2$)$R^3$, NHSO$_2R^3$ and SO$_2NR^{3'}R^3$;

with $R^3$ and $R^{3'}$ being substituents independently selected from the group consisting of hydrogen, substituted or unsubstituted $C_1$-$C_6$ alkyl, substituted or unsubstituted aryl, substituted or unsubstituted heteroaryl, substituted or unsubstituted aryl-$C_1$-$C_6$ alkyl and substituted or unsubstituted heteroaryl-$C_1$-$C_6$ alkyl;

said aryl or heteroaryl groups being optionally substituted $C_1$-$C_6$ alkyl, $C_1$-$C_6$ alkoxy, $C_2$-$C_6$ alkenyl, $C_2$-$C_6$ alkynyl, amino, acylamino, aminocarbonyl, $C_2$-$C_6$ alkoxycarbonyl, aryl, carboxyl, cyano, halogen, hydroxy, nitro, sulfonyl, sulfoxy and $C_1$-$C_6$ thioalkoxy.

19. A process according to claim 18, wherein said sulfonyl chloride of formula V is obtained by a) coupling an amine of formula II:

$R^1HN$—$(CH_2)_n$—$Ar^2$     II with an acyl chloride of formula III:

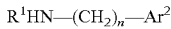

III to provide an amide of formula IV:

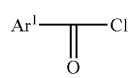

IV b) sulfonating the amide of formula IV to provide the sulfonyl chloride of formula V

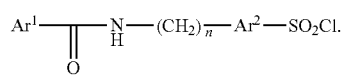

V

* * * * *